United States Patent
Wheeler et al.

(10) Patent No.: US 10,357,566 B2
(45) Date of Patent: Jul. 23, 2019

(54) HER3 INHIBITOR FOR MODULATING RADIOSENSITIVITY

(71) Applicant: DAIICHI SANKYO EUROPE GMBH, Munich (DE)

(72) Inventors: Deric L. Wheeler, Madison, WI (US); Thore Hettmann, Martinsried (DE)

(73) Assignee: DAIICHI SANKYO EUROPE GMBH, Munich (DE)

( * ) Notice: Subject to any disclaimer, the term of this patent is extended or adjusted under 35 U.S.C. 154(b) by 0 days.

(21) Appl. No.: 14/380,268

(22) PCT Filed: Feb. 22, 2013

(86) PCT No.: PCT/EP2013/053562
§ 371 (c)(1),
(2) Date: Aug. 21, 2014

(87) PCT Pub. No.: WO2013/124419
PCT Pub. Date: Aug. 29, 2013

(65) Prior Publication Data
US 2015/0017096 A1 Jan. 15, 2015

Related U.S. Application Data

(60) Provisional application No. 61/602,239, filed on Feb. 23, 2012.

(51) Int. Cl.
| | | |
|---|---|---|
| *A61K 39/395* | (2006.01) | |
| *A61K 41/00* | (2006.01) | |
| *A61K 51/10* | (2006.01) | |
| *A61N 5/10* | (2006.01) | |
| *C07K 16/38* | (2006.01) | |
| *C07K 16/32* | (2006.01) | |
| *A61K 39/00* | (2006.01) | |

(52) U.S. Cl.
CPC ...... *A61K 41/0038* (2013.01); *A61K 51/1075* (2013.01); *A61K 51/1096* (2013.01); *A61N 5/10* (2013.01); *C07K 16/32* (2013.01); *A61K 2039/505* (2013.01); *A61N 2005/1098* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,480,968 A | 1/1996 | Kraus et al. | |
| 5,958,770 A * | 9/1999 | Cham | A61K 31/20 424/DIG. 14 |
| 5,968,511 A | 10/1999 | Akita et al. | |
| 7,625,558 B2 * | 12/2009 | Greene | A61K 38/1709 424/130.1 |
| 2005/0239738 A1 * | 10/2005 | Schmidt-Ullrich | A61K 48/005 514/44 R |
| 2008/0124345 A1 * | 5/2008 | Rothe | C07K 16/2863 424/174.1 |
| 2011/0033482 A1 | 2/2011 | Ullrich et al. | |
| 2011/0229406 A1 | 9/2011 | Hettmann et al. | |

FOREIGN PATENT DOCUMENTS

| | | |
|---|---|---|
| EP | 0 239 400 | 8/1994 |
| EP | 2 138 511 | 12/2009 |
| JP | 2002-515511 | 5/2002 |
| WO | 90/07861 | 7/1990 |
| WO | 99/60023 | 11/1999 |
| WO | 03/013602 | 2/2003 |
| WO | 2007/077028 | 7/2007 |
| WO | 2011/060206 | 5/2011 |

OTHER PUBLICATIONS

Alimandi et al., "Cooperative Signaling of ErbB3 and ErbB2 in Neoplastic Transformation and Human Mammary Carcinomas", *Oncogene*, vol. 10, pp. 1813-1821, 1995.
Binz et al., "Engineered Proteins as Specific Binding Reagents", *Current Opinion in Biotechnology*, vol. 16, pp. 459-469, 2005.
DeFazio et al., "Expression of c-erbB Receptors, Heregulin and Oestrogen Receptor in Human Breast Cell Lines", *Int. J. Cancer*, vol. 87, pp. 487-498, 2000.
Dote et al., "ErbB3 Expression Predicts Tumor Cell Radiosensitization Induced by Hsp90 Inhibition", *Cancer Res.*, vol. 65, No. 15, pp. 6967-6975, 2005.
Rao et al., "Radiosensitization of Human Breast Cancer Cells by a Novel ErbB Family Receptor Tyrosine Kinase Inhibitor", *Int. J. Radiation Oncology Biol. Phys.*, vol. 48, No. 5, pp. 1519-1528, 2000.
Contessa et al., "Compensator ErbB3/c-Src Signaling Enhances Carcinoma Cell Survival to Ionizing Radiation", *Breast Cancer Research and Treatment*, vol. 95, pp. 17-27, 2006.
Kraus et al., "Isolation and Characterization of *ERBB3*, a Third Member of the *ERBB*/Epidermal Growth Factor Receptor Family: Evidence for Overexpression in a Subset of Human Mammary Tumors", *Proc. Natl. Acad. Sci. USA*, vol. 86, pp. 9193-9197, 1989.
Kraus et al., "Demonstration of Ligand-Dependent Signaling by the *erbB-3* Tyrosine Kinase and Its Constitutive Activation in Human Breast Tumor Cells", *Proc. Natl. Acad. Sci. USA*, vol. 90, pp. 2900-2904, 1993.
Naidu et al., "Expression of c-*erb*B3 Protein in Primary Breast Carcinomas", *British Journal of Cancer*, vol. 78, No. 10, pp. 1385-1390, 1998.
Köhler et al., "Continuous Cultures of Fused Cells Secreting Antibody of Predefined Specificity", *Nature*, vol. 256, No. 5517, pp. 495-497, 1975.
Plowman et al., "Molecular Cloning and Expression of an Additional Epidermal Growth Factor Receptor-Related Gene", *Proc. Natl. Acad. Sci. USA*, vol. 87, pp. 4905-4909, 1990.

(Continued)

*Primary Examiner* — Hong Sang
(74) *Attorney, Agent, or Firm* — Greenblum & Bernstein, P.L.C.

(57) ABSTRACT

The present invention relates to the use of an inhibitor of HER-3 for the treatment of a hyperproliferative disease in combination with radiation treatment.

21 Claims, 7 Drawing Sheets
(1 of 7 Drawing Sheet(s) Filed in Color)
Specification includes a Sequence Listing.

(56) References Cited

OTHER PUBLICATIONS

Written Opinion of the ISA for PCT/EP2013/053562, dated Jun. 4, 2013.
International Search Report for PCT/EP2013/053562, dated Jun. 4, 2013.
P.M. Harari, et al. "Beyond Cetuximab for Head and Neck Cancer: Dual Target Antibody Blockade of EGFR and HER3 Enhances Radiosensitivity and Overcomes Acquired Resistance to EGFR Inhibitors." Intl J. of Radiation Oncology, Biology, Physics. vol. 81, Issue 2., Supplement (Jan. 10, 2011), p. S77.
European Office Action dated May 28, 2019 in European Application No. 13705987.9.

* cited by examiner

HER3 INHIBITOR FOR MODULATING RADIOSENSITIVITY

This invention was made with government support under grant UL1TR000427 awarded by the National Institutes of Health, National Center for Advancing Translational Sciences. The government has certain rights in the invention.

SEQUENCE LISTING

The instant application contains a Sequence Listing which has been submitted electronically in ASCII format, and which is hereby incorporated by reference in its entirety.

The present invention relates to the use of an inhibitor of HER-3 for the treatment of a hyperproliferative disease in combination with radiation treatment.

The human epidermal growth factor receptor 3 (HER-3, also known as ErbB3) is a receptor protein tyrosine kinase and belongs to the epidermal growth factor receptor (EGFR) subfamily of receptor protein tyrosine kinases, which also includes HER-1 (also known as EGFR), HER-2, and HER-4 (Plowman et al., *Proc. Natl. Acad. Sci. U.S.A.* 87 (1990), 4905-4909; Kraus et al., *Proc. Natl. Acad. Sci. U.S.A.* 86 (1989), 9193-9197; and Kraus et al., *Proc. Natl. Acad. Sci. U.S.A.* 90 (1993), 2900-2904). Like the prototypical epidermal growth factor receptor, the transmembrane receptor HER-3 consists of an extracellular ligand-binding domain (ECD), a dimerization domain within the ECD, a transmembrane domain, an intracellular protein tyrosine kinase domain (TKD) and a C-terminal phosphorylation domain.

The ligand Heregulin (HRG) binds to the extracellular domain of HER-3 and activates the receptor-mediated signaling pathway by promoting dimerization with other human epidermal growth factor receptor (HER) family members and transphosphorylation of its intracellular domain. Dimer formation between HER family members expands the signalling potential of HER-3 and is a means not only for signal diversification but also signal amplification. For example the HER-2/HER-3 heterodimer induces one of the most important mitogenic signals among HER family members.

HER-3 has been found to be overexpressed in several types of cancer such as breast, gastrointestinal and pancreatic cancers. Interestingly a correlation between the expression of HER-2/HER-3 and the progression from a non-invasive to an invasive stage has been shown (Alimandi et al., *Oncogene* 10, 1813-1821; deFazio et al., *Cancer* 87, 487-498; Naidu et al., *Br. J. Cancer* 78, 1385-1390). Accordingly, agents that interfere with HER-3 mediated signaling are desirable. Murine or chimeric HER-3 antibodies have been reported, such as in U.S. Pat. Nos. 5,968,511, 5,480,968 and WO03013602.

The object of the present invention was to provide treatment of hyperproliferative diseases, in particular cancer, based on the inhibition of HER-3 being more effective than known from the prior art. This object is solved by the use of an inhibitor of HER-3 for the treatment of a hyperproliferative disease in combination with radiation treatment.

According to a first aspect the present invention relates to the use of an inhibitor of HER-3 for the treatment of a hyperproliferative disease in combination with radiation treatment.

The treatment of a combination of a HER-3 inhibitor and radiotherapy leads to synergistic effects which exceed the advantages of a treatment with either a HER-3 inhibitor or radiotherapy alone.

An inhibitor of HER-3 according to the present invention may act on the protein level or on the nucleic acid level. Examples for inhibitors acting on the nucleic acid level are known to the person skilled in the art and comprise antisense molecules, RNAi molecules and/or ribozymes.

Examples for an inhibitor acting on the protein level is an anti-HER-3-antibody or an antigen-binding fragment thereof as well as scaffold proteins. The inhibitor being an anti-HER-3 antibody or a fragment thereof, in particular an antigen-binding fragment thereof, represents a preferred embodiment of the present invention. According to the invention term "antibody fragment" comprises any portion of the afore-mentioned antibodies, preferably their antigen binding or variable regions.

As used herein, "scaffold protein" represents an protein having an antibody like binding activity or an antibody, i.e. an anti-HER-3 antibody. Within the context of the present invention, the term "scaffold protein", as used herein, means a polypeptide or protein with exposed surface areas in which amino acid insertions, substitutions or deletions are highly tolerable. Examples of scaffold proteins that can be used in accordance with the present invention are protein A from *Staphylococcus aureus*, the bilin binding protein from *Pieris brassicae* or other lipocalins, ankyrin repeat proteins, and human fibronectin (reviewed in Binz and Plückthun, *Curr Opin Biotechnol*, 16, 459-69). In addition, a scaffold protein having an antibody like binding activity can be derived from an acceptor polypeptide containing the scaffold domain, which can be grafted with binding domains of a donor polypeptide to confer the binding specificity of the donor polypeptide onto the scaffold domain containing the acceptor polypeptide.

The anti-HER-3 antibody according to the invention may be a monoclonal antibody, a polyclonal antibody, a recombinant antibody, a human antibody, a humanized antibody, a chimeric antibody, a multispecific antibody or an antigen-binding fragment thereof. The use of a monoclonal antibody is especially preferred. A person skilled in the art knows how to produce such antibodies. Monoclonal antibodies may, e.g., be produced by any suitable method such as that of Köhler and Millstein (Nature, 1975; 256:495-497).

An antibody fragment according to the invention is preferably a Fab fragment, a Fab' fragment, a F(ab')$_2$ fragment, a Fv fragment, a diabody, or a single chain antibody molecule. The "Fab fragment" differs from the "Fab' fragment" by the addition of a few residues at the carboxy terminus of the heavy chain CH1 domain including one or more cysteines from the antibody hinge region. The "F(ab')$_2$ fragment" originally is produced as a pair of "Fab' fragments" which have hinge cysteines between them. In accordance with the present invention, the "Fv fragment" is the minimum antibody fragment that contains a complete antigen-recognition and -binding site.

The antibody used according to the invention may be preferably of the IgG1, IgG2, IgG3 or IgG4 antibody type.

Humanized forms of antibodies represent a further preferred embodiment and may be generated according to the methods known in the art such as humanization or CDR grafting. Alternative methods for producing humanized antibodies are well-known in the art and described, for instance, in EP 0 239 400 and WO 90/07861. Human antibodies avoid certain of the problems associated with xenogeneic antibodies, for example antibodies that possess murine or rat variable and/or constant regions. Monoclonal humanized anti-HER-3 antibodies represent an especially preferred embodiment of the invention.

According to a further preferred embodiment the antibody is directed against the extracellular domain of HER-3. The anti-HER-3 antibody preferably interacts with at least one epitope in the extracellular part of HER-3. The epitopes are preferably located in domain L1 (AA19-184), which is the amino terminal domain, in domain S1 (AA185-327) and S2 (AA500-632), which are the two cystein-rich domains or in domain L2 (328-499), which is flanked by the two cystein-rich domains. The epitopes may also be located in any combination of domains such as, but not limited to, an epitope comprised by parts of L1 and S2.

The anti-HER-3 antibody used may be coupled to an effector and/or a labelling group. Corresponding coupling and/or labelling techniques are known to the person skilled in the art. Such effector and/or labelling groups may be attached for drug targeting, imaging applications and/or diagnostic applications.

As used herein, the term "labelling group" refers to a detectable marker, e.g. a radiolabelled amino acid or biotinyl moiety that can be detected by marked avidin (e.g. streptavidin bound to a fluorescent marker or enzymatic activity that can be detected by optical or colorimetric methods). Examples of suitable labelling groups include, but are not limited to, the following: radioisotopes or radionuclides (e.g. $^{3}H$, $^{14}C$, $^{15}N$, $^{35}S$, $^{90}Y$, $^{99}Tc$, $^{111}In$, $^{125}I$, $^{131}I$), fluorescent groups (e.g. FITC, rhodamine, lanthanide phosphors), enzymatic groups (e.g. horseradish peroxidase, β-galactosidase, luciferase, alkaline phosphatase), chemiluminescent groups, biotinyl groups, or predetermined polypeptide epitopes recognized by a secondary reporter (e.g. leucine zipper pair sequences, binding sites for secondary antibodies, metal binding domains, epitope tags). In certain aspects, it may be desirable that the labelling groups are attached by spacer arms of various lengths to reduce potential steric hindrance.

Alternatively, an anti-HER-3 antibody used according to the invention may be coupled to an effector group. As used herein, the term "effector group" refers to a cytotoxic group such as a radioisotope or radionuclide, a toxin, a therapeutic group or other effector group known in the art. Examples for suitable effector groups are radioisotopes or radionuclides (e.g. $^{3}H$, $^{14}C$, $^{15}N$, $^{35}S$, $^{90}Y$, $^{99}Tc$, $^{111}In$, $^{125}I$, $^{131}I$), calicheamicin, dolastatin analogs such as auristatins, and chemotherapeutic agents such as geldanamycin and maytansine derivates, including DM1. In certain aspects, it may be desirable that the effector groups are attached by spacer arms of various lengths to reduce potential steric hindrance.

In addition to the inhibition of HER-3, it is possible according to a further preferred embodiment to carry out or support the radiation treatment by labelling the anti-HER-3 antibody with a corresponding effector group such as radio-isotopes or radionuclides outlined above.

Moreover, the HER-3 inhibitor used, and in particular the anti-HER-3 antibody used, according to the invention may be further characterized in that its binding to HER-3 reduces HER-3-mediated signal transduction. In accordance with the present invention, a reduction of HER-3-mediated signal transduction may, e.g. be caused by a downregulation of HER-3 resulting in an at least partial disappearance of HER-3 molecules from the cell surface or by a stabilization of HER-3 on the cell surface in a substantially inactive form, i.e. a form which exhibits a lower signal transduction compared to the non-stabilized form. Alternatively, a reduction of HER-3-mediated signal transduction may also be caused by influencing, e.g. decreasing or inhibiting, the binding of a ligand or another member of the HER family to HER-3, of GRB2 to HER-2 or of GRB2 to SHC, by inhibiting receptor tyrosine phosphorylation, AKT phosphorylation, PYK2 tyrosine phosphorylation or ERK2 phosphorylation, or by decreasing tumour invasiveness. Alternatively, a reduction of HER-3 mediated signal transduction may also be caused by influencing, e.g., decreasing or inhibiting, the formation of HER-3 containing dimers with other HER family members. One example among others may be the decreasing or inhibiting of the HERS-EGFR protein complex formation.

Preferred anti-HER-3 antibodies used according to the present invention are described in PCT/EP2006/012632.

According to an especially preferred embodiment the antibody comprises a heavy chain amino acid sequence that comprises at least one of the CDR's selected from the group consisting of (a) CDRH1's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230; (b) CDRH2's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230; and (c) CDRH3's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230 or a heavy chain amino acid sequence that shows at least 90%, 92%, 94%, 96%, 97%, 98%, 99% homology to one of the CDRs according to (a) to (c).

According to a further preferred embodiment the antibody comprises wherein the antibody comprises a light chain amino acid sequence that comprises at least one of the CDR's selected from the group consisting of: (d) CDRL1's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232; (e) CDRL2's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232; and (f) CDRL3's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232 or or a light chain amino acid sequence that shows at least 90%, 92%, 94%, 96%, 97%, 98%, 99% homology to one of the CDRs according to (d) to (f).

In yet another embodiment of the present invention the antibody comprises a heavy chain amino acid sequence that comprises at least one of the CDR's selected from the group consisting of (a) CDRH1's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230;

(b) CDRH2's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230; and (c) CDRH3's as shown in SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230, and a light chain amino acid sequence that comprises at least one of the CDR's selected from the group consisting of:

(d) CDRL1's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232;

(e) CDRL2's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232; and (f) CDRL3's as shown in SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

According to a further preferred embodiment, the antibody comprises a CDRH1, a CDRH2, a CDRH3, a CDRL1, a CDRL2 and a CDRL3.

According to a further preferred embodiment, an anti-HER-3 antibody used according to the invention comprises a heavy chain amino acid sequence selected from the group consisting of SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230.

A further preferred embodiment relates to the use of an anti-HER-3 antibody comprising a light chain amino acid sequence selected from the group consisting of SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

According to yet another preferred embodiment, an anti-HER-3 antibody used according to the invention comprises a heavy chain amino acid sequence selected from the group consisting of SEQ ID NOs: 2, 6, 10, 14, 18, 22, 26, 30, 34, 36, 40, 42, 46, 50, 54, 60, 62, 66, 70, 74, 78, 80, 84, 88, 92, 96, 100, 104, 108, 112, 116, 120, 122, 126, 130, 134, 138, 142, 146, 150, 154, 158, 162, 166, 170, 174, 178, 182, 186, 190, 194, 198, 202, 206, 210, 214, 218, 222, 226 and 230; and a light chain amino acid sequence selected from the group consisting of SEQ ID NOs: 4, 8, 12, 16, 20, 24, 28, 32, 38, 44, 48, 52, 56, 58, 64, 68, 72, 76, 82, 86, 90, 94, 98, 102, 106, 110, 114, 118, 124, 128, 132, 136, 140, 144, 148, 152, 156, 160, 164, 168, 172, 176, 180, 184, 188, 192, 196, 200, 204, 208, 212, 216, 220, 224, 228 and 232.

Especially preferred embodiments relate to anti-HER-3 antibodies comprising the heavy chain amino acid sequence of SEQ ID NO:42 and the light chain amino acid sequence of SEQ ID NO:44, or comprising the heavy chain amino acid sequence of SEQ ID NO:54 and the light chain amino acid sequence of SEQ ID NO:56, or comprising the heavy chain amino acid sequence of SEQ ID NO:70 and the light chain amino acid sequence of SEQ ID NO:72.

In particular, the anti-HER-3 antibody is selected from the group consisting of U1-1 antibody, U1-2 antibody, U1-3 antibody, U1-4 antibody, U1-5 antibody, U1-6 antibody, U1-7 antibody, U1-8 antibody, U1-9 antibody, U1-10 antibody, U1-11 antibody, U1-12 antibody, U1-13 antibody, U1-14 antibody, U1-15 antibody, U1-16 antibody, U1-17 antibody, U1-18 antibody, U1-19 antibody, U1-20 antibody, U1-21 antibody, U1-22 antibody, U1-23 antibody, U1-24 antibody, U1-25 antibody, U1-26 antibody, U1-27 antibody, U1-28 antibody, U1-29 antibody, U1-30 antibody, U1-31 antibody, U1-32 antibody, U1-33 antibody, U1-34 antibody, U1-35 antibody, U1-36 antibody, U1-37 antibody, U1-38 antibody, U1-39 antibody, U1-40 antibody, U1-41 antibody, U1-42 antibody, U1-43 antibody, U1-44 antibody, U1-45 antibody, U1-46 antibody, U1-47 antibody, U1-48 antibody, U1-49 antibody, U1-50 antibody, U1-51 antibody, U1-52 antibody, U1-53 antibody, U1-55.1 antibody, U1-55 antibody, U1-57.1 antibody, U1-57 antibody, U1-58 antibody, U1-59 antibody, U1-61.1 antibody, U1-61 antibody, U1-62 antibody or an antibody having at least one heavy or light chain of one of said antibodies. Especially preferred are the antibodies U1-49 (SEQ ID NO: 42/44), U1-53 (SEQ ID NO: 54/56) and U1-59 (SEQ ID NO: 70/72) or an antibody having at least one heavy or light chain of one of said antibodies. The antibody U1-59 is particular preferred.

The disease to be treated according to the present invention is a hyperproliferative disease. This hyperproliferative disease is preferably cancer, in particular squamous cell carcinoma.

Examples of cancer which are preferably treated according to the present invention are selected from the group consisting of breast cancer, gastrointestinal cancer, pancreas cancer, prostate cancer, ovarian cancer, stomach cancer, endometrial cancer, salivary gland cancer, lung cancer, kidney cancer, colon cancer, colorectal cancer, thyroid cancer, bladder cancer, glioma, melanoma, testis cancer, soft tissue sarcoma, head and neck cancer, other HER-3 expressing or overexpressing cancers, and formation of tumour metastases.

According to an especially preferred embodiment the cancer is squamous cell carcinoma of the lung, of the head and/or the neck.

Radiation treatment according to the present invention is preferably selected from heat treatment, external beam radiation therapy, brachytherapy and/or radioisotopetherapy. The person skilled in the art can determine which kind of radiation treatment and in particular which kind of radiation source to be used for a particular patient to be treated.

External beam radiotherapy is the most common form of radiotherapy. In contrast to internal radiotherapy (brachytherapy), external beam radiotherapy directs the radiation at the tumour from outside the body. The voltage to be used may be determined by the person skilled in the art and depends inter alia on the kind of the tumour to be treated. For example, kilovoltage X-rays may be used for treating skin cancer and superficial structures whereas megavoltage X-rays may be used for treating deep-seated tumours (e.g., prostate, lung or brain). While X-ray and electron beams are by far the most widely used sources for external beam radiotherapy, also heavier particle beams such as proton beams may be used.

As already outlined above, brachytherapy is also known as internal radiotherapy. It is a form of radiotherapy, where a radiation source is placed inside or next to the area requiring treatment. In brachytherapy radiation sources are precisely placed directly at the side of the cancerous tumour. This means that the radiation only affects a limited local area which provides advantages over X-ray beam radiation therapy. For example, the tumour may be treated with very high doses of localized radiation whilst reducing the probability of unnecessary damage to surrounding healthy tissues. Examples of radiation sources used for brachytherapy comprise $^{125}$I/$^{103}$Pd, $^{90}$Y as well as Selective internal radiation therapy (SIRT). SIRT comprises the use of microspheres, which might be, for example, injected. Such microspheres can be made of resin or glass. Inside the microsphere the radiation source such as yttrium-90 can be placed. Examples of microspheres which are used already are ThereSphere and SIR-Spheres, which differ in their radioactivity per sphere and embolic effect. Of course, the use of any further suitable carrier coupled to a radiation source is also contemplated. Further examples for medicaments used in brachytherapy comprise SAVI, MammoSite, Contura, Proxcelan and I-Seed.

Radioisotope therapy represents a further form of targeted therapy. Targeting can be due to the chemical properties of the isotope. The radioisotopes may be, for example, delivered by infusion or ingestion. Examples of radioisotopes used for treatment comprise iodine-131, luteium-177 and yttrium-90, strontium-89 and samarium-153.

Radiation treatment and/or radiation treatment may be used according to the invention may be based on an single dose or fractionated dosing of radiation. Of course, is also possible to vary the duration of radiation therapy. The duration may depend on the location of the tumours to be treated, the size of the tumour to be treated and the physical condition of the patient.

The combination of an inhibitor of HER-3 and radiation therapy and/or treatment according to the present invention contemplates the simultaneous treatment with an HER-3 inhibitor and radiation therapy as well as a timely shifted combination. According to a preferred embodiment tumour cells to be treated are radiosensitized by the HER-3 inhibitor before radiation treatment, i.e. the HER-3 inhibitor is administered before radiation treatment/therapy.

The present invention can be used in combination with a further active compound like a further chemotherapeutic compound such as cytotoxic agents, such as doxorubicin, cis-platin or carboplatin, cytokines or antineoplatic agents.

Another aspect of the present invention relates to the use of an inhibitor of HER-3 for the modulation of radiosensitivity of cells.

BRIEF DESCRIPTION OF THE FIGURES

The patent or application file contains at least one drawing executed in color. Copies of this patent or patent application publication with color drawing(s) will be provided by the Office upon request and payment of the necessary fee.

Figure 1:
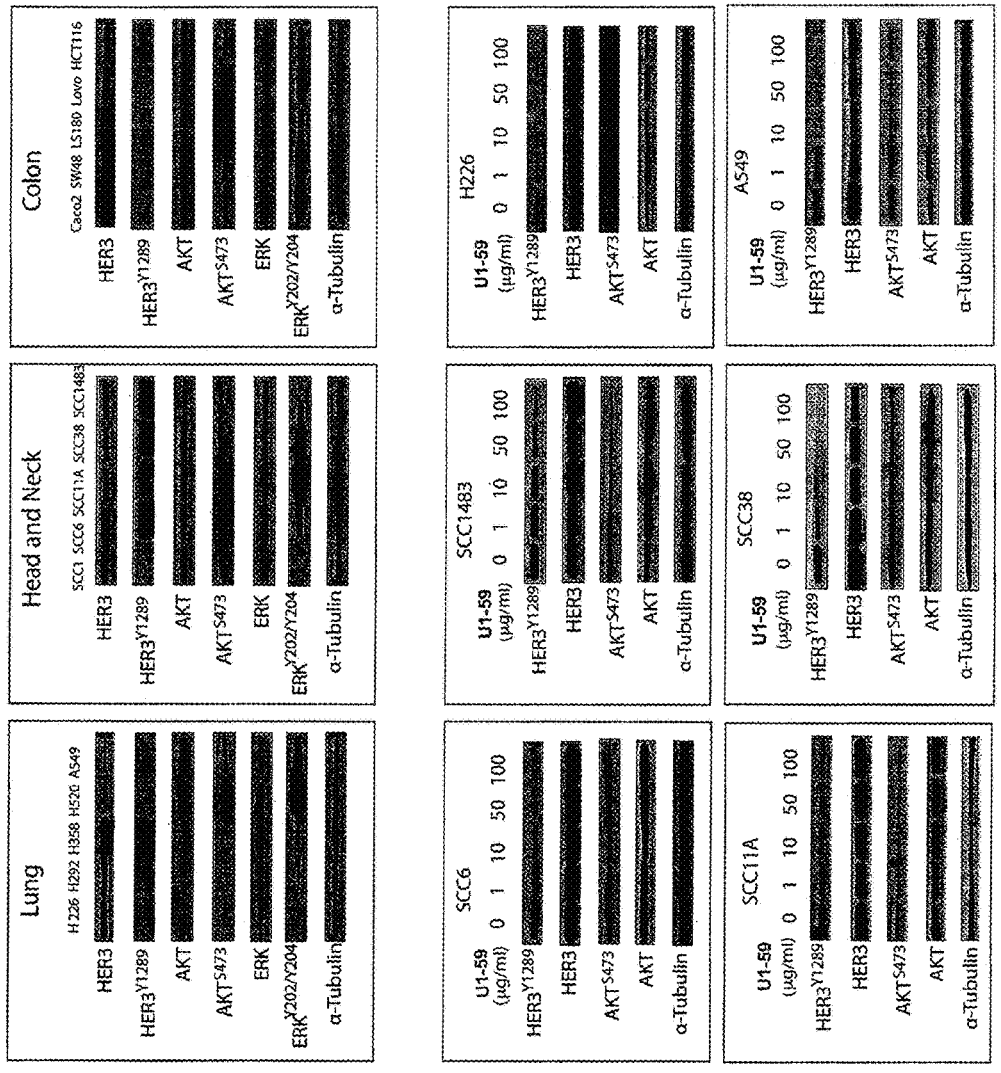
FIG. 1.

(A) HER3 Profile in Multiple Carcinoma Celllines.

Five human lung carcinoma celllines (NCI-H226, H292, H358, H520 and A549), five colorectal carcinoma celllines (Caco2, SW48, LS180, Lovo and HCT116) and five head and neck carcinoma celllines (SCC1, SCC6, SCC11A, SCC38 and SCC1483) were cultured in relevant mediums. Whole cell lysate was obtained with lysis buffer. Protein was quantitated using the Bradford method, separated by SDS gel and followed by immunoblot with the indicated antibodies.

(B) Basal Activity of HER3 is Blocked by U1-59.

Four head and neck carcinoma celllines (SCC6, SCC11A, SCC38, SCC1483) with high p-HER3 and two lung cancer celllines (H226 and A549) were treated with doses of U1-59 for 24 h. Whole cell lysates were isolated and followed by immunoblot with indicated antibodies. U1-59 inhibited HER3 activity and its downstream signal in a dose-dependent manner in those cells.

FIG. 2:

Radiation-induced activation of HER3 is blocked by U1-59. (A, D) HER3 was transient activated by radiation during the indicated time and blocked by U1-59. SCC6 and H226 cells were incubated with/without U1-59 (20 ug/ml) for 24 h before radiation. After exposure to 4 Gy radiation, whole cell lysates were isolated at the indicated times, followed by immunoblot with p-HER, p-AKT and p-MAPK antibodies. (B, E) U1-59 kept blocking activations of AKT and MAPK 24 h and 48 h after radiation. (C, F) Immunoflurescence showing HER3 were activated by radiation and blocked by U1-59 in SCC6 and H226 cells (30 minutes after radiation).

FIG. 3.

(A, F) U1-59 Inhibited Cell Proliferation in a Dose-Dependent Manner.

SCC6 and H226 cells were seeded in 96-well plates and incubated with doses of U1-59 for 72 h. Cell proliferation were detected using CCK8 72 h.

(B, G) Sensitizing Effect of U1-59 on SCC6 Cells in Response to Radiation.

SCC6 and H226 were incubated with U1-59 for 4 h, and radiated with indicated doses. Clonegenic assay were performed as described. Control curves were exposed to radiation without U1-59 treatment.

(C, H) Impact of U1-59 on Cell Cycle.

SCC6 and H226 cells were incubated with U1-59 (20 ug/ml) for 48 h, followed by exposure to 6 Gy radiation. 24 h after radiation, cell cycle (stained with PI) was detected using flow cytometer and analyzed by FlowJo. U1-59 caused G1 arrest and radiation caused G2 arrest. Combination of U1-59 and radiation reasserted cell within cell cycle, induced accumulation of cells in G1 and G2, and reduced the population of cells in S phase.

(D, I) Impact of U1-59 on Cell Apoptosis.

Apoptosis (stained with annexin V/PI) was detected using flow cytometer and analyzed by FlowJo. Combination of U1-59 with radiation increased the percentage of apoptotic cells.

(E, J) U1-59 Contribute to γ-H2AX Focus Formation.

SCC6 and H226 were incubated with U1-59 for 24 h before 4 Gy radiation. 4 h after radiation, cells were fixed and performed immunofluorescence staining. Compared with drug or radiation alone, increased number of γ-H2AX foci was detected in the cell treated with XRT combined with U1-59, demonstrated enhanced DNA damage by U1-59

FIG. 4.

Antitumour effect of U1-59 combined with radiation on xenograft tumours in athymic mice. SCC6, SCC1483 and H226 xenograft were performed as described in "Materials and methods". (A) Mice were treated with single dose of IgG, radiation (10 Gy or 16 Gy), U1-59 (8 mg/kg) or combination of both. Data points were expressed as mean tumour size±SD. Results were graphed with tumour growth curve and Kaplan Meir survival curve. (B) Mice were treated with fractionated doses of IgG, radiation, U1-59 (100 ug/mouse) or combination of both twice a week as shown. Results were graphed with tumour growth curve and Kaplan Meir survival curve.

FIG. 5.

Figure 5:
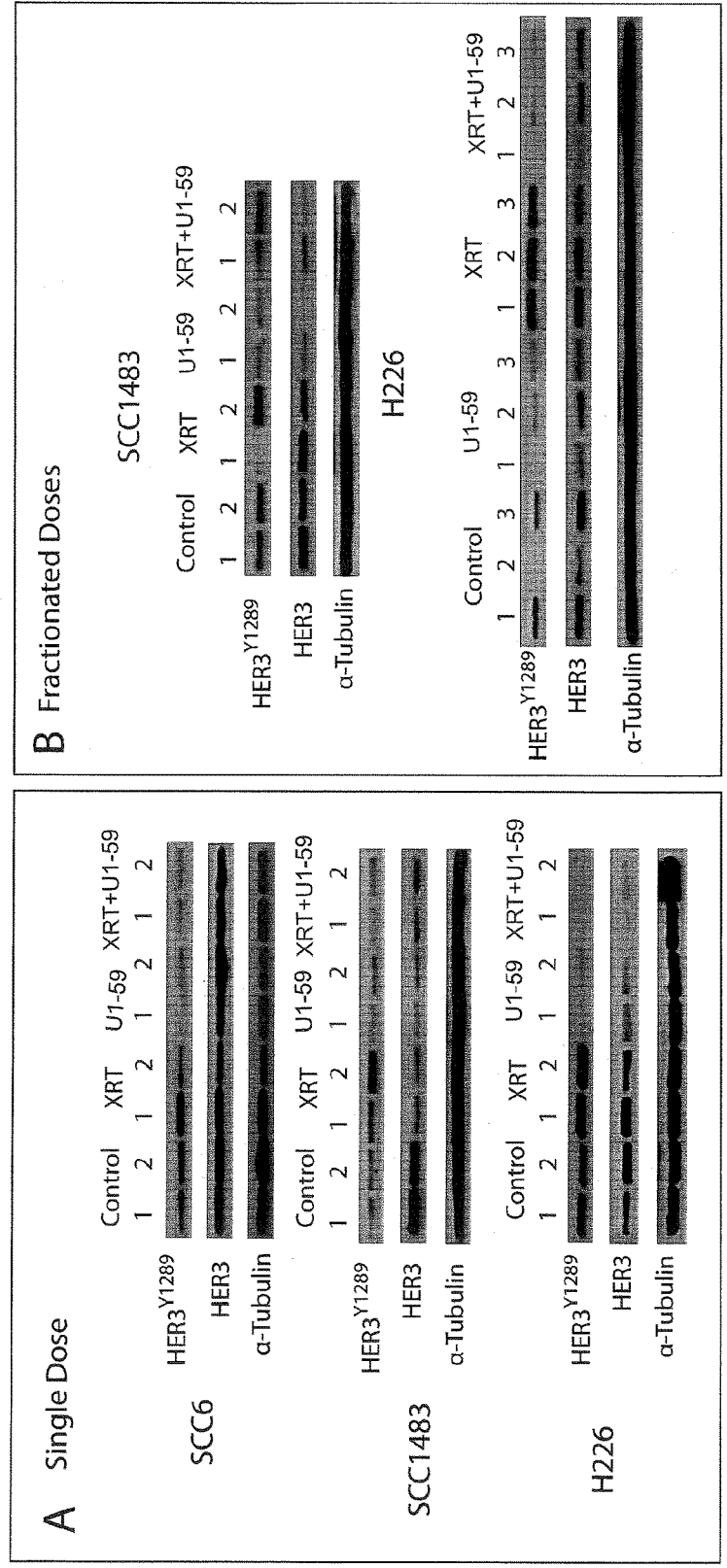

U1-59 inhibits basal and radiation-induced activation of HER3 in xenograft tumours. SCC6, SCC1483 and H226 xenograft tumours were collected at 24 h post radiation or the last radiation in fractionated treatment groups. Protein was isolated from the tumours and p-HER3 was analyzed by western blot (FIG. 5A and FIG. 5B). Increased p-HER3 was found in radiated tumours and reduced p-HER3 was found in tumours with U1-59 or combined treatment.

FIG. 6.

U1-59 inhibits cell survival signals and enhances DNA damage in combination with radiation on xenograft tumours in athymic mice. SCC6 xenograft tumours with single dose treatment of radiation (16 Gy), U1-59 (8 mg/kg) or combination of both. Tumours were harvested 24 h post treatment. IHC stain were performed as describe in "Materials and methods". Reduced p-MAPK, p-S6 and PCNA staining, decreased PCNA positive cells and increased γ-H2AX positive cells were detected in tumours with U1-59 or combined treatment.

EXAMPLES

Materials and Methods
Cell Culture and Drug

Five human lung carcinoma celllines (NCI-H226, H292, H358, H520 and A549 and five colorectal carcinoma celllines (Caco2, SW48, LS180, Lovo and HCT116) were purchased from ATCC (Manassas, Va., USA) and maintained in 10% fetal bovine serum (FBS) in RPMI1640 or DMEM (Mediatech Inc., Manassas, Va., USA) with 1% penicillin and streptomycin. Five head and neck carcinoma celllines (UM-SCC1, UM-SCC4, UM-SCC6, UM-SCC11A, and UM-SCC1483 cells) were obtained from University of Michigan and maintained in 10% FBS (Invitrogen, Carlsbad, Calif., USA) in DMED supplemented with 1% hydrocortisone.

The anti-HER-3 antibody U1-59 was used.
Cell Proliferation Assay

Cells were seeded in 96-well plate and exposed to doses of U1-59 for 72 h. Cell proliferation was tested by Cell Counting Kit-8 (Dojindo Molecular Technologies, Gaithersbury, Md., USA).
Clonogenic Assay A specified number of cells were seeded into each well of six-well tissue culture plates. After allowing cells time to attach (6 hours), U1-59 or the vehicle control (PBS) was added at specified concentrations. The plates were irradiated 4 hours later at the doses of 2, 4, 6, 8 Gy. 10 to 14 days after seeding, colonies were stained with crystal violet, the number of colonies containing at least 50 cells was determined and the surviving fractions were calculated. Survival curves were generated after normalizing for cytotoxicity generated by U1-59 alone. Data presented are the mean±SD from at least three independent experiments.
Cell Cycle Analysis Cells were incubated with U1-59 (20 ug/ml) for 48 h, followed 6 Gy radiation. After 24 h, cells were trypsinized and washed with PBS, fixed in 90% ethanol and stored at 4° C. overnight. After remove of ethanol by centrifugation, cells were stained with PI stain buffer (50 ug/ml PI, 100 ug/ml Rnase A, 0.1% Triton X-100). Cells were sorted by FACSCalibur flow cytometer (BD Biosciences, San Jose, Calif., USA). Histogram analysis was performed with FlowJo software (Tree Star Inc., Ashland, Oreg., USA).
Apoptosis Apoptosis were detected using Annexin V/PI kit. Following treatment, a cell suspension containing $1 \times 10^5$ cells in 100 μl staining buffer was incubated with 5 μl Annexin V and PI. Cells were sorted by FACSCalibur flow cytometer (BD Biosciences, San Jose, Calif., USA). Population analysis was performed with FlowJo software.
Immunoblotting Analysis Following treatment, cells were lysed with buffer (50 mM HEPES, pH 7.4, 150 mM NaCl, 0.1% Tween-20, 10% glycerol, 2.5 mM EGTA, 1 mM EDTA, 1 mM DTT, 1 mM PMSF and 10 μg/ml of leupeptin and aprotinin). Protein was quantized using a standard Bradford absorbance assay. Equal amounts of protein were fractionated by SDS-PAGE. Thereafter, proteins were transferred to PVDF membrane and analyzed by incubation with the appropriate primary antibody. Proteins were detected via incubation with HRP-conjugated secondary antibodies and ECL chemiluminescence detection system. The NIH ImageJ program was used to measure densitometry of the western bands. The antibodies used in this study were as follows: HER3, AKT, MAPK, horseradish peroxidase-conjugated goat-anti-rabbit IgG and goat-anti-mouse IgG were purchased from Santa Cruz Biotechnology Inc. (Santa Cruz, Calif., USA). p-HER3 (Tyr1289), p-AKT and p-MAPK were obtained from Cell Signaling Technology (Beverly, Mass., USA). α-tubulin was from Calbiochem (San Diego, Calif., USA).
Immunofluorescence Assay Approximately $2 \times 10^3$ cells were seeded on a four-well glass chamber slide (Nalgene Nunc, Naperville, Ill., USA). Forty-eight hours later, cells were washed 3 times with PBS and fixed with 2% formaldehyde for 15 min at room temperature. Cells were incubated in ice-cold 100% methanol for 10 min at −20° C. and blocked with 5% normal serum in PBS with 0.3% Triton X100 solution for 1 h at room temperature and incubated with p-HER3 or λ-H2AX antibody overnight at 4° C. Next, cells were incubated with FITC-conjugated appropriate secondary antibody in PBS containing 0.3% Triton X100 and 1% BSA for 2 h. Slides were mounted using ProLong gold with DAPI (Invitrogen). Photographs were captured by confocal microscopy or fluorescence microscopy.
Mouse Xenograft Model Athymic nude mice (4- to 6-week old; male) were obtained from the Harlan Laboratories (Indianapolis, Ind., USA). All animal procedures and maintenance were conducted in accordance with the institutional guidelines of the University of Wisconsin. Cells were injected bilaterally in the dorsal flanks of the mice at day 0 ($2 \times 10^6$ cells). Once tumours reached expected volumes, Mice were single or fractionated dosed-treated with 1) IgG, 2) U1-59, 3) radiation or 4) the combination. Measurements were evaluated by digital calipers and calculated by the formula $(\pi)/6 \times$(large diameter)×(small diameter).
Immunohistochemistry Xenograft Tumours were Fixed in Neutral Formalin and Embedded in Paraffin Immunohistochemical staining was performed for PCNA, p-MAPK, p-AKT, p-S6 and γ-H2AX. In brief, specimen was deparaffinized and rehydrated routinely, following antigene retrieval by citrate buffer for 15 mins at 98° C. in water bath, incubation in 3% hydrogen peroxide for 10 minutes, 3% BSA blocking for 30 min. Staining were performed as below: incubation in primary antibody diluted in recommended antibody diluents at 4° C. overnight, incubation in biotinylated secondary antibody for 30 minutes at room temperature, peroxidase visualization using Dakocytomation Liquid DAB+Substrate Chromogen System, Counterstain in Hematoxylin, routine Dehydrate and Clear, mounting with coverslip.

Statistical Analysis

Xenograft tumour growths were graphed and analyzed using GraphPad Prism 5 (GraphPad, San Diego, Calif.).

Results

HER3 is Expressed in Multiple Solid Tumour Cell Lines

Human epidermal growth factor receptor 3 (HER3) is a key dimerization partner for the HER family and activates oncogenic signaling pathways. Its overexpression in many solid tumours has been linked to poor prognosis. In FIG. 1A we charactered 15 cell lines derived from non-small cell lung carcinoma (H226, H292, H358, H520 and A549), colorectal carcinoma (Caco2, SW48, LS180, Lovo and HCT116) and head and neck squamous cell carcinoma (SCC1, SCC6, SCC11A, SCC38 and SCC1483) for the expression of both HER3 and p-HER3. Both HNSCC and NSCLC cell lines contain activated HER3 suggesting that HER3 may be enhancing their tumourigenic phenotype.

U1-59 can Inhibit Basal Activity of HER3 and Radiation-Induced Activation of HER3

HER3 lacks intrinsic tyrosine kinase activity. However, upon binding to multiple ligands, such as heregulin (neuregulin-1), HER3 can form heterodimers with other HER family member receptors to initiate the activation of multiple signaling pathways that strongly influence cell proliferation and survival. U1-59 is a fully humanized monoclonal antibody that binds to and inactivates HER3 oncogenic signaling pathways. In FIG. 1B, we demonstrate that treatment of multiple HNSCC and NSCLC cell lines with escalating doses of U1-59 can successfully inhibit the activation of both HER3 and AKT (FIG. 1B). In addition, using immunoblotting and immunofluorescence assays, we found that radiation treatment of the HNSCC cell line SCC6 and the NSCLC cell line H226 increased activated forms of HER3 (FIGS. 2A, 2C, 2D, and 2F). The transient activation of HER3 after radiation treatment was also accompanied by an increase in activation of both ERK and AKT in both SCC6 and H226 cell lines (FIGS. 2A and 2D). In FIGS. 2B and 2E we demonstrate that radiation can lead to the continual activation of HER3, AKT, and ERK in both SCC6 and H226 cell lines both 24 and 48 hours post radiation treatment. We subsequently demonstrate that the pre-incubation of either SCC6 or H226 cell lines with U1-59 for 24 hrs prior to radiation treatment could prevent the radiation-induced activation of HER3, ERK, and AKT (FIGS. 2A, 2C, 2D, and 2F). Additionally, U1-59 could lead to the continued inhibition HER3, ERK, and AKT activation at both 24 and 48 hours post radiation treatment (FIGS. 2B and 2E). Collectively, these data suggest that pre-incubation of cells with U1-59 prior to radiation treatment can prevent radiation induced activation of cell survival and proliferation pathways.

U1-59 can Radiosensitize HNSCC and NSCLC Cell Lines In-Vitro

Figure 2:
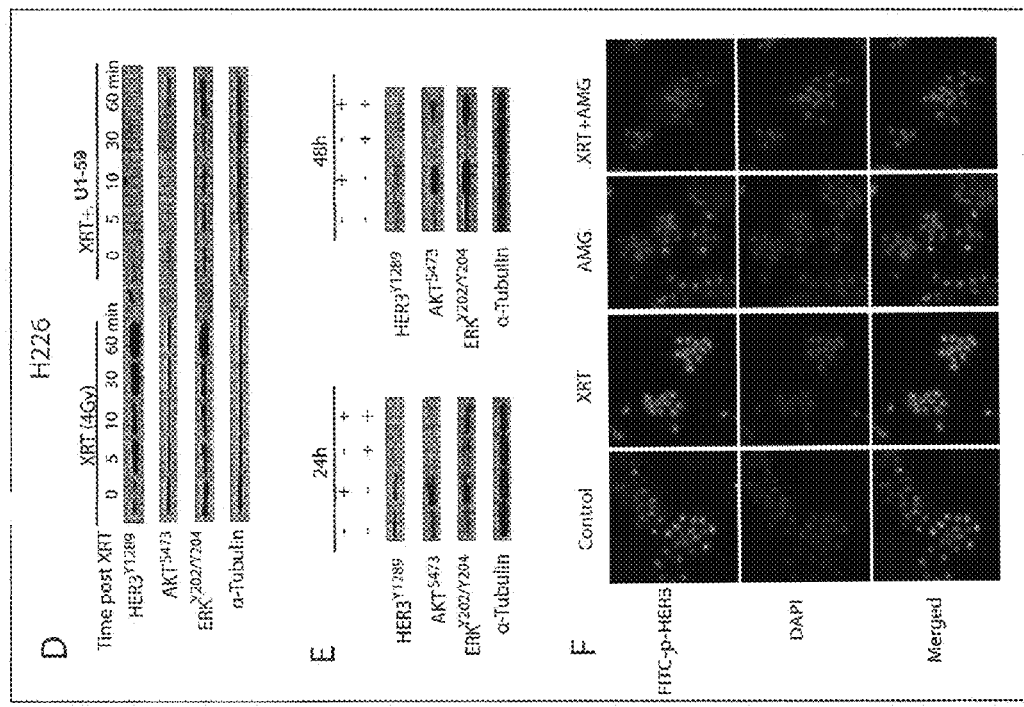
Figure 2:
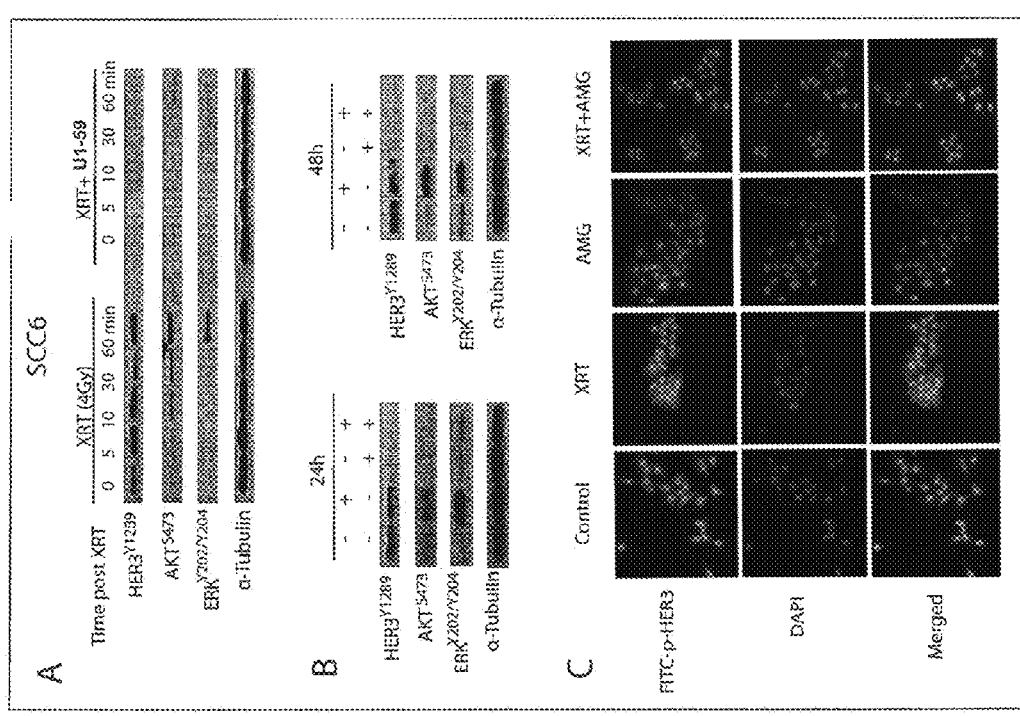
Figure 3:
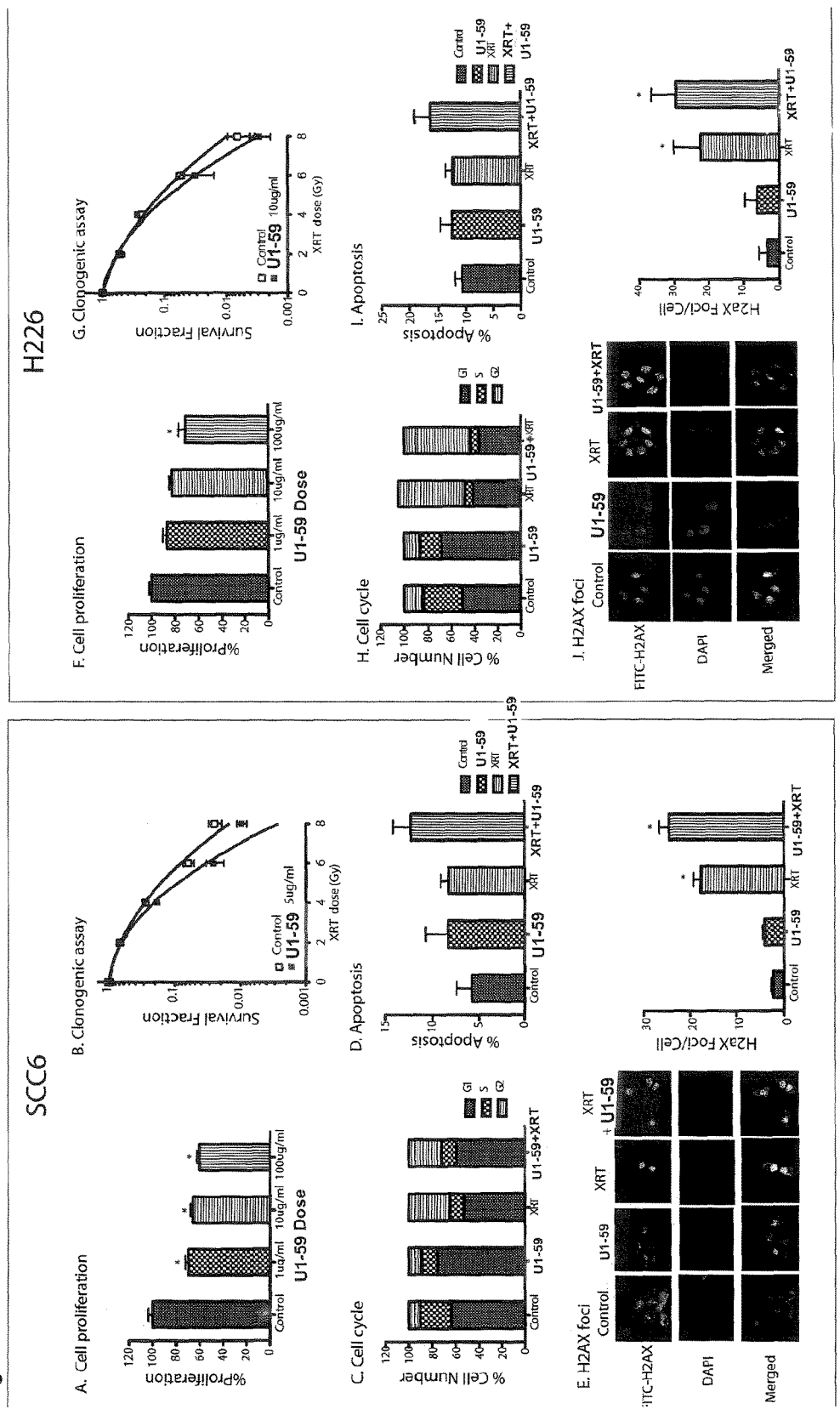

In FIG. 2 we demonstrated that U1-59 could prevent radiation-induced activation of HER3 and subsequent downstream effectors ERK and AKT, therefore we hypothesized that U1-59 could enhance the radiosensitivity of both HNSCC and NSCLC cell lines. First, we demonstrate in FIGS. 3A and 3F that U1-59 can inhibit the growth of both SCC6 and H226 cell lines in a dose-dependent manner. To evaluate the in vitro effect of U1-59 combination with radiation, we conducted clonogenic assays as described in "materials and methods". We pre-incubated both SCC6 and H226 cells with U1-59 for 4 hr, and subsequently subjected cells to radiation with the indicated doses. As shown in FIGS. 3B and 3G, U1-59 increased the slope of the radiation curves, demonstrating a sensitizing effect of U1-59 on both SCC6 and H226 cells in response to radiation. Control curves were exposed to radiation without U1-59 treatment.

U1-59 can Promote Cell Cycle Arrest and Apoptosis in Combination with Radiation Treatment In-vitro We further hypothesized that U1-59 may also enhance HNSCC and NSCLC cell lines to radiation induced cell cycle arrest and apoptosis. To study this we pre-incubated both SCC6 and H226 cells with U1-59 for 48 h followed by exposure to 6 Gy radiation. 24 h post radiation we analyzed the cell cycle phase distribution and apoptotic levels by PI and annexin V staining. As shown in FIGS. 3C and 3H U1-59 pre-treated cells demonstrated a G1 phase arrest, while radiation treated cells demonstrated a G2 phase arrest as compared to control cells. We observe a decrease in S-phase with either treatment. It is well known that cells in G1 phase are more sensitive to radiation treatment, while S-phase cells are more resistant. Therefore we demonstrate through Annexin V staining that apoptosis is indeed enhanced in radiation treated cells pre-incubated with U1-59 (FIGS. 3D and 3I), suggesting that the G1 phase arrest induced by U1-59 may have promoted the radiosentitivy of both SCC6 and H226. In addition, we further show an enhanced level of DNA double strand breaks via γ-H2AX staining in SCC6 and H226 cells pre-treated with U1-59 prior to radiation (FIGS. 3E and 3J). Overall, these data demonstrate the enhanced antitumour effect of U1-59 in combination with radiation.

Figure 4A:
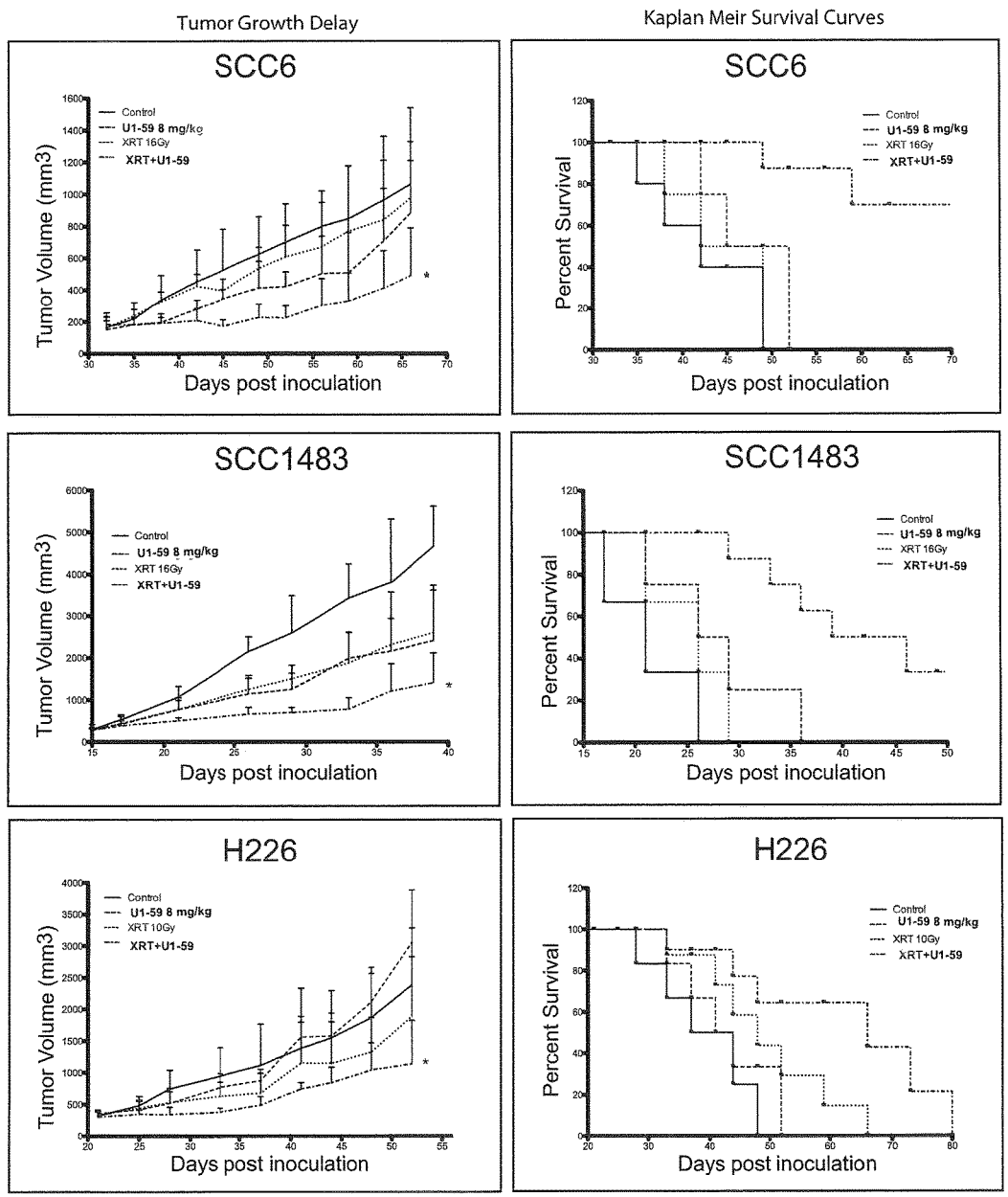
Figure 4B:
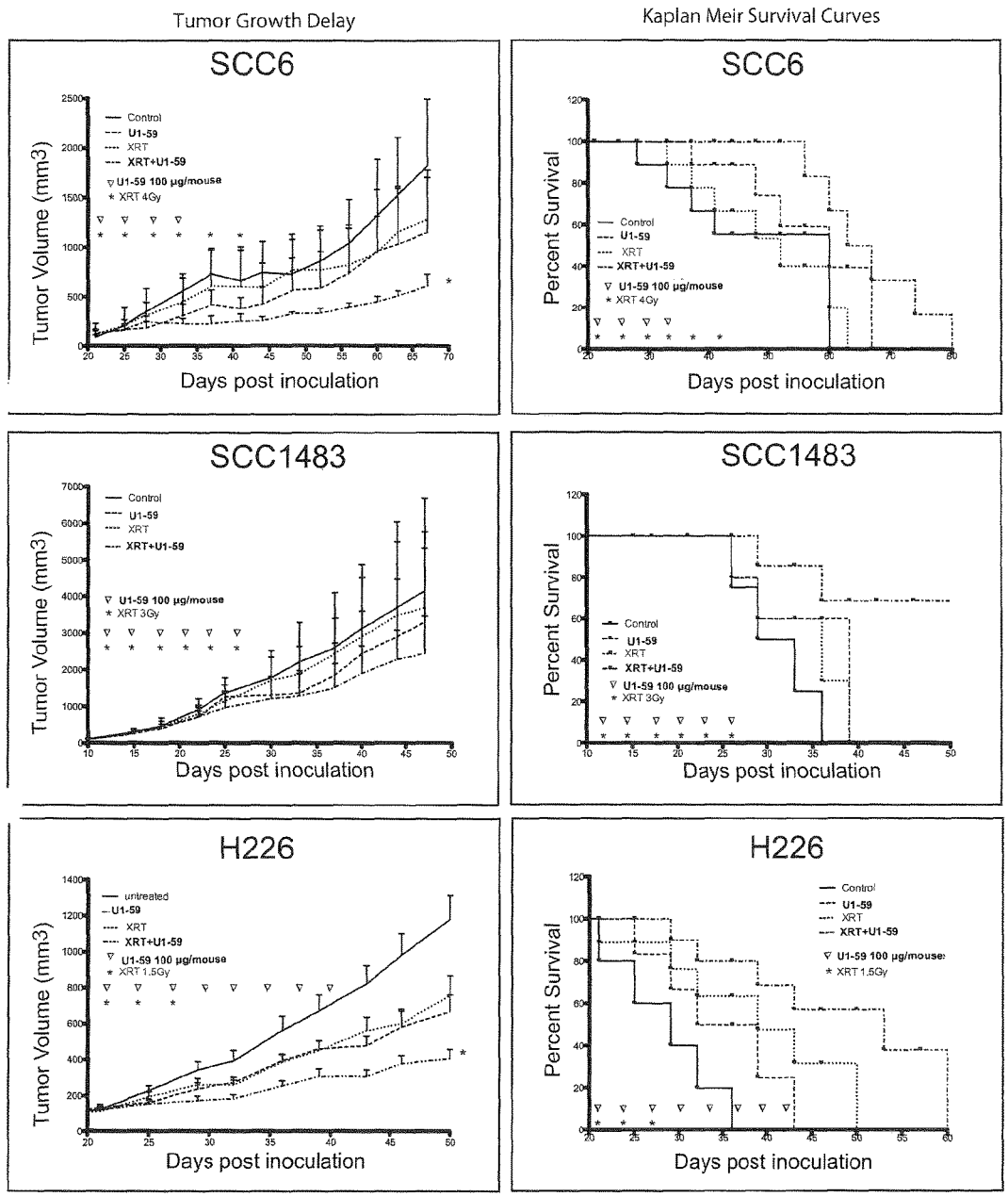

U1-59 in Combination with Radiation can have Antitumour Effects in HNSCC and NSCLC Mouse Tumour Xenografts To further evaluate the efficacy of radiotherapy combined with U1-59, we inoculated SCC6, SCC1483 and H226 cell lines into athymic mice. Once tumours reached 100-200 mm$^3$ tumours were divided up for both single and fractionated doses of radiation. In the single dose treated group, xenograft mice were administered with IgG, U1-59 (8 mg/kg), radiation (XRT16 Gy or XRT10 Gy) or a combination of both (FIG. 4A). In fractionated treated group, xenograft mice were administered with IgG, U1-59 (100 ug/mouse), radiation (twice a week at indicated doses), or combination (FIG. 4B). All three xenografts models demonstrated a marked reduction in tumour volume when treated with both U1-59 in combination with either a single dose or fractionated dose of radiation as compared to single therapy treated mice or IgG control treated mice. Additionally, xenografts treated with both U1-59 and either a single or fractionated dose of radiation demonstrate a clear survival advantage as depicted via Kaplan Meir survival curve analysis.

To validate that U1-59 could effectively inhibit the activation of HER3 in-vivo, we isolated protein from various tumours from each treatment group and performed western blot analysis for both total and activated forms of HER3. In FIG. 5A we demonstrate that tumours isolated from mice treated with U1-59 alone or U1-59 in combination with a single dose of radiation have lower levels of HER3 activation. In SCC1483 and H226 xenograft models U1-59 treated tumours also contained lower total amounts of HER3 protein (FIG. 5A), something that was not observed in these cell lines treated with U1-59 in-vitro. Additionally, at least one of the two tumours isolated from each xenograft model in FIG. 5A demonstrated a clear activation of HER3 upon a single dose of radiation, which was blocked in the U1-59 treated tumours. In FIG. 5B we further demonstrate that U1-59 treated tumours in combination with fractionated doses of radiation also contained reduced levels of activated and total levels of HER3; activation of HER3 by fractionated doses of radiation was also blocked by U1-59 as well. Collectively, xenograft tumours treated with both U1-59 in combination with either a single dose or fractionated doses of radiation demonstrate a clear growth delay with marked reduction in tumour volumes as compared to controls or either treatment alone, suggesting that the loss of both activated and total levels of HER3 expression may radio-sensitize HNSCC and NSCLC tumours.

Figure 6:
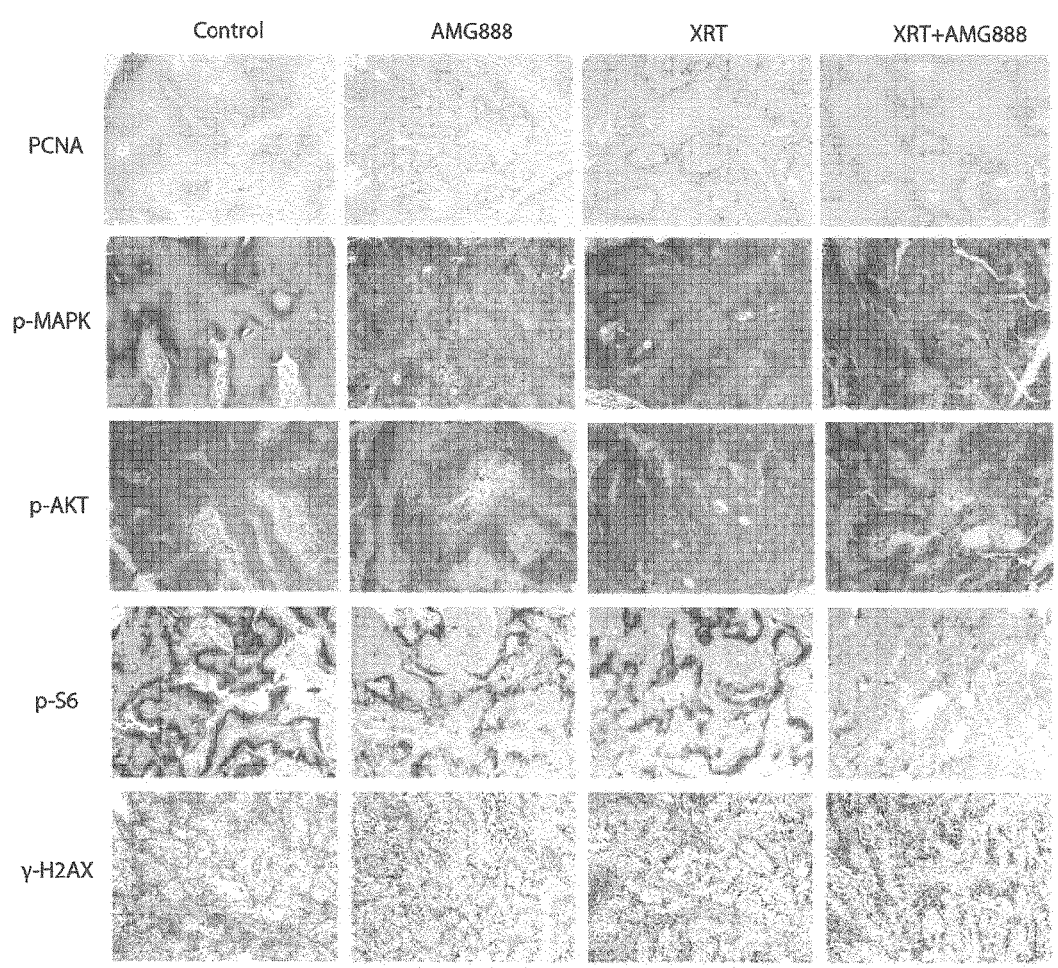

U1-59 in Combination with Radiation can Prevent the Activation of Cell Survival Signals and Enhance DNA Damage In-vivo To further analyze the growth inhibitory effects of U1-59 in combination with radiation treatment, we analyzed the activation of ERK, AKT, S6 kinase, and γ-H2AX in SCC6 treated tumours via immunohistochemistry (FIG. 6). We demonstrate that SCC6 cells treated with both U1-59 and a single dose of radiation can have lower activation levels of the downstream effector molecules ERK, AKT, and S6 kinase. Additionally, U1-59 treated tumours demonstrated a decreased level of PCNA positive cells. Finally, increased levels of γ-H2AX were found in SCC6 tumours treated with both U1-59 and radiation. Overall, these data indicate that U1-59 in combination with radiation can efficiently inhibit cell survival and proliferation pathways, in addition to enhancing DNA damage. These data provide mechanistic evidence for the enhanced antitumour effect of U1-59 combined with radiation in vivo.

The results of these experiments indicate that the combination of U1-59 and radiation had a strong impact on tumour growth in studies using single dose or fractionated dosing of radiation. Tumour analysis indicated that radiation treatment activated HER3 in vivo and U1-59 could abrogate this activation. Collectively our findings in vitro and in vivo indicate that U1-59 in combination with radiation has an impact on cell and tumour growth by delaying cell cycle progression, increasing apoptosis and increasing DNA damage. These findings indicate that HER3 may play an important role in response to radiation therapy and blocking its activity may be of strong therapeutic benefit in human tumours.

Table of CDR Sequences

| Ab chain | Pat. ID: | CDR1 | CDR2 | CDR3 |
|---|---|---|---|---|
| heavy | U1-1 | GGSINSGDYYWS (SEQ ID NO: 235) | YIYYSGSTYYNPSLKS (SEQ ID NO: 236) | ADYDFWSGYFDY (SEQ ID NO: 237) |
| light | | RASQGIRNDLG (SEQ ID NO: 238) | AASSLQS (SEQ ID NO: 239) | LQHNSYPWT (SEQ ID NO: 240) |
| heavy | U1-2 | GGSISSGDYYWS (SEQ ID NO: 241) | YIYYSGSTYYNPSLRS (SEQ ID NO: 242) | ADYDFWSGYFDY (SEQ ID NO: 243) |
| light | | RASQGIRNDLG (SEQ ID NO: 244) | AASSLQS (SEQ ID NO: 245) | LQHNGYPWT (SEQ ID NO: 246) |
| heavy | U1-3 | GGSISSGGYYWS (SEQ ID NO: 247) | YIYYSGSTYYNPSLKS (SEQ ID NO: 248) | DGYDSSGYYHGYFDY (SEQ ID NO: 249) |
| light | | KSSQSVLYSSNNKNYLA (SEQ ID NO: 250) | WASTRES (SEQ ID NO: 251) | QQYYSTPLT (SEQ ID NO: 252) |
| heavy | U1-4 | GGSISSGDYYWS (SEQ ID NO: 253) | YIYYSGSTYYNPSLKS (SEQ ID NO: 254) | ADYDFWSGYFDY (SEQ ID NO: 255) |
| light | | RASQGIRNDLG (SEQ ID NO: 256) | AASSLQS (SEQ ID NO: 257) | LQHNYPWT (SEQ ID NO: 258) |
| heavy | U1-5 | GGSISSGDYYWS (SEQ ID NO: 259) | YIYYSGSTYYNPSLKS (SEQ ID NO: 260) | ADYDFWSGYFDY (SEQ ID NO: 261) |
| light | | RASQGIRNDLG (SEQ ID NO: 262) | AASSLQS (SEQ ID NO: 263) | LQHNTYPWT (SEQ ID NO: 264) |
| heavy | U1-6 | GGSISSGDYYWS (SEQ ID NO: 265) | YIYYSGSTYYNPSLKS (SEQ ID NO: 266) | ADYDFWSGYFDY (SEQ ID NO: 267) |
| light | | RASQGIRNDLG (SEQ ID NO: 268) | AASSLQS (SEQ ID NO: 269) | LQHNNYPWT (SEQ ID NO: 270) |
| heavy | U1-7 | GGSISSGDYYWS (SEQ ID NO: 271) | YIYYSGSTYYNPSLKS (SEQ ID NO: 272) | ADYDFWSGYFDY (SEQ ID NO: 273) |
| light | | RASQDIRNDLG (SEQ ID NO: 274) | AASSLQS (SEQ ID NO: 275) | LQHNSYPWT (SEQ ID NO: 276) |
| heavy | U1-8 | GYTLTELSMY (SEQ ID NO: 277) | GFDPEDGETIYAQKFQG (SEQ ID NO: 278) | GWNYVFDY (SEQ ID NO: 279) |
| light | | RSSQSLLBSNGYNYLD (SEQ ID NO: 280) | LDSHRAS (SEQ ID NO: 281) | MQALQTPLT (SEQ ID NO: 282) |
| heavy | U1-9 | GGSISSGDYYWS (SEQ ID NO: 283) | YIYYSGSTYYNPSLKS (SEQ ID NO: 284) | ADYDFWNGYFDY (SEQ ID NO: 285) |
| light | | RASQDIRMDLG (SEQ ID NO: 286) | AASSLQS (SEQ ID NO: 287) | LQHNSYPWT (SEQ ID NO: 288) |
| heavy | U1-10 | GGSISSGDYYWS (SEQ ID NO: 289) | YIYYSGSTYYNPSLKS (SEQ ID NO: 290) | ADYDFWSGYFDY (SEQ ID NO: 291) |
| light | | RASQGIRNDLG (SEQ ID NO: 292) | AASSLQS (SEQ ID NO: 293) | LQHNNYPWT (SEQ ID NO: 294) |
| heavy | U1-11 | GGSISSGDYYWS (SEQ ID NO: 295) | YIYYSGSTYYNPSLKS (SEQ ID NO: 296) | ADYDFWSGYFDY (SEQ ID NO: 297) |
| light | | RASQGIRNDLG (SEQ ID NO: 298) | AASSLQS (SEQ ID NO: 299) | LQHNTYPWT (SEQ ID NO: 300) |
| heavy | U1-12 | GGSISSGDYYWS (SEQ ID NO: 301) | YIYYSGSTYYNPSLKS (SEQ ID NO: 302) | ADYDFWSGYFDY (SEQ ID NO: 303) |
| light | | RASQGIRNDLG (SEQ ID NO: 304) | AASSLQS (SEQ ID NO: 305) | LQHNNYPWT (SEQ ID NO: 306) |

Table of CDR Sequences

| Ab chain | Pat. ID: | CDR1 | CDR2 | CDR3 |
|---|---|---|---|---|
| heavy | U1-13 | GGSISSGGYYWS (SEQ ID NO: 307) | YIYYSGSTYYNPSLKS (SEQ ID NO: 308) | EDDGEDV (SEQ ID NO: 309) |
| light | | RSSQSLLHSNGYNYLE (SEQ ID NO: 310) | LGSNRAS (SEQ ID NO: 311) | MQALQTPIT (SEQ ID NO: 312) |
| heavy | U1-14 | GGSISSGDYYWS (SEQ ID NO: 313) | YIYYSGSTYYNPSLKS (SEQ ID NO: 314) | ADYDFWSGYFDY (SEQ ID NO: 315) |
| light | | RASQGIRNDLG (SEQ ID NO: 316) | AASSLQS (SEQ ID NO: 317) | LQHNTYPWT (SEQ ID NO: 318) |
| heavy | U1-15 | GGSVSSGGYYWS (SEQ ID NO: 319) | YIYYSGSTNYNPSLKS (SEQ ID NO: 320) | DGDVDTAMVDAFDI (SEQ ID NO: 321) |
| light | | RASQSLSGNYLA (SEQ ID NO: 322) | GASSRAT (SEQ ID NO: 323) | QQYDRSPLT (SEQ ID NO: 324) |
| heavy | U1-16 | GGSISSGDYYWS (SEQ ID NO: 325) | YIYYSGSTYYNPSLKS (SEQ ID NO: 326) | ADYDFWSGYFDY (SEQ ID NO: 327) |
| light | | RASQGIRNDLG (SEQ ID NO: 328) | AASSLQS (SEQ ID NO: 329) | LQHNSYPWT (SEQ ID NO: 330) |
| heavy | U1-17 | GGSISSGDYYWS (SEQ ID NO: 331) | YIYYSGSTYYNSSLKS (SEQ ID NO: 332) | ADYDFWSGYFDY (SEQ ID NO: 333) |
| light | | RASQGIRNDLG (SEQ ID NO: 334) | AASSLQS (SEQ ID NO: 335) | LQHNSYPWT (SEQ ID NO: 336) |
| heavy | U1-18 | GGSISSGDYYWS (SEQ ID NO: 337) | YIYYSGSTYYNPSLKS (SEQ ID NO: 338) | ADYDFWSGYFDY (SEQ ID NO: 339) |
| light | | RASQGIRNDLG (SEQ ID NO: 340) | AASSLQS (SEQ ID NO: 341) | LQHNSYPWT (SEQ ID NO: 342) |
| heavy | U1-19 | GGSISSGDYYWS (SEQ ID NO: 343) | YIYYSGSTYYNPSLKS (SEQ ID NO: 344) | GDYDFWSGEFDY (SEQ ID NO: 345) |
| light | | | sequence not available | |
| heavy | U1-20 | GGSISSGGYYWS (SEQ ID NO: 346) | YIYDSGSTYYNPSLKS (SEQ ID NO: 347) | DQGQDGYSYGYGYYYGMDV (SEQ ID NO: 348) |
| light | | QASQDISNYLN (SEQ ID NO: 349) | VASNLET (SEQ ID NO: 350) | QQCDNLPLT (SEQ ID NO: 351) |
| heavy | U1-21 | GGSISSGDYYWS (SEQ ID NO: 352) | YIYYSGSTYYNPSLKS (SEQ ID NO: 353) | ADYDFWSGYFDY (SEQ ID NO: 354) |
| light | | RASQDIRNDLG (SEQ ID NO: 355) | AASSLQS (SEQ ID NO: 356) | LQHNSYPWT (SEQ ID NO: 357) |
| heavy | U1-22 | GGSISSGDYYWS (SEQ ID NO: 358) | YIYYSGSTYYNPSLKS (SEQ ID NO: 359) | ADYDFWSGYFDY (SEQ ID NO: 360) |
| light | | RASQGIRNDLG (SEQ ID NO: 361) | AASSLQN (SEQ ID NO: 362) | LQHNSYPWT (SEQ ID NO: 363) |
| heavy | U1-23 | GGSISSGDYYWS (SEQ ID NO: 364) | YIYYSGSTYYNPSLKS (SEQ ID NO: 365) | ADYDFWSGYFDY (SEQ ID NO: 366) |
| light | | RASQGIRNDLG (SEQ ID NO: 367) | AASSLQS (SEQ ID NO: 368) | LQHNSYPWT (SEQ ID NO: 369) |
| heavy | U1-24 | GGSISSGDYYWS (SEQ ID NO: 370) | YIYYSGSTYYNPSLKS (SEQ ID NO: 371) | ADYDFWNGYFDY (SEQ ID NO: 372) |
| light | | RASQGIRNDLG (SEQ ID NO: 373) | AASSLQS (SEQ ID NO: 374) | LQHNSYPWT (SEQ ID NO: 375) |
| heavy | U1-25 | GGSISSGDYYWS (SEQ ID NO: 376) | YIYYSGSTYYNPSLKS (SEQ ID NO: 377) | ADYDFWSGYFDY (SEQ ID NO: 378) |
| light | | RASQGIRNDLG (SEQ ID NO: 379) | AASSLQN (SEQ ID NO: 380) | LQHNSYPWT (SEQ ID NO: 381) |
| heavy | U1-26 | GGSISSGDYYWS (SEQ ID NO: 382) | YIYYSGSTYYNPSLKS (SEQ ID NO: 383) | ADYDFWSGYFDF (SEQ ID NO: 384) |
| light | | RASQGIRNDLG (SEQ ID NO: 385) | AASSLQS (SEQ ID NO: 386) | LQHNGYPWT (SEQ ID NO: 387) |
| heavy | U1-27 | GGSISSGDYYWS (SEQ ID NO: 388) | YIYYSGSTYYNPSLKS (SEQ ID NO: 389) | ADYDFWSGYFDF (SEQ ID NO: 390) |
| light | | RASQGIRNDLG (SEQ ID NO: 391) | AASSLQS (SEQ ID NO: 392) | LQHNGYPWT (SEQ ID NO: 393) |
| heavy | U1-28 | GGSISSGDYYWS (SEQ ID NO: 394) | YIYYSGSTYYNPSLKS (SEQ ID NO: 395) | ADYDFWSGYFDS (SEQ ID NO: 396) |
| light | | RASQGIRNDLG (SEQ ID NO: 397) | AASSLQS (SEQ ID NO: 398) | LQHNGYPWT (SEQ ID NO: 399) |
| heavy | U1-29 | GFTFNSYDMH (SEQ ID NO: 400) | VIWYDGSNKYYADSVKS (SEQ ID NO: 401) | DRLCTNGVCYEDYGMDV (SEQ ID NO: 402) |
| light | | QASQDISNYLN (SEQ ID NO: 403) | DASNLET (SEQ ID NO: 404) | QHYDTLPLT (SEQ ID NO: 405) |
| heavy | U1-30 | GGSISSGDYYWS (SEQ ID NO: 406) | YIYYSGTTYYNPSLKS (SEQ ID NO: 407) | ADYDFWSGYFDY (SEQ ID NO: 408) |
| light | | RAGQGIRNDLG (SEQ ID NO: 409) | AASSLQS (SEQ ID NO: 410) | LQHNSYPWT (SEQ ID NO: 411) |
| heavy | U1-31 | GYTFTNYGIS (SEQ ID NO: 412) | WISAYDGYRNYAQKLQG (SEQ ID NO: 413) | DVQDYGDYDYFDY (SEQ ID NO: 414) |
| light | | RASQSISSYLN (SEQ ID NO: 415) | AASSLQS (SEQ ID NO: 416) | QQSYSTPIT (SEQ ID NO: 417) |

Table of CDR Sequences

| Ab chain | Pat. ID: | CDR1 | CDR2 | CDR3 |
|---|---|---|---|---|
| heavy | U1-32 | GGSISSGDYYWS (SEQ ID NO: 418) | YIYYSGTTYYNPSLKS (SEQ ID NO: 419) | ADYDFWSGYFDY (SEQ ID NO: 420) |
| light | | RAGQGIRKDLG (SEQ ID NO: 421) | AASSLQS (SEQ ID NO: 422) | LQHNSYPWT (SEQ ID NO: 423) |
| heavy | U1-33 | GGSISSGDYYWS (SEQ ID NO: 424) | YIYYSGSTYYNPSLKS (SEQ ID NO: 425) | ADYDFWSGHFDC (SEQ ID NO: 426) |
| light | | RASQGIRDDLG (SEQ ID NO: 427) | AESSLQS (SEQ ID NO: 428) | LQHHSYPWT (SEQ ID NO: 429) |
| heavy | U1-34 | GYTFTNYGIS (SEQ ID NO: 430) | WISAYDGYRNYAQKLQG (SEQ ID NO: 431) | DVQDYGDYDYFDY (SEQ ID NO: 432) |
| light | | RASQSISSYLN (SEQ ID NO: 433) | AASSLQS (SEQ ID NO: 434) | QQSYSTPIT (SEQ ID NO: 435) |
| heavy | U1-35 | GFTFSDYYMS (SEQ ID NO: 436) | YISSSGNNIYHADSVKG (SEQ ID NO: 437) | ERYSGYDDPDGFDI (SEQ ID NO: 438) |
| light | | QASQDISNYLS (SEQ ID NO: 439) | DASNLET (SEQ ID NO: 440) | QQYDNPPCS (SEQ ID NO: 441) |
| heavy | U1-36 | GGSISSGYYYWS (SEQ ID NO: 442) | YIYYSGTTYYNPSFKS (SEQ ID NO: 443) | ADYDFWSGHFDY (SEQ ID NO: 444) |
| light | | RASQGIRNDLG (SEQ ID NO: 445) | AASSLQS (SEQ ID NO: 446) | LQHNSYPWT (SEQ ID NO: 447) |
| heavy | U1-37 | GYTFTSYGIS (SEQ ID NO: 448) | WISAYDGHTNYAQKLQG (SEQ ID NO: 449) | DPHDYSNYEAFDF (SEQ ID NO: 450) |
| light | | RASQSISSYLN (SEQ ID NO: 451) | AASSLQS (SEQ ID NO: 452) | QQSYSTPIT (SEQ ID NO: 453) |
| heavy | U1-38 | GFSLSTSGVGVG (SEQ ID NO: 454) | LIYWNDDKRYSPSLKS (SEQ ID NO: 455) | RDEVRGFDY (SEQ ID NO: 456) |
| light | | RSSQSLVYSDGYTYLH (SEQ ID NO: 457) | KVSNWDS (SEQ ID NO: 458) | MQGAHWPIT (SEQ ID NO: 459) |
| heavy | U1-39 | GFTVSSNYMS (SEQ ID NO: 460) | VIYSGGSTYYADSVKG (SEQ ID NO: 461) | GQWLDV (SEQ ID NO: 462) |
| light | | RSSQSLLHSNGYNYLD (SEQ ID NO: 463) | LGFHRAS (SEQ ID NO: 464) | RQALQTPLT (SEQ ID NO: 465) |
| heavy | U1-40 | GGSISSGGYYWS (SEQ ID NO: 466) | YIYYSGSTYYNPSLKS (SEQ ID NO: 467) | DRELELYYYYGMDV (SEQ ID NO: 468) |
| light | | RSSQSLLYSNGYNYLD (SEQ ID NO: 469) | LGSNRAS (SEQ ID NO: 470) | MQALQTPLT (SEQ ID NO: 471) |
| heavy | U1-41 | GGSISSGGYYWS (SEQ ID NO: 472) | YIYYSGSTYYNPSLKS (SEQ ID NO: 473) | DRELEGYSNYYGVDV (SEQ ID NO: 474) |
| light | | RASQAISNYLN (SEQ ID NO: 475) | AASSLQS (SEQ ID NO: 476) | QQNNSLPIT (SEQ ID NO: 477) |
| heavy | U1-42 | GYSFTSYWIG (SEQ ID NO: 478) | IIYPGDSDTRYSPSFQG (SEQ ID NO: 479) | HENYGDYNY (SEQ ID NO: 480) |
| light | | RASQSIRSYLN (SEQ ID NO: 481) | AASSLQS (SEQ ID NO: 482) | QQSNGSPLT (SEQ ID NO: 483) |
| heavy | U1-43 | GGSISSGGYYWS (SEQ ID NO: 484) | YIYYSGSTYYNPSLRS (SEQ ID NO: 485) | DREREWDDYGDPQGMDV (SEQ ID NO: 486) |
| light | | RASQSISSYLH (SEQ ID NO: 487) | AASSLQS (SEQ ID NO: 488) | QQSYSNPLT (SEQ ID NO: 489) |
| heavy | U1-44 | GYSFTSYWIG (SEQ ID NO: 490) | IIWPGDSDTIYSPSFQG (SEQ ID NO: 491) | HENYGDYNY (SEQ ID NO: 492) |
| light | | RASQSIRSYLN (SEQ ID NO: 493) | AASSLQS (SEQ ID NO: 494) | QQSISSPLT (SEQ ID NO: 495) |
| heavy | U1-45 | GYTFTSYDIN (SEQ ID NO: 496) | WMNPNSGDTGYAQVFQG (SEQ ID NO: 497) | FGDLPYDYSYYEWFDP (SEQ ID NO: 498) |
| light | | RASQSISSYLN (SEQ ID NO: 499) | AASSLQS (SEQ ID NO: 500) | QQSYSTPLT (SEQ ID NO: 501) |
| heavy | U1-46 | GDSVSSNSAAWN (SEQ ID NO: 502) | RTYYRSKWYNDYAVSVKS (SEQ ID NO: 503) | DLYDFWSGYPYYYGMDV (SEQ ID NO: 504) |
| light | | | sequence not available | |
| heavy | U1-47 | GDSVSSNSAAWN (SEQ ID NO: 505) | RTYYRSKWYNDYAVSVKS (SEQ ID NO: 506) | DYYGSGSFYYYYGMDV (SEQ ID NO: 507) |
| light | | RASQSISSYLN (SEQ ID NO: 508) | AASNLQS (SEQ ID NO: 509) | QQSYSTPRT (SEQ ID NO: 510) |
| heavy | U1-48 | GGSISSYYWS (SEQ ID NO: 511) | HIYTSGSTNYNPSLKS (SEQ ID NO: 512) | EAIFGVGPYYYYGMDV (SEQ ID NO: 513) |
| light | | | sequence not available | |
| heavy | U1-49 | GYTFTGYYMH (SEQ ID NO: 514) | WINPNIGGTNCAQKFQG (SEQ ID NO: 515) | GGRYSSSWSYYYYGMDV (SEQ ID NO: 516) |
| light | | KSSQSLLLSDGGTYLY (SEQ ID NO: 517) | EVSNRFS (SEQ ID NO: 518) | MQSMQLPIT (SEQ ID NO: 519) |
| heavy | U1-50 | GGSVSSGGYYWS (SEQ ID NO: 520) | YIYYSGSTNYNPSLKS (SEQ ID NO: 521) | GGDSNYEDYYYYGMDV (SEQ ID NO: 522) |

Table of CDR Sequences

| Ab chain | Pat. ID: | CDR1 | CDR2 | CDR3 |
|---|---|---|---|---|
| light | | RASQSISIYLH (SEQ ID NO: 523) | AASSLQS (SEQ ID NO: 524) | QQSYTSPIT (SEQ ID NO: 525) |
| heavy | U1-51 | GGSISSYYWS (SEQ ID NO: 526) | YIYYSGSTNYNPSLKS (SEQ ID NO: 527) | DSSYYDSSGYYLYYYAMDV (SEQ ID NO: 528) |
| light | | KSSQSVLYSSNNKNYLA (SEQ ID NO: 529) | WASTRES (SEQ ID NO: 530) | QQYYTTPLT (SEQ ID NO: 531) |
| heavy | U1-52 | GGSISSGGYYWS (SEQ ID NO: 532) | NIYYSGSTYYNPSLKS (SEQ ID NO: 533) | GGTGTNYYYYYGMDV (SEQ ID NO: 534) |
| light | | RASQSVSSSYLA (SEQ ID NO: 535) | GASSWAT (SEQ ID NO: 536) | QQYGSSPLT (SEQ ID NO: 537) |
| heavy | U1-53 | GFTFSIYSMN (SEQ ID NO: 538) | YISSSSSTIYYADSVKG (SEQ ID NO: 539) | DRGDFDAFDI (SEQ ID NO: 540) |
| light | | QASQDITNYLN (SEQ ID NO: 541) | DASNLET (SEQ ID NO: 542) | QQCENFPIT (SEQ ID NO: 543) |
| heavy | U1-55.1 | GGSVSSGGYYWN (SEQ ID NO: 544) | YINYSGSTNYNPSLKS (SEQ ID NO: 545) | DRELELYYYYYGMDV (SEQ ID NO: 546) |
| light | | will be same as U1-55 | | |
| heavy | U1-55 | will be same as U1-55.1 | | |
| light | | RSSQSLLYSNGYKYKLD (SEQ ID NO: 547) | LGSNRAS (SEQ ID NO: 548) | MQALQTPIT (SEQ ID NO: 549) |
| heavy | U1-57.1 | will be same as U1-57 | | |
| light | | RSSQSLLYSNGYKYLD (SEQ ID NO: 550) | LGSNRAS (SEQ ID NO: 551) | MQALQTPIT (SEQ ID NO: 552) |
| heavy | U1-57 | GGSVSSGGYYWN (SEQ ID NO: 553) | YINYSGSTNYNPSLKS (SEQ ID NO: 554) | DRELELYYYYYGMDV (SEQ ID NO: 555) |
| light | | will be same as U1-57.1 | | |
| heavy | U1-58 | GFTFSSYGMH (SEQ ID NO: 556) | VIWYDGSNKYYADSVKG (SEQ ID NO: 557) | AARLDYYYGMDV (SEQ ID NO: 558) |
| light | | RASQSINSYLN (SEQ ID NO: 559) | GASGLQS (SEQ ID NO: 560) | QQSYSSPLT (SEQ ID NO: 561) |
| heavy | U1-59 | GGSFSGYYWS (SEQ ID NO: 562) | EINHSGSTNYNPSLKS (SEQ ID NO: 563) | DKWTWYFDL (SEQ ID NO: 564) |
| light | | RSSQSVLYSSSNRNYLA (SEQ ID NO: 565) | WASTRES (SEQ ID NO: 566) | QQYYSTPRT (SEQ ID NO: 567) |
| heavy | U1-61.1 | GVSISSGGYYWS (SEQ ID NO: 568) | YIYYSGSTYYNPSLKS (SEQ ID NO: 569) | DSESEYSSSSNYGMDV (SEQ ID NO: 570) |
| light | | RASQTISSYLN (SEQ ID NO: 571) | AASSLQG (SEQ ID NO: 572) | QQSYSNPLT (SEQ ID NO: 573) |
| heavy | U1-61 | GVSISSGGYYWS (SEQ ID NO: 574) | YIYYSGSTYYNPSLKS (SEQ ID NO: 575) | DSESEYSSSSNYGMDV (SEQ ID NO: 576) |
| light | | will be the game as U1-61.1 | | |
| heavy | U1-62 | GYSFTSYWIG (SEQ ID NO: 577) | IIYPGDSDTRYSPSFQG (SEQ ID NO: 578) | QMAGNYYYGMDV (SEQ ID NO: 579) |
| light | | RASQSVISIYLA (SEQ ID NO: 580) | GASSRAT (SEQ ID NO: 581) | QQYGSSPCS (SEQ ID NO: 582) |

The invention claimed is:

1. A method of treating a hyperproliferative disease in a subject comprising administering to the subject an anti-HER-3 antibody or an antigen-binding fragment thereof in combination with radiation treatment,
    wherein the radiation treatment comprises X-ray radiation,
    wherein the anti-HER-3 antibody or an antigen-binding fragment thereof comprises a heavy chain variable region with an amino acid sequence comprising SEQ ID NO:70 and a light chain variable region with an amino acid sequence comprising SEQ ID NO:72,
    wherein the hyperproliferative disease is head and neck cancer, and
    wherein the anti-HER-3 antibody or antigen-binding fragment thereof is administered before the X-ray radiation and sensitizes the head and neck cancer to the X-ray radiation.

2. The method of claim 1, wherein the anti-HER-3 antibody is a monoclonal antibody, a recombinant antibody, a human antibody, a multispecific antibody, or an antigen-binding fragment thereof.

3. The method of claim 1, wherein said antigen-binding fragment of the anti-HER-3 antibody is a Fab fragment, a Fab' fragment, a F(ab')$_2$ fragment, a Fv fragment, a diabody, or a single chain antibody molecule.

4. The method of claim 1, wherein said anti-HER-3 antibody is coupled to an effector group and/or labelling group.

5. The method of claim 4, wherein said effector group is a radioisotope, a radionuclide, a toxin, a therapeutic group, and/or a chemotherapeutic group.

6. The method of claim 4, wherein said labelling group is a radioisotope or radionuclide, a fluorescent group, an enzymatic group, a chemiluminescent group, a biotinyl group, or a predetermined polypeptide epitope.

7. The method of claim 1, wherein the head and neck cancer is head and neck squamous cell carcinoma.

8. The method of claim 1, wherein the radiation treatment further comprises brachytherapy, radioisotope therapy, or external beam radiation therapy other than X-ray radiation treatment.

9. The method of claim 1, wherein the radiation treatment is based on a single dose or fractioned dosing of radiation.

10. The method of claim 1, wherein the method comprises administering a further active compound.

11. The method of claim 10, wherein the further active compound comprises a chemotherapeutic compound.

12. The method of claim 1 wherein the anti-HER-3 antibody or antigen-binding fragment thereof is administered 4 hours or 48 hours before the X-ray radiation.

13. The method of claim 12 wherein the X-ray radiation is 10 Gy or 16 Gy.

14. The method of claim 13 wherein the X-ray radiation is fractionated.

15. The method of claim 13 wherein the X-ray radiation is a single dose.

16. A method of treating head and neck cancer in a subject, the method comprising:
    administering to the subject an anti-HER-3 antibody or an antigen-binding fragment thereof, wherein the anti-HER-3 antibody or an antigen-binding fragment thereof comprises a heavy chain variable region with an amino acid sequence comprising SEQ ID NO:70 and a light chain variable region with an amino acid sequence comprising SEQ ID NO:72, and
    subsequently administering to the subject a radiation treatment, the radiation treatment comprising X ray radiation, wherein the anti-HER-3 antibody or antigen-binding fragment thereof sensitizes the head and neck cancer to the X-ray radiation.

17. The method of claim 16 wherein the anti-HER3 antibody or antigen-binding fragment thereof is administered to the subject 4 hours or 48 hours prior to the X-ray radiation.

18. The method of claim 17 wherein the X-ray radiation is 10 Gy or 16 Gy.

19. The method of claim 18 wherein the X-ray radiation is fractionated.

20. The method of claim 18 wherein the X-ray radiation is a single dose.

21. The method of claim 16 wherein the head and neck cancer is head and neck squamous cell carcinoma.

* * * * *

```
                           SEQUENCE LISTING

<160> NUMBER OF SEQ ID NOS: 582

<210> SEQ ID NO 1
<211> LENGTH: 342
<212> TYPE: DNA
<213> ORGANISM: Artificial
<220> FEATURE:
<223> OTHER INFORMATION: Antibody

<400> SEQUENCE: 1
gaggtgcagc tggtggagtc tggaggaggc ttgatccagc ctggggggtc cctgagactc      60
tcctgtgcag cctctgggtt caccgtcagt agcaactaca tgagctgggt ccgccaggct     120
ccagggaagg gctggattg gtctcagtt atttatagcg gtggtagcac atactacgca     180
gactccgtga agggccgatt caccatctcc agagacaatt ccaagaacac gctgtatctt     240
caaatgaaca gcctgagagc cgaggacacg gccgtgtatt actgtgcgag agggcagtgg     300
ctggacgtct ggggccaagg gaccacggtc accgtctcct ca                        342
```

<210> SEQ ID NO 2
<211> LENGTH: 114
<212> TYPE: PRT
<213> ORGANISM: Artificial
<220> FEATURE:
<223> OTHER INFORMATION: Antibody

<400> SEQUENCE: 2

```
Glu Val Gln Leu Val Glu Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Asp Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Gln Trp Leu Asp Val Trp Gly Gln Gly Thr Thr Val Thr Val
            100                 105                 110

Ser Ser
```

<210> SEQ ID NO 3
<211> LENGTH: 336
<212> TYPE: DNA
<213> ORGANISM: Artificial
<220> FEATURE:
<223> OTHER INFORMATION: Antibody

<400> SEQUENCE: 3

```
gatattgtga tgactcagtc tccactctcc ctgcccgtca cccctggaga gccggcctcc      60
atctcctgca ggtcaagtca gagcctcctg catagtaatg gatacaacta tttggattgg     120
tacctgcaga ggccagggca gtctccacaa ctcctgttct atttgggttt tcatcgggcc     180
tccggggtcc ctgacaggtt cagtggcagt ggatcaggca cagattttac actgaaaatc     240
agcagagtgg aggctgagga tgttggggtt tattactgca ggcaagctct acaaactccg     300
ctcactttcg gcggagggac caaggtggag atcaaa                                336
```

<210> SEQ ID NO 4
<211> LENGTH: 112
<212> TYPE: PRT
<213> ORGANISM: Artificial
<220> FEATURE:
<223> OTHER INFORMATION: Antibody

<400> SEQUENCE: 4

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Arg Pro Gly Gln Ser
        35                  40                  45

Pro Gln Leu Leu Phe Tyr Leu Gly Phe His Arg Ala Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Arg Gln Ala
                85                  90                  95

Leu Gln Thr Pro Leu Thr Phe Gly Gly Gly Thr Lys Val Glu Ile Lys
            100                 105                 110
```

<210> SEQ ID NO 5
<211> LENGTH: 374
<212> TYPE: DNA
<213> ORGANISM: Artificial
<220> FEATURE:
<223> OTHER INFORMATION: Antibody

<400> SEQUENCE: 5

```
caggtgcagc tgcaggagtc gggcccagga ctggtgaagc cttcacagac cctgtccctc     60
acctgtactg tctctggtgg ctccatcagc agtggtggtt actactggag ctggatccgc    120
cagcacccag ggaagggcct ggagtggatt gggtacatct attccagtgg gagcacctac    180
tacaacccgt ccctcaagag tcgagttacc atatcagtag acacgtctaa gaaccagttc    240
tccctgaagc tgagctctgt gactgccgcg gacacggccg tgtattactg tgcgagagat    300
agggaactgg aactttacta ctactactac ggtatggacg tctggggcca agggaccacg    360
gtcaccgtct cctc                                                     374
```

<210> SEQ ID NO 6
<211> LENGTH: 124
<212> TYPE: PRT
<213> ORGANISM: Artificial
<220> FEATURE:
<223> OTHER INFORMATION: Antibody

<400> SEQUENCE: 6

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Ser Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120
```

<210> SEQ ID NO 7
<211> LENGTH: 336
<212> TYPE: DNA
<213> ORGANISM: Artificial
<220> FEATURE:
<223> OTHER INFORMATION: Antibody

<400> SEQUENCE: 7

```
gatattgtga tgactcagtc tccactctcc ctgcccgtca cccctggaga gccggcctcc     60
atctcctgca ggtctagtca gagcctcctg tatagtaatg gatacaacta tttggattgg    120
tacctgcaga agccagggca gtctccacag ctcctgatct atttgggttc taatcgggcc    180
```

```
tccggggtcc ctgacaggtt cagtggcagt ggatcaggca cagattttac actgaaaatc        240
agcagagtgg aggctgagga tgttgggatt tattactgca tgcaagctct acaaactccg        300
ctcactttcg gcggagggac caaggtggag atcaaa                                  336
```

<210> SEQ ID NO 8
<211> LENGTH: 112
<212> TYPE: PRT
<213> ORGANISM: Artificial
<220> FEATURE:
<223> OTHER INFORMATION: Antibody

<400> SEQUENCE: 8

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 9
<211> LENGTH: 357
<212> TYPE: DNA
<213> ORGANISM: Artificial
<220> FEATURE:
<223> OTHER INFORMATION: Antibody

<400> SEQUENCE: 9

```
cagatcaccT tgaaggagtc tggtcctacg ctggtgaaac ccacacagac cctcacgctg        60
acctgcacct tctctgggtt ctcactcagc actagtggag tgggtgtggg ctggatccgt       120
cagcccccag gaaaggccct ggactggctt gcactcattt attggaatga tgataagcgc       180
tacagcccat ctctgaagag caggctcacc atcaccaagg acacctccaa aaaccaggtg       240
gtccttacaa tgaccaacat ggatcttgtg gacacagcca catattactg tgtacacaga       300
gacgaagttc gagggtttga ctactgggc cagggaaccc tggtcaccgt ctcctca          357
```

<210> SEQ ID NO 10
<211> LENGTH: 119
<212> TYPE: PRT
<213> ORGANISM: Artificial
<220> FEATURE:
<223> OTHER INFORMATION: Antibody

<400> SEQUENCE: 10

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Asp
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Leu Val Asp Thr Ala Thr Tyr Tyr
                85                  90                  95

Cys Val His Arg Asp Glu Val Arg Gly Phe Asp Tyr Trp Gly Gln Gly
            100                 105                 110

Thr Leu Val Thr Val Ser Ser
            115

<210> SEQ ID NO 11
<211> LENGTH: 336
<212> TYPE: DNA
<213> ORGANISM: Artificial
<220> FEATURE:
<223> OTHER INFORMATION: Antibody

<400> SEQUENCE: 11
gatgttgtga tgactcagtc tccactctcc ctgcccgtca cccttggaca gccggcctcc    60
atctcctgca ggtctagtca aagcctcgta tacagtgatg gatacaccta cttgcattgg   120
tttcagcaga ggccaggcca atctccaagg cgcctatttt ataaggtttc taactgggac   180
tctggggtcc cagacagatt cagcggcagt gggtcaggca ctgatttcac actgaaaatc   240
agcagggtgg aggctgagga tgttggggtt tattactgca tgcaaggtgc acactggccg   300
atcaccttcg gccaagggac acgactggag attaaa                             336

<210> SEQ ID NO 12
<211> LENGTH: 112
<212> TYPE: PRT
<213> ORGANISM: Artificial
<220> FEATURE:
<223> OTHER INFORMATION: Antibody

<400> SEQUENCE: 12

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
                20                  25                  30

Asp Gly Tyr Thr Tyr Leu His Trp Phe Gln Gln Arg Pro Gly Gln Ser
            35                  40                  45

Pro Arg Arg Leu Ile Tyr Lys Val Ser Asn Trp Asp Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ala His Trp Pro Ile Thr Phe Gly Gln Gly Thr Arg Leu Glu Ile Lys
            100                 105                 110

<210> SEQ ID NO 13
<211> LENGTH: 374
<212> TYPE: DNA
<213> ORGANISM: Artificial
<220> FEATURE:
<223> OTHER INFORMATION: Antibody

<400> SEQUENCE: 13
caggtgcagc tgcaggagtc gggcccagga ctggtgaagc cttcacagac cctgtccctc    60

```
acctgcactg tctctggtgg ctccatcagc agtggtgggt actactggag ctggatccgc    120
cagcacccag ggaagggcct ggagtggatt gggtacatct attacagtgg gagcacctac    180
tacaacccgt ccctcaagag tcgagttacc atatcagtag acacgtctaa gaaccagttc    240
tccctgaagc tgagctctgt gactgccgcg gacacggccg tgtatttctg tgcgagagat    300
cgggaacttg agggttactc caactactac ggtgtggacg tctggggcca agggaccacg    360
gtcaccgtct cctc                                                     374
```

```
<210> SEQ ID NO 14
<211> LENGTH: 124
<212> TYPE: PRT
<213> ORGANISM: Artificial
<220> FEATURE:
<223> OTHER INFORMATION: Antibody

<400> SEQUENCE: 14
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Asp Arg Glu Leu Glu Gly Tyr Ser Asn Tyr Tyr Gly Val
            100                 105                 110

Asp Val Trp Gly Gln Gly Thr Thr Val Thr Val Ser
        115                 120

```
<210> SEQ ID NO 15
<211> LENGTH: 321
<212> TYPE: DNA
<213> ORGANISM: Artificial
<220> FEATURE:
<223> OTHER INFORMATION: Antibody

<400> SEQUENCE: 15
gacatccaga tgacccagtc tccatcctcc ctgtctgcat ctgtaggaga cagagtcacc     60
atcacttgcc gggcaagtca ggccattagc aactatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag cctgcagcct    240
gaagattttg caacttatta ctgtcaacag aataatagtc tcccgatcac cttcggccaa    300
gggacacgac tggagattaa a                                             321
```

```
<210> SEQ ID NO 16
<211> LENGTH: 107
<212> TYPE: PRT
<213> ORGANISM: Artificial
<220> FEATURE:
<223> OTHER INFORMATION: Antibody

<400> SEQUENCE: 16
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ala Ile Ser Asn Tyr
            20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Asn Ser Leu Pro Ile
                85                  90                  95

Thr Phe Gly Gln Gly Thr Arg Leu Glu Ile Lys
            100                 105

<210> SEQ ID NO 17
<211> LENGTH: 354
<212> TYPE: DNA
<213> ORGANISM: Artificial
<220> FEATURE:
<223> OTHER INFORMATION: Antibody

<400> SEQUENCE: 17
gaggtgcagc tggtgcagtc tggagcagag gtgaaaaagc ccggggagtc tctgaagatc      60
tcctgtaagg gttctggata cagctttacc agctactgga tcggctgggt gcgccagatg     120
cccgggaaag gcctggagtg gatggggatc atctatcctg gtgactctga taccagatac     180
agcccgtcct tccaaggcca ggtcaccatc tcagccgaca gtccatcag caccgcctac      240 ctgcagtgga gcagcctgaa ggcctcggac accgccatgt attactgtgc gagacatgaa     300
aactacggtg actacaacta ctggggccag ggaaccctgg tcaccgtctc ctca           354

<210> SEQ ID NO 18
<211> LENGTH: 118
<212> TYPE: PRT
<213> ORGANISM: Artificial
<220> FEATURE:
<223> OTHER INFORMATION: Antibody

<400> SEQUENCE: 18

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Tyr Gly Asp Tyr Asn Tyr Trp Gly Gln Gly Thr
            100                 105                 110

Leu Val Thr Val Ser Ser
            115

<210> SEQ ID NO 19

<211> LENGTH: 321
<212> TYPE: DNA
<213> ORGANISM: Artificial
<220> FEATURE:
<223> OTHER INFORMATION: Antibody

<400> SEQUENCE: 19

```
gacatccaga tgacccagtc tccatcctcc ctgtctgcat ctgtcggaga cagagtcacc    60
atcacttgcc gggcaagtca gagcattcgc agctatttaa attggtatca gcagaaacca   120
gggaaagccc ctaagctcct gatctatgct gcttccagtt tgcaaagtgg ggtcccatca   180
aggttcagtg gcagtggatc tgggacagat tcactctca ccatcagcag tctgcaacct    240
gaagattttg cactttactg ctgtcaacag agtaacggtt ccccgctcac tttcggcgga   300
gggaccaagg tggagatcaa a                                             321
```

<210> SEQ ID NO 20
<211> LENGTH: 107
<212> TYPE: PRT
<213> ORGANISM: Artificial
<220> FEATURE:
<223> OTHER INFORMATION: Antibody

<400> SEQUENCE: 20

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Arg Ser Tyr
            20                  25                  30
Leu Asn Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Leu Tyr Cys Cys Gln Gln Ser Asn Gly Ser Pro Leu
                85                  90                  95
Thr Phe Gly Gly Gly Thr Lys Val Glu Ile Lys
            100                 105

<210> SEQ ID NO 21
<211> LENGTH: 380
<212> TYPE: DNA
<213> ORGANISM: Artificial
<220> FEATURE:
<223> OTHER INFORMATION: Antibody

<400> SEQUENCE: 21

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag gaagggcct ggagtggatt ggtacatct attacagtgg gagcacctac     180
tacaacccgt ccctcaggag tcgagttacc atatcagtag acacgtctaa gaaccagttc   240
tccctgaagc tgagctctgt gactgccgcg gacacggccg tgtattactg tgcgagagat   300
agagagagag agtgggatga ttacggtgac ccccaaggta tggacgtctg gggccaaggg   360
accacggtca ccgtctcctc                                               380
```

<210> SEQ ID NO 22
<211> LENGTH: 126
<212> TYPE: PRT

```
<213> ORGANISM: Artificial
<220> FEATURE:
<223> OTHER INFORMATION: Antibody

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Arg Glu Trp Asp Asp Tyr Gly Asp Pro Gln
            100                 105                 110

Gly Met Asp Val Trp Gly Gln Gly Thr Thr Val Thr Val Ser
        115                 120                 125

<210> SEQ ID NO 23
<211> LENGTH: 321
<212> TYPE: DNA
<213> ORGANISM: Artificial
<220> FEATURE:
<223> OTHER INFORMATION: Antibody

<400> SEQUENCE: 23
gacatccaga tgacccagtc tccatcctcc ctgtctgcat ctgtaggaga cagagtcacc      60
atcacttgcc gggcaagtca gagcattagc agctatttac attggtatca gcagaaacca     120
gggaaagccc ctaagctcct gatccatgct gcatccagtt tacaaagtgg ggtcccatca     180
aggttcagtg gcagtggatc tgggacagat ttcactctca ccatcagtag tctgcaacct     240
gaagattttg caacttacta ctgtcaacag agttacagta acccgctcac tttcggcgga     300
gggaccaagg tggagatcca a                                                321

<210> SEQ ID NO 24
<211> LENGTH: 107
<212> TYPE: PRT
<213> ORGANISM: Artificial
<220> FEATURE:
<223> OTHER INFORMATION: Antibody

<400> SEQUENCE: 24

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu His Trp Tyr Gln Gln Lys Pro Gly Lys Ala Pro Lys Leu Leu Ile
        35                  40                  45

His Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Asn Pro Leu
                85                  90                  95
```

```
Thr Phe Gly Gly Gly Thr Lys Val Glu Ile Gln
            100                 105
```

```
<210> SEQ ID NO 25
<211> LENGTH: 354
<212> TYPE: DNA
<213> ORGANISM: Artificial
<220> FEATURE:
<223> OTHER INFORMATION: Antibody

<400> SEQUENCE: 25
gaggtgcagc tggtgcagtc tggagcagag gtgaaaaagc ccggggagtc tctgaagatc    60
tcctgtaagg gttctggata cagctttacc agctactgga tcggctgggt gcgccagatg   120
cccgggaaag gcctggagtg gatgggggatc atctggcctg gtgactctga taccatatac  180
agcccgtcct tccaaggcca ggtcaccatc tcagccgaca gtccatcag caccgcctac   240 ctgcagtgga gcagcctgaa ggcctcggac accgccatgt attactgtgc gagacatgaa  300
aactacggtg actacaacta ctggggccag ggaaccctgg tcaccgtctc ctca        354
```

```
<210> SEQ ID NO 26
<211> LENGTH: 118
<212> TYPE: PRT
<213> ORGANISM: Artificial
<220> FEATURE:
<223> OTHER INFORMATION: Antibody

<400> SEQUENCE: 26

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Trp Pro Gly Asp Ser Asp Thr Ile Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg His Glu Asn Tyr Gly Asp Tyr Asn Tyr Trp Gly Gln Gly Thr
            100                 105                 110

Leu Val Thr Val Ser Ser
        115
```

```
<210> SEQ ID NO 27
<211> LENGTH: 321
<212> TYPE: DNA
<213> ORGANISM: Artificial
<220> FEATURE:
<223> OTHER INFORMATION: Antibody

<400> SEQUENCE: 27
gacatccaga tgacccagtc tccatcctcc ctgtctgcat ctgtgggaga cagagtcacc    60
atcacttgcc gggcaagtca gagcattcga agttatttaa attggtatca gcagaaaccg   120
gggaatgccc ctaaactcct gatctatgct gcatccagtt tgcaaagtgg ggtcccatca   180
aggttcagtg gcagtggatc tgggacagat ttcactctca ccatcagcag tctgcaacct   240
gaagattttg cactttacta ctgtcaacag agtatcagtt ccccgctcac tttcggcgga   300
```

```
gggaccaagg tggagatcaa a                                              321
```

<210> SEQ ID NO 28
<211> LENGTH: 107
<212> TYPE: PRT
<213> ORGANISM: Artificial
<220> FEATURE:
<223> OTHER INFORMATION: Antibody

<400> SEQUENCE: 28

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Asn Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Leu Tyr Tyr Cys Gln Gln Ser Ile Ser Ser Pro Leu
                85                  90                  95

Thr Phe Gly Gly Gly Thr Lys Val Glu Ile Lys
            100                 105
```

<210> SEQ ID NO 29
<211> LENGTH: 374
<212> TYPE: DNA
<213> ORGANISM: Artificial
<220> FEATURE:
<223> OTHER INFORMATION: Antibody

<400> SEQUENCE: 29

```
caggtgcagc tggtgcagtc tggggctgag gtgaagaagc ctggggcctc agtgaaggtc      60
tcctgcaagg cttctggata caccttcacc agttatgata tcaactgggt gcgacaggcc     120
actggacaag gcttgagtg gatgggatgg atgaaccta acagtggtga cactggctat      180
gcacaggtgt tccagggcag agtcaccatg acctggaaca cctccataag cacagcctac     240
atggaactga gcagcctgag atctgaggac acggccgtgt attactgtgc gagatttggg     300
gatctcccgt atgactacag ttactacgaa tggttcgacc cctggggcca gggaaccctg     360
gtcaccgtct cctc                                                       374
```

<210> SEQ ID NO 30
<211> LENGTH: 124
<212> TYPE: PRT
<213> ORGANISM: Artificial
<220> FEATURE:
<223> OTHER INFORMATION: Antibody

<400> SEQUENCE: 30

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Asp Ile Asn Trp Val Arg Gln Ala Thr Gly Gln Gly Leu Glu Trp Met
        35                  40                  45

Gly Trp Met Asn Pro Asn Ser Gly Asp Thr Gly Tyr Ala Gln Val Phe
    50                  55                  60
```

Gln Gly Arg Val Thr Met Thr Trp Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Gly Asp Leu Pro Tyr Asp Tyr Ser Tyr Tyr Glu Trp Phe
            100                 105                 110

Asp Pro Trp Gly Gln Gly Thr Leu Val Thr Val Ser
        115                 120

<210> SEQ ID NO 31
<211> LENGTH: 321
<212> TYPE: DNA
<213> ORGANISM: Artificial
<220> FEATURE:
<223> OTHER INFORMATION: Antibody

<400> SEQUENCE: 31
gacatccaga tgacccagtc tccatcctcc ctgtctgcat ctgtaggaga cagagtcacc    60
atcacttgcc gggcaagcca gagcattagc agctatttaa attggtatca gcagagacca   120
gggaaagccc ctaagctcct gatctatgca gcatccagtt tgcaaagtgg ggtcccatca   180
aggttcagtg gcagtggatc tgggacagat ttcactctca ccatcagcag tctgcaacct   240
gaagattttg caacttacta ctgtcaacag agttacagta ccccgctcac tttcggcgga   300
gggaccaagg tggagatcaa a                                              321

<210> SEQ ID NO 32
<211> LENGTH: 107
<212> TYPE: PRT
<213> ORGANISM: Artificial
<220> FEATURE:
<223> OTHER INFORMATION: Antibody

<400> SEQUENCE: 32

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
             20                  25                  30

Leu Asn Trp Tyr Gln Gln Arg Pro Gly Lys Ala Pro Lys Leu Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105

<210> SEQ ID NO 33
<211> LENGTH: 386
<212> TYPE: DNA
<213> ORGANISM: Artificial
<220> FEATURE:
<223> OTHER INFORMATION: Antibody

<400> SEQUENCE: 33
caggtacagc tgcagcagtc aggtccagga ctggtgaagc cctcgcagac cctctcactc    60
acctgtgcca tctccgggga cagtgtctct agcaacagtg ctgcttggaa ctggatcagg   120

```
cagtccccat cgagaggcct tgagtggctg ggaaggacat actacaggtc caagtggtat    180
aatgattatg cagtatctgt gaaaagtcga ataaccatca acccagacac atccaagaac    240
cagttctccc tgcagctgaa ctctgtgact cccgaggaca cggctgtgta ttactgtgca    300
agagatctct acgatttttg gagtggttat ccctactact acggtatgga cgtctggggc    360
caagggacca cggtcaccgt ctcctc                                         386
```

<210> SEQ ID NO 34
<211> LENGTH: 128
<212> TYPE: PRT
<213> ORGANISM: Artificial
<220> FEATURE:
<223> OTHER INFORMATION: Antibody

<400> SEQUENCE: 34

```
Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Leu Tyr Asp Phe Trp Ser Gly Tyr Pro Tyr
            100                 105                 110

Tyr Tyr Gly Met Asp Val Trp Gly Gln Gly Thr Thr Val Thr Val Ser
        115                 120                 125
```

<210> SEQ ID NO 35
<211> LENGTH: 383
<212> TYPE: DNA
<213> ORGANISM: Artificial
<220> FEATURE:
<223> OTHER INFORMATION: Antibody

<400> SEQUENCE: 35

```
caggtacagc tgcagcagtc aggtccagga ctggtgaagc cctcgcagac cctctcactc     60
acctgtgcca tctccgggga cagtgtctct agcaacagtg ctgcttggaa ctggatcagg    120
cagtccccat cgagaggcct tgagtggctg ggaaggacat actacaggtc caagtggtat    180
aatgattatg cagtatctgt gaaaagtcga ataaccatca acccagacac atccaagaac    240
cagttctccc tgcagctgaa ctctgtgact cccgaggaca cggctgtgta ttactgtgca    300
agagattact atggttcggg gagtttctac tactactacg gtatggacgt ctggggccaa    360
gggaccacgg tcaccgtctc ctc                                            383
```

<210> SEQ ID NO 36
<211> LENGTH: 127
<212> TYPE: PRT
<213> ORGANISM: Artificial
<220> FEATURE:
<223> OTHER INFORMATION: Antibody

<400> SEQUENCE: 36

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Tyr Tyr Gly Ser Gly Ser Phe Tyr Tyr Tyr
        100                 105                 110

Tyr Gly Met Asp Val Trp Gly Gln Gly Thr Thr Val Thr Val Ser
    115                 120                 125

<210> SEQ ID NO 37
<211> LENGTH: 321
<212> TYPE: DNA
<213> ORGANISM: Artificial
<220> FEATURE:
<223> OTHER INFORMATION: Antibody

<400> SEQUENCE: 37
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaaggtcct gatctatgct gcatccaatt tgcaaagtgg ggtcccatca    180
aggttcagtg gcagtggatc tgggacagat ttcactctca ccatcagcag tctgcaacct    240
gaagattttg caacttacta ctgtcaacag agttacagta cccctcggac gttcggccaa    300
gggaccaagg tggaaatcaa a                                              321

<210> SEQ ID NO 38
<211> LENGTH: 107
<212> TYPE: PRT
<213> ORGANISM: Artificial
<220> FEATURE:
<223> OTHER INFORMATION: Antibody

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Val Leu Ile
        35                  40                  45

Tyr Ala Ala Ser Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Arg
            85                  90                  95

Thr Phe Gly Gln Gly Thr Lys Val Glu Ile Lys
        100                 105

<210> SEQ ID NO 39

<211> LENGTH: 371
<212> TYPE: DNA
<213> ORGANISM: Artificial
<220> FEATURE:
<223> OTHER INFORMATION: Antibody

<400> SEQUENCE: 39

```
caggtgcagc tgcaggagtc gggcccagga ctggtgaagc cttcggagac cctgtccctc    60
acctgcactg tctctggtgg ctccatcagt agttactact ggagctggat ccggcagccc   120
gccgggaagg gactggagtg gattgggcat atctatacca gtgggagcac caactacaac   180
ccctccctca gagtcgagt caccatgtca gtagacacgt ccaagaacca gttctccctg   240
aagctgagct ctgtgaccgc cgcggacacg gccgtgtatt actgtgcgag agaagcgatt   300
tttggagtgg ccccctacta ctactacggt atggacgtct ggggccaagg gaccacggtc   360
accgtctcct c                                                         371
```

<210> SEQ ID NO 40
<211> LENGTH: 123
<212> TYPE: PRT
<213> ORGANISM: Artificial
<220> FEATURE:
<223> OTHER INFORMATION: Antibody

<400> SEQUENCE: 40

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly His Ile Tyr Thr Ser Gly Ser Thr Asn Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Glu Ala Ile Phe Gly Val Gly Pro Tyr Tyr Tyr Tyr Gly Met Asp
            100                 105                 110

Val Trp Gly Gln Gly Thr Thr Val Thr Val Ser
        115                 120

<210> SEQ ID NO 41
<211> LENGTH: 377
<212> TYPE: DNA
<213> ORGANISM: Artificial
<220> FEATURE:
<223> OTHER INFORMATION: Antibody

<400> SEQUENCE: 41

```
caggtgcagc tggtgcagtc tggggctgag gtgaagaagc ctggggcctc agtgaaggtc    60
tcctgcaagg cttctggata caccttcacc ggctactata tgcactgggt gcgacaggcc   120
cctggacaag gcttgagtg gatgggatgg atcaaccct aatattggtgg cacaaactgt   180
gcacagaagt tcagggcag gtcaccatg accagggaca cgtccatcag cacagcctac   240
atggagctga gcaggctgag atctgacgac acggccgtgt attactgtgc gagaggggga   300
cggtatagca gcagctggtc ctactactac tacggtatgg acgtctgggg ccaagggacc   360
acggtcaccg tctcctc                                                  377
```

-continued

<210> SEQ ID NO 42
<211> LENGTH: 125
<212> TYPE: PRT
<213> ORGANISM: Artificial
<220> FEATURE:
<223> OTHER INFORMATION: Antibody

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ile Gly Gly Thr Asn Cys Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Gly Gly Arg Tyr Ser Ser Ser Trp Ser Tyr Tyr Tyr Tyr Gly
            100                 105                 110

Met Asp Val Trp Gly Gln Gly Thr Thr Val Thr Val Ser
        115                 120                 125
```

<210> SEQ ID NO 43
<211> LENGTH: 336
<212> TYPE: DNA
<213> ORGANISM: Artificial
<220> FEATURE:
<223> OTHER INFORMATION: Antibody

<400> SEQUENCE: 43

```
gatattctga tgacccagac tccactctct ctgtccgtca cccctggaca gccggcctcc      60
atctcctgca agtctagtca gagcctcctg cttagtgatg gagggaccta tttgtattgg     120
tacctgcaga agccaggcca gcctccacag ctcctgatct atgaagtttc caaccggttc     180
tctggagtgc cagataggtt cagtggcagc gggtcaggga cagatttcac actgaaaatc     240
agccgggtgg aggctgagga tgttggggtt tattactgca tgcaaagtat gcagcttccg     300
atcaccttcg gccaagggac acgactggaa attaaa                              336
```

<210> SEQ ID NO 44
<211> LENGTH: 112
<212> TYPE: PRT
<213> ORGANISM: Artificial
<220> FEATURE:
<223> OTHER INFORMATION: Antibody

<400> SEQUENCE: 44

```
Asp Ile Leu Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu Leu Ser
            20                  25                  30

Asp Gly Gly Thr Tyr Leu Tyr Trp Tyr Leu Gln Lys Pro Gly Gln Pro
        35                  40                  45

Pro Gln Leu Leu Ile Tyr Glu Val Ser Asn Arg Phe Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Met Gln Leu Pro Ile Thr Phe Gly Gln Gly Thr Arg Leu Glu Ile Lys
            100                 105                 110

<210> SEQ ID NO 45
<211> LENGTH: 380
<212> TYPE: DNA
<213> ORGANISM: Artificial
<220> FEATURE:
<223> OTHER INFORMATION: Antibody

<400> SEQUENCE: 45
caggtgcagc tgcaggagtc gggcccagga ctggtgaagc cttcggagac cctgtccctc     60
acctgcactg tctctggtgg ctccgtcagc agtggtggtt actactggag ctggatccgg    120
cagcccccag ggaagggact ggagtggatt gggtatatct attacagtgg gagcaccaac    180
tacaacccct ccctcaagag tcgagtcacc atatcagtag acacgtccaa gaaccagttc    240
tccctgaagc tgagctctgt gaccgctgcg gacacggccg tgtattactg tgcgagaggg    300
ggggacagta actacgagga ttactactac tactacggta tggacgtctg gggccaaggg    360
accacggtca ccgtctcctc                                                380

<210> SEQ ID NO 46
<211> LENGTH: 126
<212> TYPE: PRT
<213> ORGANISM: Artificial
<220> FEATURE:
<223> OTHER INFORMATION: Antibody

<400> SEQUENCE: 46

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Asp Ser Asn Tyr Glu Asp Tyr Tyr Tyr Tyr Tyr
            100                 105                 110

Gly Met Asp Val Trp Gly Gln Gly Thr Thr Val Thr Val Ser
        115                 120                 125

<210> SEQ ID NO 47
<211> LENGTH: 321
<212> TYPE: DNA
<213> ORGANISM: Artificial
<220> FEATURE:
<223> OTHER INFORMATION: Antibody

<400> SEQUENCE: 47
gacatccaga tgacccagtc tccatcctcc ctgtctgcat ctgtaggaga cagagtcacc     60

```
atcacttgcc gggcaagtca gagcattagc atctatttac attggtatca gcagaaacca    120
gggaaagccc ctaagctctt gatctctgct gcatccagtt tgcaaagtgg ggtcccgtca    180
aggttcagtg gcagtggatc tgggacagat tcactctcca ccatcagaag tctgcaacct    240
gaagattttg caacttacta ctgtcaacag agttacactt ccccgatcac cttcggccaa    300
gggacacgac tggagattaa a                                              321
```

<210> SEQ ID NO 48
<211> LENGTH: 107
<212> TYPE: PRT
<213> ORGANISM: Artificial
<220> FEATURE:
<223> OTHER INFORMATION: Antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ile Tyr
            20                  25                  30

Leu His Trp Tyr Gln Gln Lys Pro Gly Lys Ala Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Arg Ser Leu Gln Pro
65                  70                  75                  80

Glu Asp Phe Ala Thr Tyr Tyr Cys Gln Gln Ser Tyr Thr Ser Pro Ile
                85                  90                  95

Thr Phe Gly Gln Gly Thr Arg Leu Glu Ile Lys
            100                 105

<210> SEQ ID NO 49
<211> LENGTH: 380
<212> TYPE: DNA
<213> ORGANISM: Artificial
<220> FEATURE:
<223> OTHER INFORMATION: Antibody

<400> SEQUENCE: 49

```
caggtgcagc tgcaggagtc gggcccagga ctggtgaagc cttcggagac cctgtccctc    60
acctgcactg tctctggtgg ctccatcagt agttactact ggagctggat ccggcagccc    120
ccagggaagg gactggagtg gattgggtat atctattaca gtgggagcac caactacaac    180
ccctccctca gagtcgagt caccatatca gtagacacgt ccaagcacca gttctccctg    240
aagctgagct ctgtgaccgc tgcggacacg gccgtgtatt actgtgcgag agattcgagt    300
tactatgata gtagtggtta ttacttatac tactacgcta tggacgtctg gggccaaggg    360
accacggtca ccgtctcctc                                                380
```

<210> SEQ ID NO 50
<211> LENGTH: 126
<212> TYPE: PRT
<213> ORGANISM: Artificial
<220> FEATURE:
<223> OTHER INFORMATION: Antibody

<400> SEQUENCE: 50

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr 20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Tyr Asn Pro Ser Leu Lys
50                  55                  60

Ser Arg Val Thr Ile Ser Val Asp Thr Ser Lys His Gln Phe Ser Leu
65                  70                  75                  80

Lys Leu Ser Ser Val Thr Ala Ala Asp Thr Ala Val Tyr Tyr Cys Ala
                85                  90                  95

Arg Asp Ser Ser Tyr Tyr Asp Ser Ser Gly Tyr Tyr Leu Tyr Tyr Tyr
            100                 105                 110

Ala Met Asp Val Trp Gly Gln Gly Thr Thr Val Thr Val Ser
            115                 120                 125

<210> SEQ ID NO 51
<211> LENGTH: 339
<212> TYPE: DNA
<213> ORGANISM: Artificial
<220> FEATURE:
<223> OTHER INFORMATION: Antibody

<400> SEQUENCE: 51
gacatcgtga tgacccagtc tccagactcc ctggctgtgt ctctgggcga gagggccacc      60
atcaactgca gtccagcca gagtgtttta tacagctcca acaataagaa ctacttagct     120
tggtaccagc agaaaccagg acagcctcct aagctgctca tttcctgggc atctacccgg    180
gaatccgggg tccctgaccg attcagtggc agcgggtctg ggacagattt cactctcacc    240
atcagcagcc tgcaggctga agatgtggca gtttattact gtcagcaata ttatactact    300
cctctcactt tcggccctgg gaccaaagtg gatatcaaa                           339

<210> SEQ ID NO 52
<211> LENGTH: 113
<212> TYPE: PRT
<213> ORGANISM: Artificial
<220> FEATURE:
<223> OTHER INFORMATION: Antibody

<400> SEQUENCE: 52

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Ser Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Thr Thr Pro Leu Thr Phe Gly Pro Gly Thr Lys Val Asp Ile
            100                 105                 110

Lys

<210> SEQ ID NO 53
<211> LENGTH: 357
<212> TYPE: DNA

<213> ORGANISM: Artificial
<220> FEATURE:
<223> OTHER INFORMATION: Antibody

<400> SEQUENCE: 53

```
gaggtgcaac tggtggagtc tggggggaggc ttggtacagc ctggggggtc cctgagactc    60
tcctgtgcag cctctggatt caccttcagt atctatagca tgaactgggt ccgccaggct   120
ccagggaagg ggctggagtg ggtttcatac attagtagta gtagtagtac catatactac   180
gcagactctg tgaagggccg attcaccatc tccagagaca atgccaagaa ctcactgtat   240
ctgcaaatga acagcctgag agacgaggac acggctgtgt attactgtgc gagagatagg   300
ggtgacttcg atgcttttga tatctggggc caagggacaa tggtcaccgt ctcttca      357
```

<210> SEQ ID NO 54
<211> LENGTH: 119
<212> TYPE: PRT
<213> ORGANISM: Artificial
<220> FEATURE:
<223> OTHER INFORMATION: Antibody

<400> SEQUENCE: 54

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ile Tyr
            20                  25                  30
Ser Met Asn Trp Val Arg Gln Ala Pro Gly Lys Gly Leu Glu Trp Val
        35                  40                  45
Ser Tyr Ile Ser Ser Ser Ser Ser Thr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Asp Glu Asp Thr Ala Val Tyr Tyr Cys
                85                  90                  95
Ala Arg Asp Arg Gly Asp Phe Asp Ala Phe Asp Ile Trp Gly Gln Gly
            100                 105                 110
Thr Met Val Thr Val Ser Ser
        115

<210> SEQ ID NO 55
<211> LENGTH: 321
<212> TYPE: DNA
<213> ORGANISM: Artificial
<220> FEATURE:
<223> OTHER INFORMATION: Antibody

<400> SEQUENCE: 55

```
gacatccaga tgacccagtc tccatcctcc ctgtctgcat ctgtaggaga cagagtcacc    60
atcacttgcc aggcgagtca ggacattacc aactatttga attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatataa ctgtcaacag tgtgaaaatt tcccgatcac cttcggccaa   300
gggacacgac tggagattaa a                                             321
```

<210> SEQ ID NO 56
<211> LENGTH: 107
<212> TYPE: PRT
<213> ORGANISM: Artificial

<220> FEATURE:
<223> OTHER INFORMATION: Antibody

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Thr Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Asn Cys Gln Gln Cys Glu Asn Phe Pro Ile
                85                  90                  95

Thr Phe Gly Gln Gly Thr Arg Leu Glu Ile Lys
            100                 105

<210> SEQ ID NO 57
<211> LENGTH: 336
<212> TYPE: DNA
<213> ORGANISM: Artificial
<220> FEATURE:
<223> OTHER INFORMATION: Antibody

<400> SEQUENCE: 57
gatattgtga tgactcagtc tccactctcc ctgcccgtca cccctggaga gccggcctcc      60
atctcctgca ggtctagtca gagcctcctg tatagtaatg gatacaagta tttggattgg     120
tacctgcaga agccagggca gtctccacag ctcctgatct atttgggttc taatcgggcc     180
tccggggtcc ctgacaggtt cagtggcagt ggatcaggca cagatttac actgaaaatc      240
agcagagtgg aggctgagga tgttggggtt tattattgca tgcaggctct acaaactccg     300
atcaccttcg gccaagggac acgactggag attaaa                               336

<210> SEQ ID NO 58
<211> LENGTH: 112
<212> TYPE: PRT
<213> ORGANISM: Artificial
<220> FEATURE:
<223> OTHER INFORMATION: Antibody

<400> SEQUENCE: 58

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 59
<211> LENGTH: 374
<212> TYPE: DNA
<213> ORGANISM: Artificial
<220> FEATURE:
<223> OTHER INFORMATION: Antibody

<400> SEQUENCE: 59
caggtgcagc tgcaggagtc gggcccagga ctggtgaagc cttcggagac cctgtccctc    60
acctgcactg tctctggtgg ctccgtcagc agtggtggtt actactggaa ctggatccgg   120
cagcccccag ggaagggact ggagtggatt gggtatatca attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagagat   300
cgagaactgg aactttacta ctactactac ggtatggacg tctggggcca agggaccacg   360
gtcaccgtct cctc                                                     374

<210> SEQ ID NO 60
<211> LENGTH: 124
<212> TYPE: PRT
<213> ORGANISM: Artificial
<220> FEATURE:
<223> OTHER INFORMATION: Antibody

<400> SEQUENCE: 60

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
            115                 120

<210> SEQ ID NO 61
<211> LENGTH: 374
<212> TYPE: DNA
<213> ORGANISM: Artificial
<220> FEATURE:
<223> OTHER INFORMATION: Antibody

<400> SEQUENCE: 61
caggtgcagc tgcaggagtc gggcccagga ctggtgaagc cttctgagac cctgtccctc    60
acctgcactg tctctggtgg ctccgtcagc agtggtggtt actactggaa ctggatccgg   120
cagcccccag ggaagggact ggagtggatt gggtatatca attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagagat   300
cgagaactgg aactttacta ctactactac ggtatggacg tctggggcca agggaccacg   360
gtcaccgtct cctc 374

<210> SEQ ID NO 62
<211> LENGTH: 124
<212> TYPE: PRT
<213> ORGANISM: Artificial
<220> FEATURE:
<223> OTHER INFORMATION: Antibody

<400> SEQUENCE: 62

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Asn Trp Ile Arg Gln Pro Pro Gly Lys Gly Leu Glu
        35                  40                  45

Trp Ile Gly Tyr Ile Asn Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Arg Glu Leu Glu Leu Tyr Tyr Tyr Tyr Gly Met
            100                 105                 110

Asp Val Trp Gly Gln Gly Thr Thr Val Thr Val Ser
        115                 120
```

<210> SEQ ID NO 63
<211> LENGTH: 336
<212> TYPE: DNA
<213> ORGANISM: Artificial
<220> FEATURE:
<223> OTHER INFORMATION: Antibody

<400> SEQUENCE: 63
gatattgtga tgactcagtc tccactctcc ctgcccgtca cccctggaga gccggcctcc    60
atctcctgca ggtctagtca gagcctcctg tatagtaatg gatacaagta tttggattgg   120
tacctgcaga agccagggca gtctccacag ctcatgatct atttgggttc taatcgggcc   180
tccggggtcc ctgacaggtt cagtggcagt ggatcaggca cagattttac actgaaaatc   240
agcagagtgg aggctgagga tgttggggtt tattattgca tgcaggctct acaaactccg   300
atcaccttcg gccaagggac acgactggag attaaa                             336

<210> SEQ ID NO 64
<211> LENGTH: 112
<212> TYPE: PRT
<213> ORGANISM: Artificial
<220> FEATURE:
<223> OTHER INFORMATION: Antibody

<400> SEQUENCE: 64

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Tyr Ser
            20                  25                  30

Asn Gly Tyr Lys Tyr Leu Asp Trp Tyr Leu Gln Lys Pro Gly Gln Ser
        35                  40                  45

Pro Gln Leu Met Ile Tyr Leu Gly Ser Asn Arg Ala Ser Gly Val Pro
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 65
<211> LENGTH: 363
<212> TYPE: DNA
<213> ORGANISM: Artificial
<220> FEATURE:
<223> OTHER INFORMATION: Antibody

<400> SEQUENCE: 65
caggtgcagc tggtggagtc tgggggaggc gtggtccagc ctggagggtc cctgagactc        60
tcctgtgcag cgtctggatt caccttcagt agctatggca tgcactgggt ccgccaggct       120
ccaggcaagg ggctggagtg ggtggcagtt atatggtatg atggaagtaa taaatactat       180
gcagactccg tgaagggccg attcaccatc tccagagaca attccaagaa cacgctgtat       240
ctgcaaatga acagcctgag agccgaggac acggctgtgt attactgtgc gagagcagct       300
cgccttgact actactacgg tatggacgtc tggggccaag ggaccacggt caccgtctcc       360
tca                                                                    363

<210> SEQ ID NO 66
<211> LENGTH: 121
<212> TYPE: PRT
<213> ORGANISM: Artificial
<220> FEATURE:
<223> OTHER INFORMATION: Antibody

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Ala Arg Leu Asp Tyr Tyr Tyr Gly Met Asp Val Trp Gly
            100                 105                 110

Gln Gly Thr Thr Val Thr Val Ser Ser
        115                 120

<210> SEQ ID NO 67
<211> LENGTH: 321
<212> TYPE: DNA
<213> ORGANISM: Artificial
<220> FEATURE:
<223> OTHER INFORMATION: Antibody

<400> SEQUENCE: 67

```
gacatccaga tgacccagtc tccatcctcc ctgtctgcat ctgtaggaga cagagtctcc    60
atcacttgcc gggcaagtca gagcattaac agctatttaa attggtttca gcagaagcca   120
gggaaagccc ctcagctcct gatctttggt gcatccggtt tgcaaagtgg ggtcccatca   180
aggttcagtg gcagtggatc tgggacagat ttcactctca ccatcaacag tctgcaacct   240
gaagattttg caacttacta ctgtcaacag agttacagtt ccccgctcac cttcggccaa   300
gggacacgac tggagattaa a                                             321
```

<210> SEQ ID NO 68
<211> LENGTH: 107
<212> TYPE: PRT
<213> ORGANISM: Artificial
<220> FEATURE:
<223> OTHER INFORMATION: Antibody

<400> SEQUENCE: 68

```
Asp Ile Gln Met Thr Gln Ser Pro Ser Ser Leu Ser Ala Ser Val Gly
1               5                   10                  15

Asp Arg Val Ser Ile Thr Cys Arg Ala Ser Gln Ser Ile Asn Ser Tyr
            20                  25                  30

Leu Asn Trp Phe Gln Gln Lys Pro Gly Lys Ala Pro Gln Leu Leu Ile
        35                  40                  45

Phe Gly Ala Ser Gly Leu Gln Ser Gly Val Pro Ser Arg Phe Ser Gly
    50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Ser Tyr Ser Ser Pro Leu
                85                  90                  95

Thr Phe Gly Gln Gly Thr Arg Leu Glu Ile Lys
            100                 105
```

<210> SEQ ID NO 69
<211> LENGTH: 351
<212> TYPE: DNA
<213> ORGANISM: Artificial
<220> FEATURE:
<223> OTHER INFORMATION: Antibody

<400> SEQUENCE: 69

```
caggtgcagc tacagcagtg gggcgcagga ctgttgaagc cttcggagac cctgtccctc    60
acctgcgctg tctatggtgg gtccttcagt ggttactact ggagctggat ccgccagccc   120
ccagggaagg ggctggagtg gattggggaa atcaatcata gtggaagcac caactacaac   180
ccgtccctca agagtcgagt caccatatca gtagaaacgt ccaagaacca gttctccctg   240
aagctgagct ctgtgaccgc cgcggacacg gctgtgtatt actgtgcgag agataagtgg   300
acctggtact cgatctctg gggccgtggc accctggtca ctgtctcctc a             351
```

<210> SEQ ID NO 70
<211> LENGTH: 117
<212> TYPE: PRT
<213> ORGANISM: Artificial
<220> FEATURE:
<223> OTHER INFORMATION: Antibody

<400> SEQUENCE: 70

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
```

```
                20                  25                  30
Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 71
<211> LENGTH: 339
<212> TYPE: DNA
<213> ORGANISM: Artificial
<220> FEATURE:
<223> OTHER INFORMATION: Antibody

<400> SEQUENCE: 71
gacatcgaga tgacccagtc tccagactcc ctggctgtgt ctctgggcga gagggccacc      60
atcaactgca ggtccagcca gagtgtttta tacagctcca gcaataggaa ctacttagct     120
tggtaccagc agaacccagg acagcctcct aagctgctca tttactgggc ttctacccgg     180
gaatccgggg tccctgaccg attcagtggc agcgggtctg ggacagattt cactctcacc     240
atcagcagcc tgcaggctga agatgtggca gtttattact gtcagcaata ttatagtact     300
cctcggacgt tcggccaagg gaccaaggtg gaaatcaaa                            339

<210> SEQ ID NO 72
<211> LENGTH: 113
<212> TYPE: PRT
<213> ORGANISM: Artificial
<220> FEATURE:
<223> OTHER INFORMATION: Antibody

<400> SEQUENCE: 72

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys

<210> SEQ ID NO 73
<211> LENGTH: 374
<212> TYPE: DNA
```

<213> ORGANISM: Artificial
<220> FEATURE:
<223> OTHER INFORMATION: Antibody

<400> SEQUENCE: 73

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatg gggaacatct attacagtgg gagcacctac   180
tacaacccgt ccctcaagag tcgagttacc atatcagtag acacgtctga gaaccagttc   240
tccctgaagc tgaactctgt gactgccgcg gacacggccg tatattactg tgcgagaggg   300
ggaactggaa ccaattacta ctactactac ggtatggacg tctggggcca agggaccacg   360
gtcaccgtct cctc                                                      374
```

<210> SEQ ID NO 74
<211> LENGTH: 124
<212> TYPE: PRT
<213> ORGANISM: Artificial
<220> FEATURE:
<223> OTHER INFORMATION: Antibody

<400> SEQUENCE: 74

Gln Val Gln Leu Gln Glu Ser Gly Pro Gly Leu Val Lys Pro Ser Gln
1               5                   10                  15
Thr Leu Ser Leu Thr Cys Thr Val Ser Gly Gly Ser Ile Ser Ser Gly
            20                  25                  30
Gly Tyr Tyr Trp Ser Trp Ile Arg Gln His Pro Gly Lys Gly Leu Glu
        35                  40                  45
Trp Met Gly Asn Ile Tyr Tyr Ser Gly Ser Thr Tyr Tyr Asn Pro Ser
    50                  55                  60
Leu Lys Ser Arg Val Thr Ile Ser Val Asp Thr Ser Glu Asn Gln Phe
65                  70                  75                  80
Ser Leu Lys Leu Asn Ser Val Thr Ala Ala Asp Thr Ala Val Tyr Tyr
                85                  90                  95
Cys Ala Arg Gly Gly Thr Gly Thr Asn Tyr Tyr Tyr Tyr Gly Met
            100                 105                 110
Asp Val Trp Gly Gln Gly Thr Thr Val Thr Val Ser
        115                 120

<210> SEQ ID NO 75
<211> LENGTH: 324
<212> TYPE: DNA
<213> ORGANISM: Artificial
<220> FEATURE:
<223> OTHER INFORMATION: Antibody

<400> SEQUENCE: 75

```
gaaattgtgt tgacgcagtc tccaggcacc ctgtctttgt ctccagggga aagagccacc    60
ctctcctgca gggccagtca gagtgttagc agcagctact tagcctggta ccagcagaaa   120
cctggccagg ctcccaggct cctcatctat ggtgcatcca gctgggccac tggcatccca   180
aacaggttca gtggcagtgg gtctgggaca gacttcactc tcaccatcag cagactggag   240
cctgaagatt ttgcagtgta ttactgtcag cagtatggta gctcaccgct cactttcggc   300
ggagggacca aggtggagat caaa                                           324
```

<210> SEQ ID NO 76
<211> LENGTH: 108

```
<212> TYPE: PRT
<213> ORGANISM: Artificial
<220> FEATURE:
<223> OTHER INFORMATION: Antibody

<400> SEQUENCE: 76

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Trp Ala Thr Gly Ile Pro Asn Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gly Gly Thr Lys Val Glu Ile Lys
            100                 105

<210> SEQ ID NO 77
<211> LENGTH: 377
<212> TYPE: DNA
<213> ORGANISM: Artificial
<220> FEATURE:
<223> OTHER INFORMATION: Antibody

<400> SEQUENCE: 77
caggtgcagc tgcaggagtc gggcccagga ctggtgaagc cttcacagac cctgtccctc     60
acctgcactg tctctggtgt ctccatcagc agtggtggtt actactggag ctggatccgc    120
cagcacccag ggatgggcct ggagtggatt gggtacatct attacagtgg gagcacctac    180
tacaacccgt ccctcaagag tcgagtcacc atatcagaag acacgtctaa gaaccagttc    240
tccctgaagc tgagctctgt gactgccgcg gacacggccg tgtattactg tgcgagagat    300
tccgagtccg agtatagcag ctcgtcgaac tacggtatgg acgtctgggg ccaagggacc    360
acggtcaccg tctcctc                                                   377

<210> SEQ ID NO 78
<211> LENGTH: 125
<212> TYPE: PRT
<213> ORGANISM: Artificial
<220> FEATURE:
<223> OTHER INFORMATION: Antibody

<400> SEQUENCE: 78

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95
```

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
        115                 120                 125

<210> SEQ ID NO 79
<211> LENGTH: 377
<212> TYPE: DNA
<213> ORGANISM: Artificial
<220> FEATURE:
<223> OTHER INFORMATION: Antibody

<400> SEQUENCE: 79
caggtgcagc tgcaggagtc gggcccagga ctggtgaagc cttcacagac cctgtccctc    60
acctgcactg tctctggtgt ctccatcagc agtggtggtt actactggag ctggatccgc   120
cagcacccag ggatgggcct ggagtggatt ggtacatct attacagtgg gagcacctac    180
tacaacccgt ccctcaagag tcgagtcacc atatcagaag acacgtctaa gaaccagttc   240
tccctgaagc tgagctctgt gactgccgcg gacacggccg tgtattactg tgcgagagat   300
tccgagtccg agtatagcag ctcgtcgaac tacggtatgg acgtctgggg ccaagggacc   360
acggtcaccg tctcctc                                                  377

<210> SEQ ID NO 80
<211> LENGTH: 125
<212> TYPE: PRT
<213> ORGANISM: Artificial
<220> FEATURE:
<223> OTHER INFORMATION: Antibody

<400> SEQUENCE: 80

Gln Val Gln Leu Gln Glu Ser Gly Pro Gly Leu Val Lys Pro Ser Gln
1               5                   10                  15

Thr Leu Ser Leu Thr Cys Thr Val Ser Gly Val Ser Ile Ser Ser Gly
            20                  25                  30

Gly Tyr Tyr Trp Ser Trp Ile Arg Gln His Pro Gly Met Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Ser Glu Ser Glu Tyr Ser Ser Ser Asn Tyr Gly
            100                 105                 110

Met Asp Val Trp Gly Gln Gly Thr Thr Val Thr Val Ser
        115                 120                 125

<210> SEQ ID NO 81
<211> LENGTH: 321
<212> TYPE: DNA
<213> ORGANISM: Artificial
<220> FEATURE:
<223> OTHER INFORMATION: Antibody

<400> SEQUENCE: 81
gacatccaga tgacccagtc tccatcctcc ctgtctgcat ctgtaggaga cagaatcacc    60
atcacttgcc gggcaagtca gaccattagc agctatttaa attggtatca gcagaaacca   120

-continued

```
gggaaagccc ctaagctcct gatctatgct gcatccagtt tgcaaggtgg ggtcccatca    180
aggttcagtg gcagtgtatc tgggacagat ttcaccctca ccgtcagcag tctgcaacct    240
gaagattttg caacttacta ctgtcaacag agttacagta acccgctcac tttcggcgga    300
gggaccaagg tggagatcaa a                                              321
```

<210> SEQ ID NO 82
<211> LENGTH: 107
<212> TYPE: PRT
<213> ORGANISM: Artificial
<220> FEATURE:
<223> OTHER INFORMATION: Antibody

<400> SEQUENCE: 82

```
Asp Ile Gln Met Thr Gln Ser Pro Ser Ser Leu Ser Ala Ser Val Gly
1               5                   10                  15

Asp Arg Ile Thr Ile Thr Cys Arg Ala Ser Gln Thr Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Gly Gly Val Pro Ser Arg Phe Ser Gly
    50                  55                  60

Ser Val Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Asn Pro Leu
                85                  90                  95

Thr Phe Gly Gly Gly Thr Lys Val Glu Ile Lys
            100                 105
```

<210> SEQ ID NO 83
<211> LENGTH: 371
<212> TYPE: DNA
<213> ORGANISM: Artificial
<220> FEATURE:
<223> OTHER INFORMATION: Antibody

<400> SEQUENCE: 83

```
gaggtgcagc tggtgcagtc tggagcagag gtgaaaaagc cgggggagtc tctgaagatc    60
tcctgtaagg gttctggata cagttttacc agctactgga tcggctgggt gcgccagatg    120
cccgggaaag gcctggagtg gatggggatc atctatcctg gtgactctga taccagatac    180
agcccgtcct tccaaggcca ggtcaccatg tcagccgaca gtccatcagt accgcctac    240 ctgcagctga gcagccatga aggcctcgga caccgccatg tattactgtg cgagacagat    300
ggctggaaac tacgtacatc acgggtgatc gagacgtcct ggggccaagg gaccacggtc    360
accgtctcct c                                                         371
```

<210> SEQ ID NO 84
<211> LENGTH: 123
<212> TYPE: PRT
<213> ORGANISM: Artificial
<220> FEATURE:
<223> OTHER INFORMATION: Antibody

<400> SEQUENCE: 84

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30
```

```
Trp Ile Gly Trp Val Arg Gln Met Pro Gly Lys Gly Leu Glu Trp Met
            35                  40                  45
Gly Ile Ile Tyr Pro Gly Asp Ser Asp Thr Arg Tyr Ser Pro Ser Phe
 50                  55                  60
Gln Gly Gln Val Thr Met Ser Ala Asp Lys Ser Ile Ser Thr Ala Tyr
 65                  70                  75                  80
Leu Gln Leu Ser Ser His Glu Gly Leu Gly His Arg His Val Leu Leu
                 85                  90                  95
Cys Glu Thr Asp Gly Trp Lys Leu Arg Thr Ser Arg Val Ile Glu Thr
            100                 105                 110
Ser Trp Gly Gln Gly Thr Thr Val Thr Val Ser
        115                 120
```

<210> SEQ ID NO 85
<211> LENGTH: 324
<212> TYPE: DNA
<213> ORGANISM: Artificial
<220> FEATURE:
<223> OTHER INFORMATION: Antibody

<400> SEQUENCE: 85

```
gaaattgtgt tgacgcagtc tccaggcacc ctgtctttgt ctccagggga aagagccacc     60
ctctcctgca gggccagtca gagtgttatc agcatctact tagcctggta ccagcagaaa    120
cctggccagg ctcccaggct cctcatctat ggtgcatcca gcagggccac tggcatccca    180
gacaggttca gtggcagtgg gtctgggaca gacttcactc tcaccatcag cagactggag    240
cctgaagatt ttgcagtgta ttactgtcag cagtatggta gctcaccgtg cagttttggc    300
caggggacca aactggagat caaa                                            324
```

<210> SEQ ID NO 86
<211> LENGTH: 108
<212> TYPE: PRT
<213> ORGANISM: Artificial
<220> FEATURE:
<223> OTHER INFORMATION: Antibody

<400> SEQUENCE: 86

```
Glu Ile Val Leu Thr Gln Ser Pro Gly Thr Leu Ser Leu Ser Pro Gly
  1               5                  10                  15
Glu Arg Ala Thr Leu Ser Cys Arg Ala Ser Gln Ser Val Ile Ser Ile
             20                  25                  30
Tyr Leu Ala Trp Tyr Gln Gln Lys Pro Gly Gln Ala Pro Arg Leu Leu
         35                  40                  45
Ile Tyr Gly Ala Ser Ser Arg Ala Thr Gly Ile Pro Asp Arg Phe Ser
 50                  55                  60
Gly Ser Gly Ser Gly Thr Asp Phe Thr Leu Thr Ile Ser Arg Leu Glu
 65                  70                  75                  80
Pro Glu Asp Phe Ala Val Tyr Tyr Cys Gln Gln Tyr Gly Ser Ser Pro
                 85                  90                  95
Cys Ser Phe Gly Gln Gly Thr Lys Leu Glu Ile Lys
            100                 105
```

<210> SEQ ID NO 87
<211> LENGTH: 366
<212> TYPE: DNA
<213> ORGANISM: Artificial
<220> FEATURE:
<223> OTHER INFORMATION: Antibody

<400> SEQUENCE: 87

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaggag tcgagttacc atatcagtag acacgtctaa gaaccagttc   240
tccctgaagc tgagctctgt gactgccgcg gacacggccg tgtattactg tgcgagagcg   300
gattacgatt tttggagtgg ttattttgac tactggggcc agggaaccct ggtcaccgtc   360
tcctca                                                               366
```

<210> SEQ ID NO 88
<211> LENGTH: 122
<212> TYPE: PRT
<213> ORGANISM: Artificial
<220> FEATURE:
<223> OTHER INFORMATION: Antibody

<400> SEQUENCE: 88

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Arg Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 89
<211> LENGTH: 322
<212> TYPE: DNA
<213> ORGANISM: Artificial
<220> FEATURE:
<223> OTHER INFORMATION: Antibody

<400> SEQUENCE: 89

```
gacatccaga tgacccagtc tccatcctcc ctgtctgcat ctgtaggaga cagagtcacc    60
atcacttgcc gggcaagtca gggcattaga aatgatttag gctggtatca gcagatacct   120
gggaaagccc ctaagcgcct gatctatgct gcatccagtt tgcaaagtgg ggtcccatca   180
aggttcagcg gcagtggatc tgggacagaa ttcactctca caatcaacag cctgcagcct   240
gaagattttg caacttatta ctgtctacag cataatggtt acccgtggac gttcggccaa   300
gggaccaagg tggaaatcaa ac                                            322
```

<210> SEQ ID NO 90
<211> LENGTH: 107
<212> TYPE: PRT
<213> ORGANISM: Artificial
<220> FEATURE:
<223> OTHER INFORMATION: Antibody

<400> SEQUENCE: 90

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Asn Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105

<210> SEQ ID NO 91
<211> LENGTH: 366
<212> TYPE: DNA
<213> ORGANISM: Artificial
<220> FEATURE:
<223> OTHER INFORMATION: Antibody

<400> SEQUENCE: 91
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg cgagagcg      300 gattacgatt tttggagtgg ttatttttgac tactggggcc agggaaccct ggtcaccgtc     360
tcctca                                                                366

<210> SEQ ID NO 92
<211> LENGTH: 122
<212> TYPE: PRT
<213> ORGANISM: Artificial
<220> FEATURE:
<223> OTHER INFORMATION: Antibody

<400> SEQUENCE: 92

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 93
<211> LENGTH: 322
<212> TYPE: DNA
<213> ORGANISM: Artificial
<220> FEATURE:
<223> OTHER INFORMATION: Antibody

<400> SEQUENCE: 93
gacttccaga tgacccagtc tccatcctcc ctgtctgcat ctgtaggaga cagagtcacc      60
atcacttgcc gggcaagtca ggacattcga atgatttag gctggtatcg cagaaaacct     120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa ac                                             322

<210> SEQ ID NO 94
<211> LENGTH: 107
<212> TYPE: PRT
<213> ORGANISM: Artificial
<220> FEATURE:
<223> OTHER INFORMATION: Antibody

<400> SEQUENCE: 94

Asp Phe Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 95
<211> LENGTH: 366
<212> TYPE: DNA
<213> ORGANISM: Artificial
<220> FEATURE:
<223> OTHER INFORMATION: Antibody

<400> SEQUENCE: 95
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag gaagggcct ggagtggatt ggatacatct attacagtgg gagcacctac     180
tacaacccgt ccctcaagag tcgagttacc atatcaatag acacgtctaa gaaccagttc    240
tccctgaagc tgagctctgt gactgccgcg gacacggccg tgtattactg tgcgagagcg    300
gattacgatt tttggaatgg ttattttgac tactggggcc agggaaccct ggtcaccgtc    360
tcctca                                                                366

<210> SEQ ID NO 96
<211> LENGTH: 122
<212> TYPE: PRT
<213> ORGANISM: Artificial
<220> FEATURE:
<223> OTHER INFORMATION: Antibody

<400> SEQUENCE: 96

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 97
<211> LENGTH: 321
<212> TYPE: DNA
<213> ORGANISM: Artificial
<220> FEATURE:
<223> OTHER INFORMATION: Antibody

<400> SEQUENCE: 97

```
gacatccaga tgacccagtc tccatcctcc ctgtctgcat ctgtaggaga cagagtcacc      60
atcacttgcc gggcaagtca ggacattaga aatgatttag ctggtatcg gcagaaacct     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321
```

<210> SEQ ID NO 98
<211> LENGTH: 107
<212> TYPE: PRT
<213> ORGANISM: Artificial
<220> FEATURE:
<223> OTHER INFORMATION: Antibody

<400> SEQUENCE: 98

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Arg Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 99
<211> LENGTH: 366
<212> TYPE: DNA
<213> ORGANISM: Artificial
<220> FEATURE:
<223> OTHER INFORMATION: Antibody

<400> SEQUENCE: 99
caggtgcagc tgcaggagtc gggcccagga ctggtgaagc ctacacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgacttacc atatcagtag acacgtctaa gaaccagttc     240
tccctgaagc tgagctctgt gactgccgcg gacacggccg tgtattactg tgcgagagca     300
gattacgatt ttggagtgg ttactttgac tactggggcc agggaaccct ggtcaccgtc     360
tcctca                                                                366

<210> SEQ ID NO 100
<211> LENGTH: 122
<212> TYPE: PRT
<213> ORGANISM: Artificial
<220> FEATURE:
<223> OTHER INFORMATION: Antibody

<400> SEQUENCE: 100

Gln Val Gln Leu Gln Glu Ser Gly Pro Gly Leu Val Lys Pro Thr Gln
 1               5                  10                  15

Thr Leu Ser Leu Thr Cys Thr Val Ser Gly Gly Ser Ile Ser Ser Gly
                 20                  25                  30

Asp Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Leu Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 101
<211> LENGTH: 321
<212> TYPE: DNA
<213> ORGANISM: Artificial
<220> FEATURE:
<223> OTHER INFORMATION: Antibody

<400> SEQUENCE: 101
gacatccaga tgacccagtc tccatcctcc ctgtctgcat ctgtaggaga cagagtcacc      60
```
atcacttgcc gggcaagtca gggcattaga aatgatttag gctggtatca gcagaaacca    120
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataataatt acccgtggac gttcggccaa    300
gggaccaagg tggaaatcaa a    321

```
<210> SEQ ID NO 102
<211> LENGTH: 107
<212> TYPE: PRT
<213> ORGANISM: Artificial
<220> FEATURE:
<223> OTHER INFORMATION: Antibody

<400> SEQUENCE: 102
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105

```
<210> SEQ ID NO 103
<211> LENGTH: 366
<212> TYPE: DNA
<213> ORGANISM: Artificial
<220> FEATURE:
<223> OTHER INFORMATION: Antibody

<400> SEQUENCE: 103
```
caggtgcagc tgcaggagtc gggcccagga ctggtgaagc cttcacagac cctgtccctc     60
acctgcactg tctctggtgg ctccatcagt agtggtgatt actactggag ctggatccgc    120
cagcacccag gaagggcct ggagtggatt gggtacatct attacagtgg gagcacctac    180
tacaacccgt ccctcaagag tcgagttacc atatcagtag acacgtctaa gaaccagttc    240
tccctgaagt tgagctctgt gactgccgcg gacacggccg tgtattactg cgagagcc    300 gattacgatt tttggagtgg ttattttgac tactggggcc agggaaccct ggtcaccgtc    360
tcctca    366

```
<210> SEQ ID NO 104
<211> LENGTH: 122
<212> TYPE: PRT
<213> ORGANISM: Artificial
<220> FEATURE:
<223> OTHER INFORMATION: Antibody

<400> SEQUENCE: 104
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly

```
            20                  25                  30
Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
                115                 120
```

<210> SEQ ID NO 105
<211> LENGTH: 321
<212> TYPE: DNA
<213> ORGANISM: Artificial
<220> FEATURE:
<223> OTHER INFORMATION: Antibody

<400> SEQUENCE: 105

```
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatctatgct gcatccagtt tgcaaagtgg ggtcccatca     180
aggttcagcg gcagtggatc tgggacagaa ttcactctca caatcagcag cctgcagcct     240
gaagattttg caacttatta ctgtctacag cataataatt acccgtggac gttcggccaa     300
gggaccaagg tggaaatcaa a                                               321
```

<210> SEQ ID NO 106
<211> LENGTH: 107
<212> TYPE: PRT
<213> ORGANISM: Artificial
<220> FEATURE:
<223> OTHER INFORMATION: Antibody

<400> SEQUENCE: 106

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
                100                 105
```

<210> SEQ ID NO 107
<211> LENGTH: 351
<212> TYPE: DNA
<213> ORGANISM: Artificial
<220> FEATURE:

<223> OTHER INFORMATION: Antibody

<400> SEQUENCE: 107

```
caggtgcagc tgcaggagtc gggcccagga ctggtgaagc cttcacagac cctgtccctc    60
acctgcactg tctctggtgg ctccatcagc agtggtggtt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagag   300
gacgacggta tggacgtctg gggccaaggg accacggtca ccgtctcctc a            351
```

<210> SEQ ID NO 108
<211> LENGTH: 117
<212> TYPE: PRT
<213> ORGANISM: Artificial
<220> FEATURE:
<223> OTHER INFORMATION: Antibody

<400> SEQUENCE: 108

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Glu Asp Asp Gly Met Asp Val Trp Gly Gln Gly Thr Thr
            100                 105                 110

Val Thr Val Ser Ser
        115
```

<210> SEQ ID NO 109
<211> LENGTH: 336
<212> TYPE: DNA
<213> ORGANISM: Artificial
<220> FEATURE:
<223> OTHER INFORMATION: Antibody

<400> SEQUENCE: 109

```
gatattgtga tgactcagtc tccactctcc ctgcccgtca cccctggaga gccggcctcc    60
atttcctgca ggtctagtca gagcctcctg catagtaatg gatacaacta tttggaatgg   120
tacctgcaga agccagggca gtccccacag ttcatgattt atttgggtc taatcgggcc    180
tccggggtcc ctgacaggtt cagtggcagt ggatcaggca cagatttac actgaaaatc   240
agcagagtgg aggctgagga tgttggggtt tattactgca tgcaagctct acaaactccg   300
atcaccttcg gccaagggac acgactggag attaaa                             336
```

<210> SEQ ID NO 110
<211> LENGTH: 112
<212> TYPE: PRT
<213> ORGANISM: Artificial
<220> FEATURE:
<223> OTHER INFORMATION: Antibody

<400> SEQUENCE: 110

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Glu Trp Tyr Leu Gln Lys Pro Gly Gln Ser
        35                  40                  45

Pro Gln Phe Met Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Ile Thr Phe Gly Gln Gly Thr Arg Leu Glu Ile Lys
            100                 105                 110

<210> SEQ ID NO 111
<211> LENGTH: 366
<212> TYPE: DNA
<213> ORGANISM: Artificial
<220> FEATURE:
<223> OTHER INFORMATION: Antibody

<400> SEQUENCE: 111
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgaggtctgt gactgccgcg gacacggccg tgtattactg tgcgagagcg     300
gattacgatt tttggagtgg ttattttgac tactggggcc agggaaccct ggtcaccgtc     360
tcctca                                                                366

<210> SEQ ID NO 112
<211> LENGTH: 122
<212> TYPE: PRT
<213> ORGANISM: Artificial
<220> FEATURE:
<223> OTHER INFORMATION: Antibody

<400> SEQUENCE: 112

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

```
Gly Gln Gly Thr Leu Val Thr Val Ser Ser
        115                 120
```

<210> SEQ ID NO 113
<211> LENGTH: 322
<212> TYPE: DNA
<213> ORGANISM: Artificial
<220> FEATURE:
<223> OTHER INFORMATION: Antibody

<400> SEQUENCE: 113

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatactt acccgtggac gttcggccaa   300
gggaccaagg tggaaatcaa ac                                            322
```

<210> SEQ ID NO 114
<211> LENGTH: 107
<212> TYPE: PRT
<213> ORGANISM: Artificial
<220> FEATURE:
<223> OTHER INFORMATION: Antibody

<400> SEQUENCE: 114

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105
```

<210> SEQ ID NO 115
<211> LENGTH: 372
<212> TYPE: DNA
<213> ORGANISM: Artificial
<220> FEATURE:
<223> OTHER INFORMATION: Antibody

<400> SEQUENCE: 115

```
caggtgcagc tgcaggagtc gggcccagga ctggtgaagc cttcggagac cctgtccctc    60
acctgcactg tctctggtgg ctccgtcagc agtggtggtt actactggag ctggatccgg   120
cagcccccag gaagggact ggagtggatt gggtatatct attacagtgg gagcaccaac   180
tacaacccct ccctcaagag tcgagtcacc atatcagtag acacgtccaa gaaccagttc   240
tccctgaagc tgagctctgt gaccgctgcg gacacggccg tgtattactg tgcgagagat   300
ggggacgtgg atacagctat ggtcgatgct tttgatatct ggggccaagg acaatggtc   360
accgtctcct ca                                                       372
```

```
<210> SEQ ID NO 116
<211> LENGTH: 124
<212> TYPE: PRT
<213> ORGANISM: Artificial
<220> FEATURE:
<223> OTHER INFORMATION: Antibody

<400> SEQUENCE: 116
```

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Gly Tyr Tyr Trp Ser Trp Ile Arg Gln Pro Pro Gly Lys Gly Leu Glu
        35                  40                  45

Trp Ile Gly Tyr Ile Tyr Tyr Ser Gly Ser Thr Asn Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Asp Val Asp Thr Ala Met Val Asp Ala Phe Asp
            100                 105                 110

Ile Trp Gly Gln Gly Thr Met Val Thr Val Ser Ser
        115                 120

```
<210> SEQ ID NO 117
<211> LENGTH: 324
<212> TYPE: DNA
<213> ORGANISM: Artificial
<220> FEATURE:
<223> OTHER INFORMATION: Antibody

<400> SEQUENCE: 117
```

| | | | | | |
|---|---|---|---|---|---|
| gaaattgtat | tgacgcagtc | tccaggcacc | ctgtctttgt | ctccagggga | aagagccacc | 60 |
| ctctcctgca | gggccagtca | gagtttaagc | ggcaactact | tagcctggta | ccagcagaag | 120 |
| cctggccagg | ctcccaggct | catcatctgt | ggtgcatcca | gcagggccac | tggcatccca | 180 |
| gacaggttca | gtggcagtgg | gtctgggaca | gacttcactc | tcaccatcac | aagactggag | 240 |
| cctgaagatt | ttgcagtgta | ttactgtcag | cagtatgata | ggtcaccgct | cactttcggc | 300 |
| ggagggacca | aggtggagat | caaa | | | | 324 |

```
<210> SEQ ID NO 118
<211> LENGTH: 108
<212> TYPE: PRT
<213> ORGANISM: Artificial
<220> FEATURE:
<223> OTHER INFORMATION: Antibody

<400> SEQUENCE: 118
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Gly Asn
            20                  25                  30

Tyr Leu Ala Trp Tyr Gln Gln Lys Pro Gly Gln Ala Pro Arg Leu Ile
        35                  40                  45

Ile Cys Gly Ala Ser Ser Arg Ala Thr Gly Ile Pro Asp Arg Phe Ser
    50                  55                  60

```
Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Arg Ser Pro
                85                  90                  95

Leu Thr Phe Gly Gly Gly Thr Lys Val Glu Ile Lys
            100                 105

<210> SEQ ID NO 119
<211> LENGTH: 366
<212> TYPE: DNA
<213> ORGANISM: Artificial
<220> FEATURE:
<223> OTHER INFORMATION: Antibody

<400> SEQUENCE: 119
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagga     300
gattacgatt tttggagtgg agagtttgac tactggggcc agggaaccct ggtcaccgtc     360
tcctca                                                                366

<210> SEQ ID NO 120
<211> LENGTH: 122
<212> TYPE: PRT
<213> ORGANISM: Artificial
<220> FEATURE:
<223> OTHER INFORMATION: Antibody

<400> SEQUENCE: 120

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Asp Tyr Asp Phe Trp Ser Gly Glu Phe Asp Tyr Trp
            100                 105                 110

Gly Gln Gly Thr Leu Val Thr Val Ser Ser
        115                 120

<210> SEQ ID NO 121
<211> LENGTH: 386
<212> TYPE: DNA
<213> ORGANISM: Artificial
<220> FEATURE:
<223> OTHER INFORMATION: Antibody

<400> SEQUENCE: 121
caggtgcagc tgcaggagtc gggcccagga ctggtgaagc cttcacagac cctgtccctc      60
```

```
acctgcactg tctctggtgg ctccatcagc agtggtggtt actactggag ctggatccgc      120
cagcacccag ggaagggcct ggagtggatt gggtacatct atgacagtgg agcacctac      180 tacaacccgt ccctcaagag tcgagttacc atatcagtag acacgtctaa gaaccagttc      240
tccctgaagc tgaggtctgt gactgccgcg gacacggccg tgtattactg tgcgagagat      300
caggggcagg acggatacag ctatggttac ggctactact acggtatgga cgtctggggc      360
caagggacca cggtcaccgt ctcctc                                           386

<210> SEQ ID NO 122
<211> LENGTH: 128
<212> TYPE: PRT
<213> ORGANISM: Artificial
<220> FEATURE:
<223> OTHER INFORMATION: Antibody

<400> SEQUENCE: 122

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Asp Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Arg Ser Val Thr Ala Ala Asp Thr Ala Val Tyr Tyr
                85                  90                  95

Cys Ala Arg Asp Gln Gly Gln Asp Gly Tyr Ser Tyr Gly Tyr Gly Tyr
            100                 105                 110

Tyr Tyr Gly Met Asp Val Trp Gly Gln Gly Thr Thr Val Thr Val Ser
        115                 120                 125

<210> SEQ ID NO 123
<211> LENGTH: 321
<212> TYPE: DNA
<213> ORGANISM: Artificial
<220> FEATURE:
<223> OTHER INFORMATION: Antibody

<400> SEQUENCE: 123
gacatccaga tgacccagtc tccatcctcc ctgtctgcat ctgtaggaga cagagtcacc      60
atcacttgcc aggcgagtca ggacattagc aattatttaa attggtatca gcagaaacca      120
gggaaagccc ctaaactcct gatctacgtt gcatccaatt tggaaacagg gtcccatca      180 aggttcagtg gaagtggatc tgggacagat tttactttca ccatcagcag cctgcagcct      240
gaagatattg caacatatta ctgtcaacag tgtgataatc tccctctcac tttcggcgga      300
gggaccaagg tggagatcaa a                                                321

<210> SEQ ID NO 124
<211> LENGTH: 107
<212> TYPE: PRT
<213> ORGANISM: Artificial
<220> FEATURE:
<223> OTHER INFORMATION: Antibody

<400> SEQUENCE: 124

Asp Ile Gln Met Thr Gln Ser Pro Ser Ser Leu Ser Ala Ser Val Gly
```

```
   1               5                  10                 15
Asp Arg Val Thr Ile Thr Cys Gln Ala Ser Gln Asp Ile Ser Asn Tyr
                20                 25                 30

Leu Asn Trp Tyr Gln Gln Lys Pro Gly Lys Ala Pro Lys Leu Leu Ile
                35                 40                 45

Tyr Val Ala Ser Asn Leu Glu Thr Gly Val Pro Ser Arg Phe Ser Gly
                50                 55                 60

Ser Gly Ser Gly Thr Asp Phe Thr Phe Thr Ile Ser Ser Leu Gln Pro
 65                 70                 75                 80

Glu Asp Ile Ala Thr Tyr Tyr Cys Gln Gln Cys Asp Asn Leu Pro Leu
                85                 90                 95

Thr Phe Gly Gly Gly Thr Lys Val Glu Ile Lys
                100                105
```

<210> SEQ ID NO 125
<211> LENGTH: 365
<212> TYPE: DNA
<213> ORGANISM: Artificial
<220> FEATURE:
<223> OTHER INFORMATION: Antibody

<400> SEQUENCE: 125

```
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt ggatacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaaccct ggtcaccgtc     360
tcctc                                                                 365
```

<210> SEQ ID NO 126
<211> LENGTH: 121
<212> TYPE: PRT
<213> ORGANISM: Artificial
<220> FEATURE:
<223> OTHER INFORMATION: Antibody

<400> SEQUENCE: 126

```
Gln Val Gln Leu Gln Glu Ser Gly Pro Gly Leu Val Lys Pro Ser Gln
 1               5                  10                 15

Thr Leu Ser Leu Thr Cys Thr Val Ser Gly Gly Ser Ile Ser Ser Gly
                20                 25                 30

Asp Tyr Tyr Trp Ser Trp Ile Arg Gln His Pro Gly Lys Gly Leu Glu
                35                 40                 45

Trp Ile Gly Tyr Ile Tyr Tyr Ser Gly Ser Thr Tyr Tyr Asn Pro Ser
                50                 55                 60

Leu Lys Ser Arg Val Thr Ile Ser Val Asp Thr Ser Lys Asn Gln Phe
 65                 70                 75                 80

Ser Leu Lys Leu Ser Ser Val Thr Ala Ala Asp Thr Ala Val Tyr Tyr
                85                 90                 95

Cys Ala Arg Ala Asp Tyr Asp Phe Trp Ser Gly Tyr Phe Asp Tyr Trp
                100                105                110

Gly Gln Gly Thr Leu Val Thr Val Ser
                115                120
```

<210> SEQ ID NO 127
<211> LENGTH: 322
<212> TYPE: DNA
<213> ORGANISM: Artificial
<220> FEATURE:
<223> OTHER INFORMATION: Antibody

<400> SEQUENCE: 127

```
gacatccaga tgacccagtc tccatcctcc ctgtctgcat ctgtaggaga cagagtcacc    60
atcacttgcc gggcaagtca ggacattaga aatgatttag ctggtatcg gcagaaacct   120
gggaaagccc ctaagcgcct gatctatgct gcatcccgtt tgcaaagtgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322
```

<210> SEQ ID NO 128
<211> LENGTH: 107
<212> TYPE: PRT
<213> ORGANISM: Artificial
<220> FEATURE:
<223> OTHER INFORMATION: Antibody

<400> SEQUENCE: 128

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Ile Arg Asn Asp
            20                  25                  30
Leu Gly Trp Tyr Arg Gln Lys Pro Gly Lys Ala Pro Lys Arg Leu Ile
        35                  40                  45
Tyr Ala Ala Ser Arg Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys
            100                 105

<210> SEQ ID NO 129
<211> LENGTH: 366
<212> TYPE: DNA
<213> ORGANISM: Artificial
<220> FEATURE:
<223> OTHER INFORMATION: Antibody

<400> SEQUENCE: 129

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcc   300
gattacgatt tttggagtgg ttattttgac tactggggcc agggaaccct ggtcaccgtc   360
tcctca                                                              366
```

<210> SEQ ID NO 130
<211> LENGTH: 122

<212> TYPE: PRT
<213> ORGANISM: Artificial
<220> FEATURE:
<223> OTHER INFORMATION: Antibody

<400> SEQUENCE: 130

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 131
<211> LENGTH: 322
<212> TYPE: DNA
<213> ORGANISM: Artificial
<220> FEATURE:
<223> OTHER INFORMATION: Antibody

<400> SEQUENCE: 131
gacatccaga tgacccagtc tccatcctcc ctgtctgcat ctgtaggaga cagagtcacc    60
atcacttgcc gggcaagtca gggcattaga aatgatttag ctggtatca gcagaaacca   120 gggaaagccc ctaagcgcct gatctatgct gcatccagtt tgcaaaatgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322

<210> SEQ ID NO 132
<211> LENGTH: 107
<212> TYPE: PRT
<213> ORGANISM: Artificial
<220> FEATURE:
<223> OTHER INFORMATION: Antibody

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Asn Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp 85                  90                  95
Thr Phe Gly Gln Gly Thr Lys Val Glu Ile Lys
            100                 105

<210> SEQ ID NO 133
<211> LENGTH: 365
<212> TYPE: DNA
<213> ORGANISM: Artificial
<220> FEATURE:
<223> OTHER INFORMATION: Antibody

<400> SEQUENCE: 133
caggtgcagc tgcaggagtc gggcccagga ctggtgaagc cttcacagac cctgtccctc      60
acctgcactg tctctggtgg ctccatcagc agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tactggggcc agggaatcct ggtcaccgtc     360
tcctc                                                                 365

<210> SEQ ID NO 134
<211> LENGTH: 121
<212> TYPE: PRT
<213> ORGANISM: Artificial
<220> FEATURE:
<223> OTHER INFORMATION: Antibody

<400> SEQUENCE: 134

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser
        115                 120

<210> SEQ ID NO 135
<211> LENGTH: 322
<212> TYPE: DNA
<213> ORGANISM: Artificial
<220> FEATURE:
<223> OTHER INFORMATION: Antibody

<400> SEQUENCE: 135
gacatccaga tgacccagtc tccatcctcc ctgtctgcat ctgtaggaga cagagtcacc      60
atcacttgcc gggcaagtca gggcattaga aatgatttag gctggtatca gcagaaacca     120
gggaaagccc ctaagcgcct gatttatgct gcatccagtt tgcaaagtgg ggtcccatca     180

```
aggttcagcg gcagtggatc tgggacagaa ttcactctca caatcagcag cctgcagcct      240
gaagattttg caacttatta ctgtctacag cataatagtt acccgtggac gttcggccaa      300
gggaccaagg tggaaatcaa ac                                               322
```

<210> SEQ ID NO 136
<211> LENGTH: 107
<212> TYPE: PRT
<213> ORGANISM: Artificial
<220> FEATURE:
<223> OTHER INFORMATION: Antibody

<400> SEQUENCE: 136

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105
```

<210> SEQ ID NO 137
<211> LENGTH: 366
<212> TYPE: DNA
<213> ORGANISM: Artificial
<220> FEATURE:
<223> OTHER INFORMATION: Antibody

<400> SEQUENCE: 137

```
caggtgcagc tgcaggagtc gggcccagga ctggtgaagc cttcacagac cctgtccctc       60
acctgcactg tctctggtgg ctccatcagt agtggtgatt actactggag ctggatccgc      120
cagcacccag ggaagggcct ggagtggatt gggtacatct attacagtgg gagcacctac      180
tacaacccgt ccctcaagag tcgagttacc atatcagtag acacgtctaa gaaccagttc      240
tccctgaagt tgagctctgt gactgccgcg gacacggccg tgtattactg tgcgagagcc      300
gattacgatt tttggaatgg ttattttgac tactggggcc agggaaccct ggtcaccgtc      360
tcctca                                                                 366
```

<210> SEQ ID NO 138
<211> LENGTH: 122
<212> TYPE: PRT
<213> ORGANISM: Artificial
<220> FEATURE:
<223> OTHER INFORMATION: Antibody

<400> SEQUENCE: 138

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45
```

```
Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
            115                 120
```

<210> SEQ ID NO 139
<211> LENGTH: 321
<212> TYPE: DNA
<213> ORGANISM: Artificial
<220> FEATURE:
<223> OTHER INFORMATION: Antibody

<400> SEQUENCE: 139

```
gacatccaga tgacccagtc tccatcctcc ctgtctgcat ctgtaggaga cagagtcacc    60
atcacttgcc gggcaagtca gggcattaga aatgatttag ctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataataatt acccgtggac gttcggccaa   300
gggaccaagg tggaaatcaa a                                             321
```

<210> SEQ ID NO 140
<211> LENGTH: 107
<212> TYPE: PRT
<213> ORGANISM: Artificial
<220> FEATURE:
<223> OTHER INFORMATION: Antibody

<400> SEQUENCE: 140

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Asn Tyr Pro Trp
                 85                  90                  95

Thr Phe Gly Gln Gly Thr Lys Val Glu Ile Lys
            100                 105
```

<210> SEQ ID NO 141
<211> LENGTH: 366
<212> TYPE: DNA
<213> ORGANISM: Artificial
<220> FEATURE:
<223> OTHER INFORMATION: Antibody

<400> SEQUENCE: 141

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagcacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgagctctgt gactgccgcg gacacggccg tgtattactg tgcgagagcc   300
gattacgatt tttggagtgg ttattttgac tactggggcc agggaaccct ggtcaccgtc   360
tcctca                                                              366
```

<210> SEQ ID NO 142
<211> LENGTH: 122
<212> TYPE: PRT
<213> ORGANISM: Artificial
<220> FEATURE:
<223> OTHER INFORMATION: Antibody

<400> SEQUENCE: 142

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120
```

<210> SEQ ID NO 143
<211> LENGTH: 322
<212> TYPE: DNA
<213> ORGANISM: Artificial
<220> FEATURE:
<223> OTHER INFORMATION: Antibody

<400> SEQUENCE: 143

```
gacatccagc tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaaatgg ggtcccatca   180
aggttcagcg gcagtggatc tgggacagaa ttcactctca caatcagcag cctgcagcct   240
gaagattttg caacttatta ctgtctacag cataatagtt acccgtggac gttcggccaa   300
gggaccaagg tggaaatcaa ac                                            322
```

<210> SEQ ID NO 144
<211> LENGTH: 107
<212> TYPE: PRT
<213> ORGANISM: Artificial
<220> FEATURE:
<223> OTHER INFORMATION: Antibody

<400> SEQUENCE: 144

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Lys Pro Gly Lys Ala Pro Lys Arg Leu Ile
        35                  40                  45

Tyr Ala Ala Ser Ser Leu Gln Asn Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 145
<211> LENGTH: 365
<212> TYPE: DNA
<213> ORGANISM: Artificial
<220> FEATURE:
<223> OTHER INFORMATION: Antibody

<400> SEQUENCE: 145
caggtgcagc tgcaggagtc gggcccagga ctggtgaagc cttcacagac cctgtccctc      60
acctgcactg tctctggtgg ctccatcagc agtggtgatt actactggag ctggatccgc     120
cagtacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgggctctgt gactgccgcg gacacggccg tgtatttctg tgcgagagcc     300
gattacgatt tttggagtgg ttattttgac ttctggggcc agggaaccct ggtcaccgtc     360
tcctc                                                                 365

<210> SEQ ID NO 146
<211> LENGTH: 121
<212> TYPE: PRT
<213> ORGANISM: Artificial
<220> FEATURE:
<223> OTHER INFORMATION: Antibody

<400> SEQUENCE: 146

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
            115                 120

<210> SEQ ID NO 147
<211> LENGTH: 322
<212> TYPE: DNA
<213> ORGANISM: Artificial
<220> FEATURE:
<223> OTHER INFORMATION: Antibody

<400> SEQUENCE: 147

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt acccgtggac gttcggccaa   300
gggaccaagg tggaaatcaa ac                                            322
```

<210> SEQ ID NO 148
<211> LENGTH: 107
<212> TYPE: PRT
<213> ORGANISM: Artificial
<220> FEATURE:
<223> OTHER INFORMATION: Antibody

<400> SEQUENCE: 148

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Leu Gln His Asn Gly Tyr Pro Trp
                85                  90                  95
Thr Phe Gly Gln Gly Thr Lys Val Glu Ile Lys
            100                 105
```

<210> SEQ ID NO 149
<211> LENGTH: 365
<212> TYPE: DNA
<213> ORGANISM: Artificial
<220> FEATURE:
<223> OTHER INFORMATION: Antibody

<400> SEQUENCE: 149

```
caggtgcagc tgcaggagtc gggcccagga ctggtgaagc cttcacagac cctgtccctc    60
acctgcactg tctctggtgg ctccatcagc agtggtgatt actactggag ctggatccgc   120
cagtacccag ggaagggcct ggagtggatt gggtacatct attacagtgg gagcacctac   180
tacaacccgt ccctcaagag tcgagttacc atatcagtag acacgtctaa gaaccagttc   240
tccctgaagc tgggctctgt gactgccgcg gacacggccg tgtatttctg tgcgagagcc   300
gattacgatt ttggagtggt tattttgac ttctggggcc agggaaccct ggtcaccgtc   360
tcctc                                                              365
```

<210> SEQ ID NO 150
<211> LENGTH: 121
<212> TYPE: PRT
<213> ORGANISM: Artificial
<220> FEATURE:
<223> OTHER INFORMATION: Antibody

<400> SEQUENCE: 150

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln Tyr Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Gly Ser Val Thr Ala Ala Asp Thr Ala Val Tyr Phe
                85                  90                  95

Cys Ala Arg Ala Asp Tyr Asp Phe Trp Ser Gly Tyr Phe Asp Phe Trp
            100                 105                 110

Gly Gln Gly Thr Leu Val Thr Val Ser
        115                 120
```

<210> SEQ ID NO 151
<211> LENGTH: 322
<212> TYPE: DNA
<213> ORGANISM: Artificial
<220> FEATURE:
<223> OTHER INFORMATION: Antibody

<400> SEQUENCE: 151

```
gacatccaga tgacccagtc tccatcctcc ctgtctgcat ctgtaggaga cagagtcacc    60
atcacttgcc gggcaagtca gggcattaga aatgatttag gctggtatca gcagaaacca   120
gggaaagccc ctaagcgcct gatctatgct gcatccagtt tgcaaagtgg ggtcccatca   180
aggttcagcg gcagtggatc tgggacagaa ttcactctca caatcagcag cctgcagcct   240
gaagattttg caacttatta ctgtctacag cataatggtt acccgtggac gttcggccaa   300
gggaccaagg tggaaatcaa ac                                            322
```

<210> SEQ ID NO 152
<211> LENGTH: 107
<212> TYPE: PRT
<213> ORGANISM: Artificial
<220> FEATURE:
<223> OTHER INFORMATION: Antibody

<400> SEQUENCE: 152

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Glu Asp Phe Ala Thr Tyr Tyr Cys Leu Gln His Asn Gly Tyr Pro Trp
             85                  90                  95

Thr Phe Gly Gln Gly Thr Lys Val Glu Ile Lys
            100                 105

<210> SEQ ID NO 153
<211> LENGTH: 366
<212> TYPE: DNA
<213> ORGANISM: Artificial
<220> FEATURE:
<223> OTHER INFORMATION: Antibody

<400> SEQUENCE: 153
caggtgcagc tgcaggagtc gggcccagga ctggtgaagc cttcacagac cctgtccctc      60
acctgcactg tctctggtgg ctccatcagt agtggtgatt actactggag ctggatccgc     120
cagcacccag ggaagggcct ggagtggatt gggtacatct attacagtgg gagcacctac     180
tacaacccgt ccctcaagag tcgagttacc atatcagtag acacgtctaa gaaccagttc     240
tccctgaagc tgagctctgt gactgccgcg gacacggccg tgtattactg tgcgagagcg     300
gattacgatt tttggagtgg ttattttgac tcctggggcc agggaaccct ggtcaccgtc     360
tcctca                                                                366

<210> SEQ ID NO 154
<211> LENGTH: 122
<212> TYPE: PRT
<213> ORGANISM: Artificial
<220> FEATURE:
<223> OTHER INFORMATION: Antibody

<400> SEQUENCE: 154

Gln Val Gln Leu Gln Glu Ser Gly Pro Gly Leu Val Lys Pro Ser Gln
1               5                  10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Ser Trp
            100                 105                 110

Gly Gln Gly Thr Leu Val Thr Val Ser Ser
        115                 120

<210> SEQ ID NO 155
<211> LENGTH: 321
<212> TYPE: DNA
<213> ORGANISM: Artificial
<220> FEATURE:
<223> OTHER INFORMATION: Antibody

<400> SEQUENCE: 155
gacatccaga tgacccagtc tccatcctcc ctgtctgcat ctgtaggaga cagagtcacc      60
atcacttgcc gggcaagtca gggcattaga aatgatttag gctggtatca gcagatacct     120
```

```
gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatggtt acccgtggac gttcggccaa    300
gggaccaagg tggaaatcaa a                                              321
```

<210> SEQ ID NO 156
<211> LENGTH: 107
<212> TYPE: PRT
<213> ORGANISM: Artificial
<220> FEATURE:
<223> OTHER INFORMATION: Antibody

<400> SEQUENCE: 156

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Ile Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Gly Tyr Pro Trp
                85                  90                  95

Thr Phe Gly Gln Gly Thr Lys Val Glu Ile Lys
            100                 105
```

<210> SEQ ID NO 157
<211> LENGTH: 366
<212> TYPE: DNA
<213> ORGANISM: Artificial
<220> FEATURE:
<223> OTHER INFORMATION: Antibody

<400> SEQUENCE: 157

```
caggttcagc tggtgcagtc tggagctgag gtgaagaagc ctggggcctc agtgaaggtc     60
tcctgcaagg cttctggtta cacctttacc aactatggta tcagctgggt gcggcaggcc    120
cctggacaag gcttgagtg gatgggatgg atcagcgctt acgatggtta cagaaactat    180
gcacagaagc tccagggcag agtcaccatg accacagaca catccacgac cactgcctac    240
atggagctga ggagcctgag atctgacgac acggccgtgt attactgtgc gagagatgtt    300
caagactacg gtgactacga ctactttgac tactggggcc agggaaccct ggtcaccgtc    360
tcctca                                                               366
```

<210> SEQ ID NO 158
<211> LENGTH: 122
<212> TYPE: PRT
<213> ORGANISM: Artificial
<220> FEATURE:
<223> OTHER INFORMATION: Antibody

<400> SEQUENCE: 158

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30
```

```
Gly Ile Ser Trp Val Arg Gln Ala Pro Gly Gln Gly Leu Glu Trp Met
            35                  40                  45
Gly Trp Ile Ser Ala Tyr Asp Gly Tyr Arg Asn Tyr Ala Gln Lys Leu
 50                      55                  60
Gln Gly Arg Val Thr Met Thr Thr Asp Thr Ser Thr Thr Thr Ala Tyr
 65                  70                  75                  80
Met Glu Leu Arg Ser Leu Arg Ser Asp Thr Ala Val Tyr Tyr Cys
                 85                  90                  95
Ala Arg Asp Val Gln Asp Tyr Gly Tyr Asp Tyr Phe Asp Tyr Trp
            100                 105                 110
Gly Gln Gly Thr Leu Val Thr Val Ser Ser
            115                 120

<210> SEQ ID NO 159
<211> LENGTH: 321
<212> TYPE: DNA
<213> ORGANISM: Artificial
<220> FEATURE:
<223> OTHER INFORMATION: Antibody

<400> SEQUENCE: 159
gacatccaga tgacccagtc tccatcctcc ctgtctgcat ctgtaggaga cagagtcacc      60
atcacttgcc gggcaagtca gagcattagc agttatttaa attggtatca gcagaaacca    120
gggaaagccc ctaacctcct gatctatgct gcatccagtt tgcaaagtgg ggtcccatca    180
agattcaggg gcagtggatc tgggacagat ttcactctca ccatcagcag tctgcaacct    240
gaagattttg caacttacta ctgtcaacag agttacagta cccccatcac cttcggccaa    300
gggacacgac tggagattaa a                                              321

<210> SEQ ID NO 160
<211> LENGTH: 107
<212> TYPE: PRT
<213> ORGANISM: Artificial
<220> FEATURE:
<223> OTHER INFORMATION: Antibody

<400> SEQUENCE: 160

Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Lys Ala Pro Asn Leu Leu Ile
         35                  40                  45
Tyr Ala Ala Ser Ser Leu Gln Ser Gly Val Pro Ser Arg Phe Arg Gly
 50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Ser Thr Pro Ile
                 85                  90                  95
Thr Phe Gly Gln Gly Thr Arg Leu Glu Ile Lys
            100                 105

<210> SEQ ID NO 161
<211> LENGTH: 366
<212> TYPE: DNA
<213> ORGANISM: Artificial
<220> FEATURE:
<223> OTHER INFORMATION: Antibody
```

<400> SEQUENCE: 161

```
caggtgcagc tgcaggagtc gggcccagga ctggtgaagc ctttacagac cctgtccctc    60
acctgcactg tctctggtgg ctccatcagc agtggtgatt actactggag ctggatccgc   120
cagcacccag gaagggcct ggagtggatt gggtacatct attacagtgg gaccacctac   180
tacaacccgt ccctcaagag tcgagttacc atatcagtag acacgtctaa gaaccagttc   240
gccctgaagc tgaactctgt gactgccgcg gacacggccg tgtattactg tgcgagagcc   300
gattacgatt tttggagtgg ttattttgac tactggggcc agggaaccct ggtcaccgtc   360
tcctca                                                             366
```

<210> SEQ ID NO 162
<211> LENGTH: 122
<212> TYPE: PRT
<213> ORGANISM: Artificial
<220> FEATURE:
<223> OTHER INFORMATION: Antibody

<400> SEQUENCE: 162

Gln Val Gln Leu Gln Glu Ser Gly Pro Gly Leu Val Lys Pro Leu Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ala Leu Lys Leu Asn Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 163
<211> LENGTH: 322
<212> TYPE: DNA
<213> ORGANISM: Artificial
<220> FEATURE:
<223> OTHER INFORMATION: Antibody

<400> SEQUENCE: 163

```
gacatccaga tgacccagtc tccatcctcc ctgtctgcat ctgtaggaga cagagtcacc    60
atcacttgcc gggcaggtca gggcattaga aatgatttag ctggtatca gcagaaacca   120
gggaaagccc ctcagcgcct gatctatgct gcatccagtt tgcaaagtgg ggtcccatca   180
aggttcagcg gcagtggatc tgggacagaa ttctctctca caatctccag cctgcagcct   240
gaagattttg caacttatta ctgtctacag cataatagtt acccgtggac gttcggccaa   300
gggaccaagg tggaaatcaa ac                                           322
```

<210> SEQ ID NO 164
<211> LENGTH: 107
<212> TYPE: PRT
<213> ORGANISM: Artificial
<220> FEATURE:
<223> OTHER INFORMATION: Antibody

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Arg Ala Gly Gln Gly Ile Arg Asn Asp
            20                  25                  30

Leu Gly Trp Tyr Gln Gln Lys Pro Gly Lys Ala Pro Gln Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Ser Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 165
<211> LENGTH: 369
<212> TYPE: DNA
<213> ORGANISM: Artificial
<220> FEATURE:
<223> OTHER INFORMATION: Antibody

<400> SEQUENCE: 165
caggtgcagc tggtggagtc tgggggaggc ttggtcaagc ctggagggtc cctgagactc     60
tcctgtgcag cctctggatt caccttcagt gactactaca tgagctggat ccgccaggct    120
ccagggaagg ggctggagtg ggtttcatat attagtagta gtggtaataa catataccac    180
gcagactctg tgaagggccg attcaccatc tccagggaca cgccaagaa ctcactgtat     240
ctgcaaatga acagcctgag agccgaggac acggccgtgt attactgtgc gagagagaga    300
tatagtggct acgacgaccc tgatggtttt gatatctggg gccaagggac aatggtcacc    360
gtctcttca                                                            369

<210> SEQ ID NO 166
<211> LENGTH: 123
<212> TYPE: PRT
<213> ORGANISM: Artificial
<220> FEATURE:
<223> OTHER INFORMATION: Antibody

<400> SEQUENCE: 166

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Asn Asn Ile Tyr His Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Ser Gly Tyr Asp Asp Pro Asp Gly Phe Asp Ile
            100                 105                 110

Trp Gly Gln Gly Thr Met Val Thr Val Ser Ser
        115                  120

<210> SEQ ID NO 167
<211> LENGTH: 321
<212> TYPE: DNA
<213> ORGANISM: Artificial
<220> FEATURE:
<223> OTHER INFORMATION: Antibody

<400> SEQUENCE: 167

```
gacatccaga tgacccagtc tccatcctcc ctgtctgcat ctgtaggaga cagagtcacc      60
atcacttgcc aggcgagtca ggacattagc aactatttaa gttggtttca gcagaaacca    120
gggaaagccc ctaagctcct gatccacgat gcatccaatt tggaaacagg ggtcccttca    180
aggttcagtg gaagtggatc tgggacagat tttactttca ccatcagcag cctgcagcct    240
gaagatattg caacatatta ctgtcaacag tatgataatc ccccgtgcag ttttggccag    300
gggaccaagc tggagatcaa a                                              321
```

<210> SEQ ID NO 168
<211> LENGTH: 107
<212> TYPE: PRT
<213> ORGANISM: Artificial
<220> FEATURE:
<223> OTHER INFORMATION: Antibody

<400> SEQUENCE: 168

Asp Ile Gln Met Thr Gln Ser Pro Ser Ser Leu Ser Ala Ser Val Gly
1             5                  10                 15

Asp Arg Val Thr Ile Thr Cys Gln Ala Ser Gln Asp Ile Ser Asn Tyr
           20                  25                 30

Leu Ser Trp Phe Gln Gln Lys Pro Gly Lys Ala Pro Lys Leu Leu Ile
           35                  40                 45

His Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65              70                  75                 80

Glu Asp Ile Ala Thr Tyr Tyr Cys Gln Gln Tyr Asp Asn Pro Pro Cys
               85                  90                 95

Ser Phe Gly Gln Gly Thr Lys Leu Glu Ile Lys
          100                 105

<210> SEQ ID NO 169
<211> LENGTH: 366
<212> TYPE: DNA
<213> ORGANISM: Artificial
<220> FEATURE:
<223> OTHER INFORMATION: Antibody

<400> SEQUENCE: 169

```
caggtgcagc tgcaggagtc gggcccagga ctggtgaagc cttcacagac cctgtccctc      60
acctgcactg tctctggtgg ctccatcagc agtggttatt actactggag ctggatccgc    120
cagcacccag gaagggcct ggagtggatt ggtacatct attacagtgg gaccacctac    180
tacaatccgt ccttcaagag tcgagttacc atatcagtag acacgtctaa gaaccagttc    240
tccctgaaac tgagctctgt gactgccgcg gacacggccg tgtattactg tgcgagagcc    300
gattacgatt ttggagtgg tcactttgac tactggggcc agggaaccct ggtcaccgtc    360
tcctca                                                              366
```

<210> SEQ ID NO 170
<211> LENGTH: 122
<212> TYPE: PRT
<213> ORGANISM: Artificial
<220> FEATURE:
<223> OTHER INFORMATION: Antibody

<400> SEQUENCE: 170

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Tyr Tyr Tyr Trp Ser Trp Ile Arg Gln His Pro Gly Lys Gly Leu Glu
        35                  40                  45

Trp Ile Gly Tyr Ile Tyr Tyr Ser Gly Thr Thr Tyr Tyr Asn Pro Ser
    50                  55                  60

Phe Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly His Phe Asp Tyr Trp
            100                 105                 110

Gly Gln Gly Thr Leu Val Thr Val Ser Ser
        115                 120

<210> SEQ ID NO 171
<211> LENGTH: 321
<212> TYPE: DNA
<213> ORGANISM: Artificial
<220> FEATURE:
<223> OTHER INFORMATION: Antibody

<400> SEQUENCE: 171
gacatccaga tgacccagtc tccatcctcc ctgtctgcat ctgtaggaga cagagtcacc      60
atcacttgcc gggcaagtca gggcattaga aatgatttag ctggtatca gcagaaacca     120 gggaaagccc ctaagcgcct gatctatgct gcatccagtt tgcaaagtgg ggtcccatca    180
aggttcagcg gcagtggatc tgggacagaa ttcactctca caatcagcag cctgcagcct    240
gaagattttg caacttatta ctgtctacag cataatagtt acccgtggac gttcggccaa    300
gggaccaagg tggaaatcaa a                                              321

<210> SEQ ID NO 172
<211> LENGTH: 107
<212> TYPE: PRT
<213> ORGANISM: Artificial
<220> FEATURE:
<223> OTHER INFORMATION: Antibody

<400> SEQUENCE: 172

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

```
Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

```
<210> SEQ ID NO 173
<211> LENGTH: 365
<212> TYPE: DNA
<213> ORGANISM: Artificial
<220> FEATURE:
<223> OTHER INFORMATION: Antibody

<400> SEQUENCE: 173
caggttcagc tggtgcagtc tggagctgag gtgaagaagc ctggggcctc agtgaaggtc      60
tcctgcaagg cttctggtta cacctttacc agctatggta tcagctgggt gcgacaggcc    120
cctggacaag acttgagtg gatgggatgg atcagcgctt acgatggtca cacaaactat     180
gcacagaagc tccagggcag agtcaccatg accacagaca catccacgaa cacagcctac    240
atggagctga ggagcctgag atctgacgac acggccgttt attactgtgc gagagacccc    300
catgactaca gtaactacga ggcttttgac ttctggggcc agggaaccct ggtcaccgtc    360
tcctc                                                                365
```

```
<210> SEQ ID NO 174
<211> LENGTH: 121
<212> TYPE: PRT
<213> ORGANISM: Artificial
<220> FEATURE:
<223> OTHER INFORMATION: Antibody

<400> SEQUENCE: 174

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Ser Tyr
                 20                  25                  30

Gly Ile Ser Trp Val Arg Gln Ala Pro Gly Gln Gly Leu Glu Trp Met
             35                  40                  45

Gly Trp Ile Ser Ala Tyr Asp Gly His Thr Asn Tyr Ala Gln Lys Leu
 50                  55                  60

Gln Gly Arg Val Thr Met Thr Thr Asp Thr Ser Thr Asn Thr Ala Tyr
 65                  70                  75                  80

Met Glu Leu Arg Ser Leu Arg Ser Asp Asp Thr Ala Val Tyr Tyr Cys
                 85                  90                  95

Ala Arg Asp Pro His Asp Tyr Ser Asn Tyr Glu Ala Phe Asp Phe Trp
            100                 105                 110

Gly Gln Gly Thr Leu Val Thr Val Ser
        115                 120
```

```
<210> SEQ ID NO 175
<211> LENGTH: 519
<212> TYPE: DNA
<213> ORGANISM: Artificial
<220> FEATURE:
<223> OTHER INFORMATION: Antibody

<400> SEQUENCE: 175
atgaggtccc ctgctcagct cctggggctc ctgctactct ggctccgagg tgccagatgt       60
```

```
gacatccaga tgacccagtc tccatcctcc ctgtctgcat ctgtaggaga cagagtcacc    120
atcacttgcc gggcaagtca gagcattagc agttatttaa attggtatca gcagaaacca    180
gggaaagccc ctaacctcct gatctatgct gcatccagtt tgcaaagtgg ggtcccatca    240
agattcagtg gcagtggatc tgggacagat tcactctca ccatcagcag tctgcaacct    300
gaagattttg caacttacta ctgtcaacag agttacagta ccccatcac cttcggccaa    360 gggacacgac tggagattaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgcc                          519
```

```
<210> SEQ ID NO 176
<211> LENGTH: 107
<212> TYPE: PRT
<213> ORGANISM: Artificial
<220> FEATURE:
<223> OTHER INFORMATION: Antibody

<400> SEQUENCE: 176

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105
```

```
<210> SEQ ID NO 177
<211> LENGTH: 534
<212> TYPE: DNA
<213> ORGANISM: Artificial
<220> FEATURE:
<223> OTHER INFORMATION: Antibody

<400> SEQUENCE: 177
accatggact ggacctggag ggtccttttc ttggtggcag cagcaacagg tgcccactcc     60
caggttcagc tggtgcagtc tggagctgag gtgaagaagc ctggggcctc agtgaaggtc    120
tcctgcaagg cttctggtta caccttacc aactatggta tcagctgggt gcggcaggcc    180
cctggacaag gcttgagtg gatgggatgg atcagcgctt acgatggtta cagaaactat    240
gcacagaagc tccagggcag agtcaccatg accacagaca catccacgac cactgcctac    300
atggagctga ggagcctgag atctgacgac acggccgtgt attactgtgc gagagatgtt    360
caagactacg gtgactacga ctactttgac tactggggcc agggaaccct ggtcaccgtc    420
tcctcagctt ccaccaaggg cccatccgtc ttccccctgg tgccctgctc aggagcacc    480 tccgagagca gccgccct gggctgcctg gtcaaggact acttcccga accg            534
```

```
<210> SEQ ID NO 178
<211> LENGTH: 122
<212> TYPE: PRT
```

<213> ORGANISM: Artificial
<220> FEATURE:
<223> OTHER INFORMATION: Antibody

<400> SEQUENCE: 178

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asp Gly Tyr Arg Asn Tyr Ala Gln Lys Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Val Gln Asp Tyr Gly Asp Tyr Asp Tyr Phe Asp Tyr Trp
            100                 105                 110

Gly Gln Gly Thr Leu Val Thr Val Ser Ser
        115                 120

<210> SEQ ID NO 179
<211> LENGTH: 504
<212> TYPE: DNA
<213> ORGANISM: Artificial
<220> FEATURE:
<223> OTHER INFORMATION: Antibody

<400> SEQUENCE: 179

```
cagctcctgg ggctcctgct actctggctc cgaggtgcca gatgtgacat ccagatgacc      60
cagtctccat cctccctgtc tgcatctgta ggagacagag tcaccatcac ttgccgggca     120
agtcagagca ttagcagtta tttaaattgg tatcagcaga accagggaaa gcccctaac     180
ctcctgatct atgctgcatc cagtttgcaa agtggggtcc catcaagatt cagtggcagt     240
ggatctggga cagatttcac tctcaccatc agcagtctgc aacctgaaga ttttgcaact     300
tactactgtc aacagagtta cagtaccccc atcaccttcg gccagggac acgactggag      360
attaaacgaa ctgtggctgc accatctgtc ttcatcttcc cgccatctga tgagcagttg     420
aaatctggaa ctgcctctgt tgtgtgcctg ctgaataact tctatcccag agaggccaaa     480
gtacagtgga aggtggataa cgcc                                             504
```

<210> SEQ ID NO 180
<211> LENGTH: 107
<212> TYPE: PRT
<213> ORGANISM: Artificial
<220> FEATURE:
<223> OTHER INFORMATION: Antibody

<400> SEQUENCE: 180

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 181
<211> LENGTH: 493
<212> TYPE: DNA
<213> ORGANISM: Artificial
<220> FEATURE:
<223> OTHER INFORMATION: Antibody

<400> SEQUENCE: 181
catctgtggt tcttcctcct gctggtggca gctcccagat gggtcctgtc ccaggtgcag    60
ctgcaggagt cgggcccagg actggtgaag ccttcacaga ccctgtccct cacctgcact   120
gtctctggtg ctccatcaa cagtggtgat tactactgga gctggatccg ccagcaccca   180
gggaagggcc tggagtggat tgggtacatc tattacagtg ggagcaccta ctacaacccg   240
tccctcaaga gtcgagttac catatcagta gacacgtcta agaaccagtt ctccctgaag   300
ctgagctctg tgactgccgc ggacacggcc gtgtattact gtgcgagagc agattacgat   360
ttttggagtg gttactttga ctactggggc cagggaaccc tggtcaccgt ctcctcagcc   420
tccaccaagg gcccatcggt cttccccctg gcaccctcct ccaagagcac ctctgggggc   480
acaacggccc tgg                                                     493

<210> SEQ ID NO 182
<211> LENGTH: 122
<212> TYPE: PRT
<213> ORGANISM: Artificial
<220> FEATURE:
<223> OTHER INFORMATION: Antibody

<400> SEQUENCE: 182

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Asn Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 183
<211> LENGTH: 518
<212> TYPE: DNA
<213> ORGANISM: Artificial
<220> FEATURE:
<223> OTHER INFORMATION: Antibody

<400> SEQUENCE: 183

```
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag ctggtatca gcagaaacca   180
gggaaagccc ctaagcgcct gatctatgct gcatccagtt tgcaaagtgg ggtcccatca   240
aggttcagcg gcagtggatc tgggacagaa ttcactctca caatcagcag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgc                           518
```

<210> SEQ ID NO 184
<211> LENGTH: 107
<212> TYPE: PRT
<213> ORGANISM: Artificial
<220> FEATURE:
<223> OTHER INFORMATION: Antibody

<400> SEQUENCE: 184

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105
```

<210> SEQ ID NO 185
<211> LENGTH: 436
<212> TYPE: DNA
<213> ORGANISM: Artificial
<220> FEATURE:
<223> OTHER INFORMATION: Antibody

<400> SEQUENCE: 185

```
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tggttactac tggagctgga tccgccagca cccagggaag   180
ggcctggagt ggattgggta catctattac agtgggagca cctactacaa cccgtccctc   240
aagagtcgag ttaccatatc agtagacacg tctaagaacc agttctccct gaagctgagc   300
tctgtgactg ccgcggacac ggccgtgtat tactgtgcga gagatggcta tgatagtagt   360
ggttattacc acggctactt tgactactgg ggccagggaa ccctggtcac cgtctcctca   420
gcctccacca agggcc                                                   436
```

<210> SEQ ID NO 186
<211> LENGTH: 125
<212> TYPE: PRT
<213> ORGANISM: Artificial
<220> FEATURE:
<223> OTHER INFORMATION: Antibody

<400> SEQUENCE: 186

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gly Tyr Asp Ser Ser Gly Tyr Tyr His Gly Tyr Phe
            100                 105                 110

Asp Tyr Trp Gly Gln Gly Thr Leu Val Thr Val Ser Ser
        115                 120                 125

<210> SEQ ID NO 187
<211> LENGTH: 521
<212> TYPE: DNA
<213> ORGANISM: Artificial
<220> FEATURE:
<223> OTHER INFORMATION: Antibody

<400> SEQUENCE: 187
caggtcttca tttctctgtt gctctggatc tctggtgcct acggggacat cgtgatgacc      60
cagtctccag actccctggc tgtgtctctg ggcgagaggg ccaccatcaa ctgcaagtcc     120
agccagagtg ttttatacag ctccaacaat aagaactact tagcttggta ccagcagaaa     180
ccaggacagc ctcctaagct gctcatttac tgggcatcta cccgggaatc cggggtccct     240
gaccgattca gtggcagcgg gtctgggaca gatttcactc tcaccatcag cagcctgcag     300
gctgaagatg tggcagttta ttactgtcag caatattata gtactccgct cactttcggc     360
ggagggacca aggtggagat caaacgaact gtggctgcac catctgtctt catcttcccg     420
ccatctgatg agcagttgaa atctggaact gcctctgttg tgtgcctgct gaataacttc     480
tatcccagag aggccaaagt acagtggaag gtggataacg c                         521

<210> SEQ ID NO 188
<211> LENGTH: 113
<212> TYPE: PRT
<213> ORGANISM: Artificial
<220> FEATURE:
<223> OTHER INFORMATION: Antibody

<400> SEQUENCE: 188

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
            50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Leu Thr Phe Gly Gly Gly Thr Lys Val Glu Ile
                100                 105                 110

Lys

<210> SEQ ID NO 189
<211> LENGTH: 455
<212> TYPE: DNA
<213> ORGANISM: Artificial
<220> FEATURE:
<223> OTHER INFORMATION: Antibody

<400> SEQUENCE: 189
ctgtggttct tcctcctgct ggtggcagct cccagatggg tcctgtccca ggtgcagctg      60
caggagtcgg gcccaggact ggtgaagcct tcacagaccc tgtccctcac ctgcactgtc     120
tctggtggct ccatcagtag tggtgattac tactggagct ggatccgcca gcacccaggg     180
aagggcctgg agtggattgg gtacatctat acagtggga gcacctacta caacccgtcc      240
ctcaagagtc gagttaccat atcagtagac acgtctaaga accagttctc cctgaagttg     300
agctctgtga ctgccgcgga cacggccgtg tattactgtg cgagagccga ttacgatttt     360
tggagtggtt attttgacta ctggggccag ggaaccctgg tcaccgtctc ctcagcctcc     420
accaagggcc catcggtctt ccccctggca ccctc                                455

<210> SEQ ID NO 190
<211> LENGTH: 122
<212> TYPE: PRT
<213> ORGANISM: Artificial
<220> FEATURE:
<223> OTHER INFORMATION: Antibody

<400> SEQUENCE: 190

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
                100                 105                 110

Gly Gln Gly Thr Leu Val Thr Val Ser Ser
            115                 120

<210> SEQ ID NO 191
<211> LENGTH: 442
<212> TYPE: DNA

```
<213> ORGANISM: Artificial
<220> FEATURE:
<223> OTHER INFORMATION: Antibody

<400> SEQUENCE: 191
gtgcccgctc agcgcctggg gctcctgctg ctctggttcc caggtgccag gtgtgacatc    60
cagatgaccc agtctccatc ctccctgtct gcatctgtag agacagagt caccatcact   120
tgccgggcaa gtcagggcat tagaaatgat ttaggctggt atcagcagaa accagggaaa   180
gcccctaagc gcctgatcta tgctgcatcc agtttgcaaa gtggggtccc atcaaggttc   240
agcggcagtg gatctgggac agaattcact ctcacaatca gcagcctgca gcctgaagat   300
tttgcaactt attactgtct acagcataat aattacccgt ggacgttcgg ccaagggacc   360
aaggtggaaa tcaaacgaac tgtggctgca ccatctgtct tcatcttccc gccatctgat   420
gagcagttga aatctggaac tg                                            442

<210> SEQ ID NO 192
<211> LENGTH: 107
<212> TYPE: PRT
<213> ORGANISM: Artificial
<220> FEATURE:
<223> OTHER INFORMATION: Antibody

<400> SEQUENCE: 192

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Trp
                85                  90                  95

Thr Phe Gly Gln Gly Thr Lys Val Glu Ile Lys
            100                 105

<210> SEQ ID NO 193
<211> LENGTH: 427
<212> TYPE: DNA
<213> ORGANISM: Artificial
<220> FEATURE:
<223> OTHER INFORMATION: Antibody

<400> SEQUENCE: 193
tggttcttcc ttctgctggt ggcagctccc agatgggtcc tgtcccaggt gcagctgcag    60
gagtcgggcc caggactggt gaagccttca cagaccctgt ccctcacctg cactgtctct   120
ggtggctcca tcagcagtgg tgattactac tggagctgga tccgccagca cccagggaag   180
ggcctggagt ggattgggta catctattac agtgggagca cctactacaa cccgtccctc   240
aagagtcgag ttaccatatc agtagacacg tctaagaacc agttctccct gaagctgagc   300
tctgtgactg ccgcggacac ggccgtgtat ttctgtgcga gagccgatta cgattttgg    360
agtggttatt ttgactactg gggccaggga accctggtca ccgtctcctc agcctccacc   420
aagggcc                                                             427
```

<210> SEQ ID NO 194
<211> LENGTH: 122
<212> TYPE: PRT
<213> ORGANISM: Artificial
<220> FEATURE:
<223> OTHER INFORMATION: Antibody

<400> SEQUENCE: 194

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 195
<211> LENGTH: 518
<212> TYPE: DNA
<213> ORGANISM: Artificial
<220> FEATURE:
<223> OTHER INFORMATION: Antibody

<400> SEQUENCE: 195
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag ctggtatca gcagaaacca     180 gggaaagccc ctaagcgcct gatctatgct gcatccagtt tgcaaagtgg ggtcccatca     240
aggttcagcg gcagtggatc tgggacagaa ttcactctca caatcagcag cctgcagcct     300
gaagattttg caacttatta ctgtctacag cataatactt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgc                             518

<210> SEQ ID NO 196
<211> LENGTH: 107
<212> TYPE: PRT
<213> ORGANISM: Artificial
<220> FEATURE:
<223> OTHER INFORMATION: Antibody

<400> SEQUENCE: 196

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile

```
                35                   40                   45
Tyr Ala Ala Ser Ser Leu Gln Ser Gly Val Pro Ser Arg Phe Ser Gly
            50                   55                   60

Ser Gly Ser Gly Thr Glu Phe Thr Leu Thr Ile Ser Ser Leu Gln Pro
65                   70                   75                   80

Glu Asp Phe Ala Thr Tyr Tyr Cys Leu Gln His Asn Thr Tyr Pro Trp
                85                   90                   95

Thr Phe Gly Gln Gly Thr Lys Val Glu Ile Lys
            100                  105
```

<210> SEQ ID NO 197
<211> LENGTH: 428
<212> TYPE: DNA
<213> ORGANISM: Artificial
<220> FEATURE:
<223> OTHER INFORMATION: Antibody

<400> SEQUENCE: 197

```
tggttcttcc ttctgctggt ggcagctccc agatgggtcc tgtcccaggt gcagctgcag     60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattgggta catctattac agtgggagca cctactacaa cccgtccctc    240
aagagtcgag ttaccatatc agtagacacg tctaagaacc agttctccct gaagctgagc    300
tctgtgactg ccgcggacac ggccgtgtat ttctgtgcga gagccgatta cgattttggg    360
aatggttatt ttgactactg gggccaggga accctggtca ccgtctcctc agcctccacc    420
aagggccc                                                             428
```

<210> SEQ ID NO 198
<211> LENGTH: 122
<212> TYPE: PRT
<213> ORGANISM: Artificial
<220> FEATURE:
<223> OTHER INFORMATION: Antibody

<400> SEQUENCE: 198

```
Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Asn Gly Tyr Phe Asp Tyr Trp
            100                 105                 110

Gly Gln Gly Thr Leu Val Thr Val Ser Ser
        115                 120
```

<210> SEQ ID NO 199
<211> LENGTH: 519
<212> TYPE: DNA
<213> ORGANISM: Artificial
<220> FEATURE:
<223> OTHER INFORMATION: Antibody

<400> SEQUENCE: 199

```
atgagggtcc ccgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag gctggtatca gcagaaacca   180
gggaaagccc ctaagcgcct gatctatgct gcttccagtt tgcaaagtgg ggtcccatca   240
aggttcagcg gcagtggatc tgggacagaa ttcactctca caatcagcag cctgcagcct   300
gaagattttg caacttatta ctgtctacag cataatactt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                          519
```

<210> SEQ ID NO 200
<211> LENGTH: 107
<212> TYPE: PRT
<213> ORGANISM: Artificial
<220> FEATURE:
<223> OTHER INFORMATION: Antibody

<400> SEQUENCE: 200

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Thr Tyr Pro Trp
                85                  90                  95

Thr Phe Gly Gln Gly Thr Lys Val Glu Ile Lys
            100                 105
```

<210> SEQ ID NO 201
<211> LENGTH: 398
<212> TYPE: DNA
<213> ORGANISM: Artificial
<220> FEATURE:
<223> OTHER INFORMATION: Antibody

<400> SEQUENCE: 201

```
ttggtggcag cagctacagg cacccacgcc caggtccagc tggtacagtc tggggctgag    60
gtgaagaagc ctggggcctc agtgaaggtc tcctgcaagg tttccggata cacccctcact  120
gaattatcca tgtactgggt gcgacaggct cctggaaaag gcttgagtg gatgggaggt    180
tttgatcctg aagatggtga aacaatctac gcacagaagt tccagggcag agtcaccatg   240
accgaggaca catctacaga cacagcctac atggagctga gcagcctgag atctgaggac   300
acggccgtgt attactgtgc aactgggtgg aactacgtct ttgactactg gggccaggga   360
accctggtca ccgtctcctc agcctccacc aagggccc                           398
```

-continued

```
<210> SEQ ID NO 202
<211> LENGTH: 117
<212> TYPE: PRT
<213> ORGANISM: Artificial
<220> FEATURE:
<223> OTHER INFORMATION: Antibody

<400> SEQUENCE: 202

Gln Val Gln Leu Val Gln Ser Gly Ala Glu Lys Lys Pro Gly Ala
1               5                   10                  15

Ser Val Lys Val Ser Cys Lys Val Ser Gly Tyr Thr Leu Thr Glu Leu
            20                  25                  30

Ser Met Tyr Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Gly Trp Asn Tyr Val Phe Asp Tyr Trp Gly Gln Gly Thr Leu
            100                 105                 110

Val Thr Val Ser Ser
        115

<210> SEQ ID NO 203
<211> LENGTH: 388
<212> TYPE: DNA
<213> ORGANISM: Artificial
<220> FEATURE:
<223> OTHER INFORMATION: Antibody

<400> SEQUENCE: 203
ggatccagtg gggatattgt gatgactcag tctccactct ccctgcccgt cacccctgga    60
gagccggcct ccatctcctg caggtccagt cagagcctcc tgcatagtaa tggatacaac   120
tatttggatt ggtacctgca gaagccaggg cagtctccac agctcctgat ctatttggat   180
tctcatcggg cctccggggt ccctgacagg ttcagtggca gtggatcagg cacagatttt   240
acactgaaaa tcagcagagt ggaggctgag gatgttgggg tttattactg catgcaagct   300
ctacaaactc cgctcacttt cggcggaggg accaaggtgg agatcaaacg aactgtggct   360
gcaccatctg tcttcatctt cccgccat                                      388

<210> SEQ ID NO 204
<211> LENGTH: 112
<212> TYPE: PRT
<213> ORGANISM: Artificial
<220> FEATURE:
<223> OTHER INFORMATION: Antibody

<400> SEQUENCE: 204

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Asp Ser His Arg Ala Ser Gly Val Pro
    50                  55                  60
```

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Lys
            100                 105                 110

<210> SEQ ID NO 205
<211> LENGTH: 446
<212> TYPE: DNA
<213> ORGANISM: Artificial
<220> FEATURE:
<223> OTHER INFORMATION: Antibody

<400> SEQUENCE: 205
tggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tgattactac tggagctgga tccgccagca cccagggaag     180
ggcctggagt ggattgggta catctattac agtgggagca cctactacaa cccgtccctc     240
aagagtcgag ttaccatatc agtagacacg tctaagaacc agttctccct gaagctgagc     300
tctgtgactg ccgcggacac ggccgtgtat ttctgtgcga gagccgatta cgattttggg     360
agtggttatt ttgactactg gggccaggga accctggtca ccgtctcctc agcctccacc     420
aagggcccat cgagtcttcc ccctgg                                          446

<210> SEQ ID NO 206
<211> LENGTH: 122
<212> TYPE: PRT
<213> ORGANISM: Artificial
<220> FEATURE:
<223> OTHER INFORMATION: Antibody

<400> SEQUENCE: 206

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
                20                  25                  30

Asp Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
        50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 207
<211> LENGTH: 519
<212> TYPE: DNA
<213> ORGANISM: Artificial
<220> FEATURE:
<223> OTHER INFORMATION: Antibody

<400> SEQUENCE: 207

```
atgagggtcc cgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaagtca gggcattaga aatgatttag gctggtatca gcagaaacca   180
gggaaagccc ctaagcgcct gatctatgct gcatccagtt tgcaaagtgg ggtcccatca   240
aggttcagcg gcagtggatc tgggacaaaa ttcactctca ctatcagcag cctgcagcct   300
gaagattttg caacttatta ctgtctacag cataatactt acccgtggac gttcggccaa   360
gggaccaagg tggaaatcag acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgcc                         519
```

<210> SEQ ID NO 208
<211> LENGTH: 107
<212> TYPE: PRT
<213> ORGANISM: Artificial
<220> FEATURE:
<223> OTHER INFORMATION: Antibody

<400> SEQUENCE: 208

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Arg Asn Asp
            20                  25                  30
Leu Gly Trp Tyr Gln Gln Lys Pro Gly Lys Ala Pro Lys Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Lys Phe Thr Leu Thr Ile Ser Ser Leu Gln Pro
65                  70                  75                  80
Glu Asp Phe Ala Thr Tyr Tyr Cys Leu Gln His Asn Thr Tyr Pro Trp
                85                  90                  95
Thr Phe Gly Gln Gly Thr Lys Val Glu Ile Arg
            100                 105

<210> SEQ ID NO 209
<211> LENGTH: 564
<212> TYPE: DNA
<213> ORGANISM: Artificial
<220> FEATURE:
<223> OTHER INFORMATION: Antibody

<400> SEQUENCE: 209

```
accatgaaac atctgtggtt cttcctcctg ctggtggcag ctcccagatg ggtcctgtcc    60
caggtgcagc tgcaggagtc gggcccagga ctggtgaagc cttcacagac cctgtccctc   120
acctgcactg tctctggtgg ctccatcagc agtggtgatt actactggag ctggatccgc   180
cagcacccag ggaagggcct ggagtggatt gggtacatct attacagtgg gagcacctac   240
tacaacccgt ccctcaagag tcgagttacc atatcagtag acacgtctaa gaaccagttc   300
tccctgaagc tgagctctgt gactgccgcg gacacggccg tgtattactg tgcgagagcg   360
gattacgatt tttggagtgg ttattttgac tactggggcc agggaatcct ggtcaccgtc   420
tcctcagcct ccaccaaggg cccatcggtc ttccccctgg cacctcctc caagaacacc    480
tctgggggca cagcggccct gggctgcctg gtcaaggact acttccccga accggtgacg   540
gtgtcctgga actcaggcgc cctg                                         564
```

<210> SEQ ID NO 210
<211> LENGTH: 122
<212> TYPE: PRT
<213> ORGANISM: Artificial
<220> FEATURE:
<223> OTHER INFORMATION: Antibody

<400> SEQUENCE: 210

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Ile Leu Val Thr Val Ser Ser
        115                 120

<210> SEQ ID NO 211
<211> LENGTH: 519
<212> TYPE: DNA
<213> ORGANISM: Artificial
<220> FEATURE:
<223> OTHER INFORMATION: Antibody

<400> SEQUENCE: 211
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga aatgatttag ctggtatca gcagaaacca     180 gggaaagccc ctaagcgcct gatctatgct gcatccagtt tgcaaagtgg ggtcccatca     240
aggttcagcg gcagtggatc tgggacagaa ttcactctca caatcagcag cctgcagcct     300
gaagattttg caacttatta ctgtctacag cataatagtt acccgtggac gttcggccaa     360
gggaccaagg tggaaatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtggaaggtg gataacgcc                            519

<210> SEQ ID NO 212
<211> LENGTH: 107
<212> TYPE: PRT
<213> ORGANISM: Artificial
<220> FEATURE:
<223> OTHER INFORMATION: Antibody

<400> SEQUENCE: 212

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile

```
                35                  40                  45
Tyr Ala Ala Ser Ser Leu Gln Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
            100                 105

<210> SEQ ID NO 213
<211> LENGTH: 432
<212> TYPE: DNA
<213> ORGANISM: Artificial
<220> FEATURE:
<223> OTHER INFORMATION: Antibody

<400> SEQUENCE: 213
tggttcttcc ttctgctggt ggcagctccc agatgggtcc tgtcccaggt gcagctgcag     60
gagtcgggcc caggactggt gaagccttca cagaccctgt ccctcacctg cactgtctct    120
ggtggctcca tcagcagtgg tgattactac tggagctgga tccgccagca cccagggaag    180
ggcctggagt ggattggata catctattac agtgggagca cctactacaa ttcgtccctc    240
aagagtcgag ttaccatatc agtagacacg tctaagaacc agttctccct gaagctgagc    300
tctgtgactg ccgcggacac ggccgtgtat tactgtgcga gcggattac cgattttttgg    360
```

```
<220> FEATURE:
<223> OTHER INFORMATION: Antibody

<400> SEQUENCE: 215
ggtgccaggt gtgacatcca gatgacccag tctccatcct ccctgtctgc atctgtagga      60
gacagagtca ccatcacttg ccgggcaagt cagggcatta gaaatgattt aggctggtat     120
cagcagaaac ctgggaaagc ccctaagcgc ctgatctatg ctgcatccag tttgcaaagt     180
ggggtcccat caaggttcag cggcagtgga tctgggacag aattcactct cacaatcagc     240
agcctgcagc ctgaagattt tgcaacttat tactgtctac agcacaatag ttacccgtgg     300
acgttcggcc aagggaccaa ggtggaaatc aaacgaactg tggctgcacc atctgtcttc     360
atcttcccgc ca                                                         372

<210> SEQ ID NO 216
<211> LENGTH: 107
<212> TYPE: PRT
<213> ORGANISM: Artificial
<220> FEATURE:
<223> OTHER INFORMATION: Antibody

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Trp
                85                  90                  95

Thr Phe Gly Gln Gly Thr Lys Val Glu Ile Lys
            100                 105

<210> SEQ ID NO 217
<211> LENGTH: 548
<212> TYPE: DNA
<213> ORGANISM: Artificial
<220> FEATURE:
<223> OTHER INFORMATION: Antibody

<400> SEQUENCE: 217
aggttcttcc ttctgctggt ggcagctccc agatgggtcc tgtcccaggt gcagctgcag      60
gagtcgggcc caggactggt gaagccttca cagaccctgt ccctcacctg cactgtctct     120
ggtggctcca tcagcagtgg tgattactac tggagctgga tccgccagca cccagggaag     180
ggcctggagt ggattggata catctattac agtgggagca cctactacaa cccgtccctc     240
aagagtcgag ttaccatatc agtagacacg tctaagaacc agttctccct gaagctgagc     300
tctgtgactg ccgcggacac ggccgtgtat tactgtgcga gagccgatta cgattttggg     360
agtggttatt ttgactactg gggccaggga accctggtca ccgtctcctc agcctccacc     420
aagggcccat cggtcttccc cctggcaccc tcctccaaga gcacctctgg gggcacagcg     480
gccctgggct gcctggtcaa ggactacttc cccgaaccgg tgacggtgtc gtggaactca     540
ggcgccct                                                             548
```

<210> SEQ ID NO 218
<211> LENGTH: 122
<212> TYPE: PRT
<213> ORGANISM: Artificial
<220> FEATURE:
<223> OTHER INFORMATION: Antibody

<400> SEQUENCE: 218

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Asp Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
        115                 120

<210> SEQ ID NO 219
<211> LENGTH: 517
<212> TYPE: DNA
<213> ORGANISM: Artificial
<220> FEATURE:
<223> OTHER INFORMATION: Antibody

<400> SEQUENCE: 219
atgagggtcc ccgctcagct cctggggctc ctgctgctct ggttcccagg tgccaggtgt     60
gacatccaga tgacccagtc tccatcctcc ctgtctgcat ctgtaggaga cagagtcacc    120
atcacttgcc gggcaagtca gggcattaga aatgatttag ctggtatca gcagaaacca    180 gggaaagccc ctaagcgcct gatctatgct gcatccagtt tgcaaagtgg ggtcccatca    240
aggttcagcg gcagtggatc tgggacagaa ttcactctca caatcagcag cctgcagcct    300
gaagattttg caacttatta ctgtctacag cataatagtt acccgtggac gttcggccaa    360
gggaccaagg tggaaatcaa acgaactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacg                             517

<210> SEQ ID NO 220
<211> LENGTH: 107
<212> TYPE: PRT
<213> ORGANISM: Artificial
<220> FEATURE:
<223> OTHER INFORMATION: Antibody

<400> SEQUENCE: 220

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

```
Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
                100                 105
```

<210> SEQ ID NO 221
<211> LENGTH: 446
<212> TYPE: DNA
<213> ORGANISM: Artificial
<220> FEATURE:
<223> OTHER INFORMATION: Antibody

<400> SEQUENCE: 221

```
ctgtggttct tccttctgct ggtggcagct cccagatggg tcctgtccca ggtgcagctg    60
caggagtcgg gcccaggact ggtgaagcct tcacagaccc tgtccctcac ctgcactgtc   120
tctggtggct ccatcagcag tggtgattac tactggagct ggatccgcca gcacccaggg   180
aagggcctgg agtggattgg gtacatctat acagtgggag ccacctacta caacccgtcc   240
ctcaagagtc gagttaccat gtcagtagac acgtctaaga accagttctc cctgaagctg   300
agctctgtga ctgccgcgga cacggccgtg tattactgtg cgagagccga ttacgatttt   360
tggagtggtc actttgactg ctggggccag ggaaccctgg tcaccgtctc ctcagcttcc   420
accaagggcc catccgtctt ccccc                                         446
```

<210> SEQ ID NO 222
<211> LENGTH: 122
<212> TYPE: PRT
<213> ORGANISM: Artificial
<220> FEATURE:
<223> OTHER INFORMATION: Antibody

<400> SEQUENCE: 222

```
Gln Val Gln Leu Gln Glu Ser Gly Pro Gly Leu Val Lys Pro Ser Gln
 1               5                  10                  15

Thr Leu Ser Leu Thr Cys Thr Val Ser Gly Gly Ser Ile Ser Ser Gly
                 20                  25                  30

Asp Tyr Tyr Trp Ser Trp Ile Arg Gln His Pro Gly Lys Gly Leu Glu
             35                  40                  45

Trp Ile Gly Tyr Ile Tyr Tyr Ser Gly Ser Thr Tyr Tyr Asn Pro Ser
 50                  55                  60

Leu Lys Ser Arg Val Thr Met Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Ala Asp Tyr Asp Phe Trp Ser Gly His Phe Asp Cys Trp
                100                 105                 110

Gly Gln Gly Thr Leu Val Thr Val Ser Ser
            115                 120
```

<210> SEQ ID NO 223
<211> LENGTH: 419
<212> TYPE: DNA

<213> ORGANISM: Artificial
<220> FEATURE:
<223> OTHER INFORMATION: Antibody

<400> SEQUENCE: 223

```
atgagggtcc ccgctcagct cctggggctc ctgctgctct ggttcccagg tgccaggtgt      60
gacatccaga tgacccagtc tccatcctcc ctgtctgcat ctgtaggaga cagagtcacc     120
atcacttgcc gggcaagtca gggcattaga gatgatttag ctggtatca gcagaaacca      180
gggaaagccc ctaagcgcct gatctatgct gaatccagtt tgcaaagtgg ggtcccatca     240
aggttcagcg gcagtggatc tgggacagaa ttcactctca caatcagcag cctgcagcct     300
gaagattttg caacttatta ctgtctacag catcatagtt acccgtggac gttcggccaa     360
gggaccaagg tggaaatcaa acgaactgtg gctgcaccat ctgtcttcat cttcccgcc      419
```

<210> SEQ ID NO 224
<211> LENGTH: 107
<212> TYPE: PRT
<213> ORGANISM: Artificial
<220> FEATURE:
<223> OTHER INFORMATION: Antibody

<400> SEQUENCE: 224

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asp Asp
            20                  25                  30

Leu Gly Trp Tyr Gln Gln Lys Pro Gly Lys Ala Pro Lys Arg Leu Ile
        35                  40                  45

Tyr Ala Glu Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His His Ser Tyr Pro Trp
                85                  90                  95

Thr Phe Gly Gln Gly Thr Lys Val Glu Ile Lys
            100                 105
```

<210> SEQ ID NO 225
<211> LENGTH: 504
<212> TYPE: DNA
<213> ORGANISM: Artificial
<220> FEATURE:
<223> OTHER INFORMATION: Antibody

<400> SEQUENCE: 225

```
tggctgagct gggttttcct cgttgctctt ttaagaggtg tccagtgtca ggtgcagctg      60
gtggagtctg ggggaggcgt ggtccagcct ggagggtccc tgagactctc ctgtgcagcg     120
tctggattca ccttcaatag ctatgacatg cactgggtcc gccaggctcc aggcaagggg     180
ctggagtggg tggcagttat atggtatgat ggaagtaata atactatgc agactccgtg      240
aagggccgat tcaccatctc tagagacaat tccaagaaca cgctgtatct gcaaatgaac     300
agcctgagag ccgaggacac ggctgtgtat tactgtgcga gaccgcttg tgtactaat       360
ggtgtatgct atgaagacta cggtatggac gtctggggcc aagggaccac ggtcaccgtc     420
tcctcagctt ccaccaaggg cccatccgtc ttccccctgg cgccctgctc caggagcacc     480
tccgagagca cagccgccct gggc                                            504
```

<210> SEQ ID NO 226
<211> LENGTH: 126
<212> TYPE: PRT
<213> ORGANISM: Artificial
<220> FEATURE:
<223> OTHER INFORMATION: Antibody

<400> SEQUENCE: 226

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Asn Ser Tyr
            20                  25                  30

Asp Met His Trp Val Arg Gln Ala Pro Gly Lys Gly Leu Glu Trp Val
        35                  40                  45

Ala Val Ile Trp Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Leu Cys Thr Asn Gly Val Cys Tyr Glu Asp Tyr Gly
            100                 105                 110

Met Asp Val Trp Gly Gln Gly Thr Thr Val Thr Val Ser Ser
        115                 120                 125

<210> SEQ ID NO 227
<211> LENGTH: 504
<212> TYPE: DNA
<213> ORGANISM: Artificial
<220> FEATURE:
<223> OTHER INFORMATION: Antibody

<400> SEQUENCE: 227
atgagggtcc ctgctcagct cctggggctc ctgctgctct ggctctcagg tgccagatgt      60
gacatccaga tgacccagtc tccatcctcc ctgtctgcat ctgtaggaga cagagtcacc     120
atcacttgcc aggcgagtca ggacattagc aactatttaa attggtatca gcagaaacca     180
gggaaagccc ctaaggtcct gatctacgat gcatccaatt tggaaacagg ggtcccatca     240
aggttcagtg gaagtggatc tgggacagat tttactttca ccatcagcag cctgcagcct     300
gaagatgttg caacatatta ctgtcaacac tatgatactc tcccgctcac tttcggcgga     360
gggaccaagg tggagatcaa acgaactgtg gctgcaccat ctgtcttcat cttcccgcca     420
tctgatgagc agttgaaatc tggaactgcc tctgttgtgt gcctgctgaa taacttctat     480
cccagagagg ccaaagtaca gtgg                                            504

<210> SEQ ID NO 228
<211> LENGTH: 107
<212> TYPE: PRT
<213> ORGANISM: Artificial
<220> FEATURE:
<223> OTHER INFORMATION: Antibody

<400> SEQUENCE: 228

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Val Leu Ile

```
                35                  40                  45
Tyr Asp Ala Ser Asn Leu Glu Thr Gly Val Pro Ser Arg Phe Ser Gly
     50                  55                  60

Ser Gly Ser Gly Thr Asp Phe Thr Phe Thr Ile Ser Ser Leu Gln Pro
 65                  70                  75                  80

Glu Asp Val Ala Thr Tyr Tyr Cys Gln His Tyr Asp Thr Leu Pro Leu
                 85                  90                  95

Thr Phe Gly Gly Gly Thr Lys Val Glu Ile Lys
            100                 105

<210> SEQ ID NO 229
<211> LENGTH: 472
<212> TYPE: DNA
<213> ORGANISM: Artificial
<220> FEATURE:
<223> OTHER INFORMATION: Antibody

<400> SEQUENCE: 229
ggactgtgca agaacatgaa acacctgtgg ttcttcctcc tgctggtggc agctcccaga      60
tgggtcctgt cccaggtgca gctgcaggag tcgggcccag gactggtgaa gccttttacag    120 accctgtccc tcacctgcac tgtctctggt ggctccatca gcagtggtga ttactactgg    180
agctggatcc gccagcaccc agggaagggc ctggagtgga ttgggtacat ctattacagt    240
gggaccacct actacaaccc gtccctcaag agtcgagtta ccatatcagt agacacgtct    300
aagaaccagt tcgccctgaa gctgaactct gtgactgccg cggacacggc cgtgtattac    360
tgtgcgagag ccgattacga tttttggagt ggttatttg actactgggg ccagggaacc    420
ctggtcaccg tctcctcagc ttccaccaag ggcccatccg tcttccccct gg            472

<210> SEQ ID NO 230
<211> LENGTH: 122
<212> TYPE: PRT
<213> ORGANISM: Artificial
<220> FEATURE:
<223> OTHER INFORMATION: Antibody

<400> SEQUENCE: 230

Gln Val Gln Leu Gln Glu Ser Gly Pro Gly Leu Val Lys Pro Leu Gln
  1               5                  10                  15

Thr Leu Ser Leu Thr Cys Thr Val Ser Gly Gly Ser Ile Ser Ser Gly
                 20                  25                  30

Asp Tyr Tyr Trp Ser Trp Ile Arg Gln His Pro Gly Lys Gly Leu Glu
             35                  40                  45

Trp Ile Gly Tyr Ile Tyr Tyr Ser Gly Thr Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ala Leu Lys Leu Asn Ser Val Thr Ala Ala Asp Thr Ala Val Tyr Tyr
                 85                  90                  95

Cys Ala Arg Ala Asp Tyr Asp Phe Trp Ser Gly Tyr Phe Asp Tyr Trp
            100                 105                 110

Gly Gln Gly Thr Leu Val Thr Val Ser Ser
            115                 120

<210> SEQ ID NO 231
<211> LENGTH: 531
<212> TYPE: DNA
<213> ORGANISM: Artificial
```

<220> FEATURE:
<223> OTHER INFORMATION: Antibody

<400> SEQUENCE: 231

```
atgagggtcc ctgctcagct cctggggctc ctgctgctct ggttcccagg tgccaggtgt    60
gacatccaga tgacccagtc tccatcctcc ctgtctgcat ctgtaggaga cagagtcacc   120
atcacttgcc gggcaggtca gggcattaga aatgatttag ctggtatca gcagaaacca    180
gggaaagccc ctcagcgcct gatctatgct gcatccagtt tgcaaagtgg ggtcccatca   240
aggttcagcg gcagtggatc tgggacagaa ttctctctca caatctccag cctgcagcct   300
gaagattttg caacttatta ctgtctacag cataatagtt acccgtggac gttcggccaa   360
gggaccaagg tggaaatcaa acgaactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc ttccaatcgg g            531
```

<210> SEQ ID NO 232
<211> LENGTH: 107
<212> TYPE: PRT
<213> ORGANISM: Artificial
<220> FEATURE:
<223> OTHER INFORMATION: Antibody

<400> SEQUENCE: 232

Asp Ile Gln Met Thr Gln Ser Pro Ser Ser Leu Ser Ala Ser Val Gly
1               5                   10                  15
Asp Arg Val Thr Ile Thr Cys Arg Ala Gly Gln Gly Ile Arg Asn Asp
            20                  25                  30
Leu Gly Trp Tyr Gln Gln Lys Pro Gly Lys Ala Pro Gln Arg Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Glu Phe Ser Leu Thr Ile Ser Ser Leu Gln Pro
65                  70                  75                  80
Glu Asp Phe Ala Thr Tyr Tyr Cys Leu Gln His Asn Ser Tyr Pro Trp
                85                  90                  95
Thr Phe Gly Gln Gly Thr Lys Val Glu Ile Lys
            100                 105

<210> SEQ ID NO 233
<211> LENGTH: 26
<212> TYPE: DNA
<213> ORGANISM: Artificial
<220> FEATURE:
<223> OTHER INFORMATION: Primer
<220> FEATURE:
<221> NAME/KEY: prim_transcript
<222> LOCATION: (1)..(26)

<400> SEQUENCE: 233

```
cgggatccat gtcctagcct agggc                                          26
```

<210> SEQ ID NO 234
<211> LENGTH: 39
<212> TYPE: DNA
<213> ORGANISM: Artificial
<220> FEATURE:
<223> OTHER INFORMATION: Primer
<220> FEATURE:
<221> NAME/KEY: prim_transcript
<222> LOCATION: (1)..(39)

<400> SEQUENCE: 234
gctctagatt aatgatgatg atgatgatgt tgtcctaaa                39

<210> SEQ ID NO 235
<211> LENGTH: 12
<212> TYPE: PRT
<213> ORGANISM: Artificial
<220> FEATURE:
<223> OTHER INFORMATION: U1-1 CDR-1-h

<400> SEQUENCE: 235

Gly Gly Ser Ile Asn Ser Gly Asp Tyr Tyr Trp Ser
1               5                   10

<210> SEQ ID NO 236
<211> LENGTH: 16
<212> TYPE: PRT
<213> ORGANISM: Artificial
<220> FEATURE:
<223> OTHER INFORMATION: U1-1 CDR-2-h

<400> SEQUENCE: 236

Tyr Ile Tyr Tyr Ser Gly Ser Thr Tyr Tyr Asn Pro Ser Leu Lys Ser
1               5                   10                  15

<210> SEQ ID NO 237
<211> LENGTH: 12
<212> TYPE: PRT
<213> ORGANISM: Artificial
<220> FEATURE:
<223> OTHER INFORMATION: U1-1 CDR-3-h

<400> SEQUENCE: 237

Ala Asp Tyr Asp Phe Trp Ser Gly Tyr Phe Asp Tyr
1               5                   10

<210> SEQ ID NO 238
<211> LENGTH: 11
<212> TYPE: PRT
<213> ORGANISM: Artificial
<220> FEATURE:
<223> OTHER INFORMATION: U1-1 CDR-1-l

<400> SEQUENCE: 238

Arg Ala Ser Gln Gly Ile Arg Asn Asp Leu Gly
1               5                   10

<210> SEQ ID NO 239
<211> LENGTH: 7
<212> TYPE: PRT
<213> ORGANISM: Artificial
<220> FEATURE:
<223> OTHER INFORMATION: U1-1 CDR-2-l

<400> SEQUENCE: 239

Ala Ala Ser Ser Leu Gln Ser
1               5

<210> SEQ ID NO 240
<211> LENGTH: 9
<212> TYPE: PRT
<213> ORGANISM: Artificial
<220> FEATURE:
<223> OTHER INFORMATION: U1-1 CDR-3-l

<400> SEQUENCE: 240

Leu Gln His Asn Ser Tyr Pro Trp Thr
1               5

<210> SEQ ID NO 241
<211> LENGTH: 12
<212> TYPE: PRT
<213> ORGANISM: Artificial
<220> FEATURE:
<223> OTHER INFORMATION: U 1 - 2-CDR-1h

<400> SEQUENCE: 241

Gly Gly Ser Ile Ser Ser Gly Asp Tyr Tyr Trp Ser
1               5                   10

<210> SEQ ID NO 242
<211> LENGTH: 16
<212> TYPE: PRT
<213> ORGANISM: Artificial
<220> FEATURE:
<223> OTHER INFORMATION: U 1 - 2-CDR-2h

<400> SEQUENCE: 242

Tyr Ile Tyr Tyr Ser Gly Ser Thr Tyr Tyr Asn Pro Ser Leu Arg Ser
1               5                   10                  15

<210> SEQ ID NO 243
<211> LENGTH: 12
<212> TYPE: PRT
<213> ORGANISM: Artificial
<220> FEATURE:
<223> OTHER INFORMATION: U 1 - 2-CDR-3h

<400> SEQUENCE: 243

Ala Asp Tyr Asp Phe Trp Ser Gly Tyr Phe Asp Tyr
1               5                   10

<210> SEQ ID NO 244
<211> LENGTH: 11
<212> TYPE: PRT
<213> ORGANISM: Artificial
<220> FEATURE:
<223> OTHER INFORMATION: U 1 - 2-CDR-1l

<400> SEQUENCE: 244

Arg Ala Ser Gln Gly Ile Arg Asn Asp Leu Gly
1               5                   10

<210> SEQ ID NO 245
<211> LENGTH: 7
<212> TYPE: PRT
<213> ORGANISM: Artificial
<220> FEATURE:
<223> OTHER INFORMATION: U 1 - 2-CDR-2l

<400> SEQUENCE: 245

Ala Ala Ser Ser Leu Gln Ser
1               5

<210> SEQ ID NO 246
<211> LENGTH: 9
<212> TYPE: PRT
<213> ORGANISM: Artificial
<220> FEATURE:
<223> OTHER INFORMATION: U 1 - 2-CDR-3l

<400> SEQUENCE: 246

Leu Gln His Asn Gly Tyr Pro Trp Thr
1               5

<210> SEQ ID NO 247
<211> LENGTH: 12
<212> TYPE: PRT
<213> ORGANISM: Artificial
<220> FEATURE:
<223> OTHER INFORMATION: U 1 - 3-CDR-1-h

<400> SEQUENCE: 247

Gly Gly Ser Ile Ser Ser Gly Gly Tyr Tyr Trp Ser
1               5                   10

<210> SEQ ID NO 248
<211> LENGTH: 16
<212> TYPE: PRT
<213> ORGANISM: Artificial
<220> FEATURE:
<223> OTHER INFORMATION: U 1 - 3-CDR-2h

<400> SEQUENCE: 248

Tyr Ile Tyr Tyr Ser Gly Ser Thr Tyr Tyr Asn Pro Ser Leu Lys Ser
1               5                   10                  15

<210> SEQ ID NO 249
<211> LENGTH: 15
<212> TYPE: PRT
<213> ORGANISM: Artificial
<220> FEATURE:
<223> OTHER INFORMATION: U 1 - 3-CDR-3h

<400> SEQUENCE: 249

Asp Gly Tyr Asp Ser Ser Gly Tyr Tyr His Gly Tyr Phe Asp Tyr
1               5                   10                  15

<210> SEQ ID NO 250
<211> LENGTH: 17
<212> TYPE: PRT
<213> ORGANISM: Artificial
<220> FEATURE:
<223> OTHER INFORMATION: U 1 - 3-CDR-1l

<400> SEQUENCE: 250

Lys Ser Ser Gln Ser Val Leu Tyr Ser Ser Asn Asn Lys Asn Tyr Leu
1               5                   10                  15

Ala

<210> SEQ ID NO 251
<211> LENGTH: 7
<212> TYPE: PRT
<213> ORGANISM: Artificial
<220> FEATURE:
<223> OTHER INFORMATION: U 1 - 3-CDR-2l

<400> SEQUENCE: 251

Trp Ala Ser Thr Arg Glu Ser
1               5

<210> SEQ ID NO 252
<211> LENGTH: 9
<212> TYPE: PRT
<213> ORGANISM: Artificial
<220> FEATURE:
<223> OTHER INFORMATION: U 1 - 3-CDR-3l

<400> SEQUENCE: 252

```
Gln Gln Tyr Tyr Ser Thr Pro Leu Thr
1               5

<210> SEQ ID NO 253
<211> LENGTH: 12
<212> TYPE: PRT
<213> ORGANISM: Artificial
<220> FEATURE:
<223> OTHER INFORMATION: U 1 - 4-CDR-1h

<400> SEQUENCE: 253

Gly Gly Ser Ile Ser Ser Gly Asp Tyr Tyr Trp Ser
1               5                   10

<210> SEQ ID NO 254
<211> LENGTH: 16
<212> TYPE: PRT
<213> ORGANISM: Artificial
<220> FEATURE:
<223> OTHER INFORMATION: U 1 - 4-CDR-2h

<400> SEQUENCE: 254

Tyr Ile Tyr Tyr Ser Gly Ser Thr Tyr Tyr Asn Pro Ser Leu Lys Ser
1               5                   10                  15

<210> SEQ ID NO 255
<211> LENGTH: 12
<212> TYPE: PRT
<213> ORGANISM: Artificial
<220> FEATURE:
<223> OTHER INFORMATION: U 1 - 4-CDR-3h

<400> SEQUENCE: 255

Ala Asp Tyr Asp Phe Trp Ser Gly Tyr Phe Asp Tyr
1               5                   10

<210> SEQ ID NO 256
<211> LENGTH: 11
<212> TYPE: PRT
<213> ORGANISM: Artificial
<220> FEATURE:
<223> OTHER INFORMATION: U 1 - 4-CDR-1l

<400> SEQUENCE: 256

Arg Ala Ser Gln Gly Ile Arg Asn Asp Leu Gly
1               5                   10

<210> SEQ ID NO 257
<211> LENGTH: 7
<212> TYPE: PRT
<213> ORGANISM: Artificial
<220> FEATURE:
<223> OTHER INFORMATION: U 1 - 4-CDR-2l

<400> SEQUENCE: 257

Ala Ala Ser Ser Leu Gln Ser
1               5

<210> SEQ ID NO 258
<211> LENGTH: 9
<212> TYPE: PRT
<213> ORGANISM: Artificial
<220> FEATURE:
<223> OTHER INFORMATION: U 1 - 4-CDR-3l

<400> SEQUENCE: 258
```

```
Leu Gln His Asn Asn Tyr Pro Trp Thr
1               5

<210> SEQ ID NO 259
<211> LENGTH: 12
<212> TYPE: PRT
<213> ORGANISM: Artificial
<220> FEATURE:
<223> OTHER INFORMATION: U 1 - 5-CDR-1h

<400> SEQUENCE: 259

Gly Gly Ser Ile Ser Ser Gly Asp Tyr Tyr Trp Ser
1               5                   10

<210> SEQ ID NO 260
<211> LENGTH: 16
<212> TYPE: PRT
<213> ORGANISM: Artificial
<220> FEATURE:
<223> OTHER INFORMATION: U 1 - 5-CDR-2h

<400> SEQUENCE: 260

Tyr Ile Tyr Tyr Ser Gly Ser Thr Tyr Tyr Asn Pro Ser Leu Lys Ser
1               5                   10                  15

<210> SEQ ID NO 261
<211> LENGTH: 12
<212> TYPE: PRT
<213> ORGANISM: Artificial
<220> FEATURE:
<223> OTHER INFORMATION: U 1 - 5-CDR-3h

<400> SEQUENCE: 261

Ala Asp Tyr Asp Phe Trp Ser Gly Tyr Phe Asp Tyr
1               5                   10

<210> SEQ ID NO 262
<211> LENGTH: 11
<212> TYPE: PRT
<213> ORGANISM: Artificial
<220> FEATURE:
<223> OTHER INFORMATION: U 1 - 5-CDR-1l

<400> SEQUENCE: 262

Arg Ala Ser Gln Gly Ile Arg Asn Asp Leu Gly
1               5                   10

<210> SEQ ID NO 263
<211> LENGTH: 7
<212> TYPE: PRT
<213> ORGANISM: Artificial
<220> FEATURE:
<223> OTHER INFORMATION: U 1 - 5-CDR-2l

<400> SEQUENCE: 263

Ala Ala Ser Ser Leu Gln Ser
1               5

<210> SEQ ID NO 264
<211> LENGTH: 9
<212> TYPE: PRT
<213> ORGANISM: Artificial
<220> FEATURE:
<223> OTHER INFORMATION: U 1 - 5-CDR-3l

<400> SEQUENCE: 264

Leu Gln His Asn Thr Tyr Pro Trp Thr
```

```
<210> SEQ ID NO 265
<211> LENGTH: 12
<212> TYPE: PRT
<213> ORGANISM: Artificial
<220> FEATURE:
<223> OTHER INFORMATION: U1-6-CDR-1h

<400> SEQUENCE: 265

Gly Gly Ser Ile Ser Ser Gly Asp Tyr Tyr Trp Ser
1               5                   10

<210> SEQ ID NO 266
<211> LENGTH: 16
<212> TYPE: PRT
<213> ORGANISM: Artificial
<220> FEATURE:
<223> OTHER INFORMATION: U1-6-CDR-2h

<400> SEQUENCE: 266

Tyr Ile Tyr Tyr Ser Gly Ser Thr Tyr Tyr Asn Pro Ser Leu Lys Ser
1               5                   10                  15

<210> SEQ ID NO 267
<211> LENGTH: 12
<212> TYPE: PRT
<213> ORGANISM: Artificial
<220> FEATURE:
<223> OTHER INFORMATION: U1-6-CDR-3h

<400> SEQUENCE: 267

Ala Asp Tyr Asp Phe Trp Asn Gly Tyr Phe Asp Tyr
1               5                   10

<210> SEQ ID NO 268
<211> LENGTH: 11
<212> TYPE: PRT
<213> ORGANISM: Artificial
<220> FEATURE:
<223> OTHER INFORMATION: U1-6-CDR-1l

<400> SEQUENCE: 268

Arg Ala Ser Gln Gly Ile Arg Asn Asp Leu Gly
1               5                   10

<210> SEQ ID NO 269
<211> LENGTH: 7
<212> TYPE: PRT
<213> ORGANISM: Artificial
<220> FEATURE:
<223> OTHER INFORMATION: U1-6-CDR-2l

<400> SEQUENCE: 269

Ala Ala Ser Ser Leu Gln Ser
1               5

<210> SEQ ID NO 270
<211> LENGTH: 9
<212> TYPE: PRT
<213> ORGANISM: Artificial
<220> FEATURE:
<223> OTHER INFORMATION: U1-6-CDR-3l

<400> SEQUENCE: 270

Leu Gln His Asn Thr Tyr Pro Trp Thr
1               5
```

```
<210> SEQ ID NO 271
<211> LENGTH: 12
<212> TYPE: PRT
<213> ORGANISM: Artificial
<220> FEATURE:
<223> OTHER INFORMATION: U 1 - 7-CDR-1h

<400> SEQUENCE: 271

Gly Gly Ser Ile Ser Ser Gly Asp Tyr Tyr Trp Ser
1               5                   10

<210> SEQ ID NO 272
<211> LENGTH: 16
<212> TYPE: PRT
<213> ORGANISM: Artificial
<220> FEATURE:
<223> OTHER INFORMATION: U 1 - 7-CDR-2h

<400> SEQUENCE: 272

Tyr Ile Tyr Tyr Ser Gly Ser Thr Tyr Tyr Asn Pro Ser Leu Lys Ser
1               5                   10                  15

<210> SEQ ID NO 273
<211> LENGTH: 12
<212> TYPE: PRT
<213> ORGANISM: Artificial
<220> FEATURE:
<223> OTHER INFORMATION: U 1 - 7-CDR-3h

<400> SEQUENCE: 273

Ala Asp Tyr Asp Phe Trp Ser Gly Tyr Phe Asp Tyr
1               5                   10

<210> SEQ ID NO 274
<211> LENGTH: 11
<212> TYPE: PRT
<213> ORGANISM: Artificial
<220> FEATURE:
<223> OTHER INFORMATION: U 1 - 7-CDR-1l

<400> SEQUENCE: 274

Arg Ala Ser Gln Asp Ile Arg Asn Asp Leu Gly
1               5                   10

<210> SEQ ID NO 275
<211> LENGTH: 7
<212> TYPE: PRT
<213> ORGANISM: Artificial
<220> FEATURE:
<223> OTHER INFORMATION: U 1 - 7-CDR-2l

<400> SEQUENCE: 275

Ala Ala Ser Ser Leu Gln Ser
1               5

<210> SEQ ID NO 276
<211> LENGTH: 9
<212> TYPE: PRT
<213> ORGANISM: Artificial
<220> FEATURE:
<223> OTHER INFORMATION: U 1 - 7-CDR-3l

<400> SEQUENCE: 276

Leu Gln His Asn Ser Tyr Pro Trp Thr
1               5
```

<210> SEQ ID NO 277
<211> LENGTH: 10
<212> TYPE: PRT
<213> ORGANISM: Artificial
<220> FEATURE:
<223> OTHER INFORMATION: U 1 - 8-CDR-1h

<400> SEQUENCE: 277

Gly Tyr Thr Leu Thr Glu Leu Ser Met Tyr
1               5                   10

<210> SEQ ID NO 278
<211> LENGTH: 17
<212> TYPE: PRT
<213> ORGANISM: Artificial
<220> FEATURE:
<223> OTHER INFORMATION: U 1 - 8-CDR-2h

<400> SEQUENCE: 278

Gly Phe Asp Pro Glu Asp Gly Glu Thr Ile Tyr Ala Gln Lys Phe Gln
1               5                   10                  15

Gly

<210> SEQ ID NO 279
<211> LENGTH: 8
<212> TYPE: PRT
<213> ORGANISM: Artificial
<220> FEATURE:
<223> OTHER INFORMATION: U 1 - 8-CDR-3h

<400> SEQUENCE: 279

Gly Trp Asn Tyr Val Phe Asp Tyr
1               5

<210> SEQ ID NO 280
<211> LENGTH: 16
<212> TYPE: PRT
<213> ORGANISM: Artificial
<220> FEATURE:
<223> OTHER INFORMATION: U 1 - 8-CDR-1l

<400> SEQUENCE: 280

Arg Ser Ser Gln Ser Leu Leu His Ser Asn Gly Tyr Asn Tyr Leu Asp
1               5                   10                  15

<210> SEQ ID NO 281
<211> LENGTH: 7
<212> TYPE: PRT
<213> ORGANISM: Artificial
<220> FEATURE:
<223> OTHER INFORMATION: U 1 - 8-CDR-2l

<400> SEQUENCE: 281

Leu Asp Ser His Arg Ala Ser
1               5

<210> SEQ ID NO 282
<211> LENGTH: 9
<212> TYPE: PRT
<213> ORGANISM: Artificial
<220> FEATURE:
<223> OTHER INFORMATION: U 1 - 8-CDR-3l

<400> SEQUENCE: 282

Met Gln Ala Leu Gln Thr Pro Leu Thr
1               5

<210> SEQ ID NO 283
<211> LENGTH: 12
<212> TYPE: PRT
<213> ORGANISM: Artificial
<220> FEATURE:
<223> OTHER INFORMATION: U 1 - 9-CDR-1h

<400> SEQUENCE: 283

Gly Gly Ser Ile Ser Ser Gly Asp Tyr Tyr Trp Ser
1               5                   10

<210> SEQ ID NO 284
<211> LENGTH: 16
<212> TYPE: PRT
<213> ORGANISM: Artificial
<220> FEATURE:
<223> OTHER INFORMATION: U 1 - 9-CDR-2h

<400> SEQUENCE: 284

Tyr Ile Tyr Tyr Ser Gly Ser Thr Tyr Tyr Asn Pro Ser Leu Lys Ser
1               5                   10                  15

<210> SEQ ID NO 285
<211> LENGTH: 12
<212> TYPE: PRT
<213> ORGANISM: Artificial
<220> FEATURE:
<223> OTHER INFORMATION: U 1 - 9-CDR-3h

<400> SEQUENCE: 285

Ala Asp Tyr Asp Phe Trp Asn Gly Tyr Phe Asp Tyr
1               5                   10

<210> SEQ ID NO 286
<211> LENGTH: 11
<212> TYPE: PRT
<213> ORGANISM: Artificial
<220> FEATURE:
<223> OTHER INFORMATION: U 1 - 9-CDR-1l

<400> SEQUENCE: 286

Arg Ala Ser Gln Asp Ile Arg Asn Asp Leu Gly
1               5                   10

<210> SEQ ID NO 287
<211> LENGTH: 7
<212> TYPE: PRT
<213> ORGANISM: Artificial
<220> FEATURE:
<223> OTHER INFORMATION: U 1 - 9-CDR-2l

<400> SEQUENCE: 287

Ala Ala Ser Ser Leu Gln Ser
1               5

<210> SEQ ID NO 288
<211> LENGTH: 9
<212> TYPE: PRT
<213> ORGANISM: Artificial
<220> FEATURE:
<223> OTHER INFORMATION: U 1 - 9-CDR-3l

<400> SEQUENCE: 288

Leu Gln His Asn Ser Tyr Pro Trp Thr
1               5

<210> SEQ ID NO 289
<211> LENGTH: 12
<212> TYPE: PRT
<213> ORGANISM: Artificial
<220> FEATURE:
<223> OTHER INFORMATION: U1-10-CDR-1h

<400> SEQUENCE: 289

Gly Gly Ser Ile Ser Ser Gly Asp Tyr Tyr Trp Ser
1               5                   10

<210> SEQ ID NO 290
<211> LENGTH: 16
<212> TYPE: PRT
<213> ORGANISM: Artificial
<220> FEATURE:
<223> OTHER INFORMATION: U1-10-CDR-2h

<400> SEQUENCE: 290

Tyr Ile Tyr Tyr Ser Gly Ser Thr Tyr Tyr Asn Pro Ser Leu Lys Ser
1               5                   10                  15

<210> SEQ ID NO 291
<211> LENGTH: 12
<212> TYPE: PRT
<213> ORGANISM: Artificial
<220> FEATURE:
<223> OTHER INFORMATION: U1-10-CDR-3h

<400> SEQUENCE: 291

Ala Asp Tyr Asp Phe Trp Ser Gly Tyr Phe Asp Tyr
1               5                   10

<210> SEQ ID NO 292
<211> LENGTH: 11
<212> TYPE: PRT
<213> ORGANISM: Artificial
<220> FEATURE:
<223> OTHER INFORMATION: U1-10-CDR-1l

<400> SEQUENCE: 292

Arg Ala Ser Gln Gly Ile Arg Asn Asp Leu Gly
1               5                   10

<210> SEQ ID NO 293
<211> LENGTH: 7
<212> TYPE: PRT
<213> ORGANISM: Artificial
<220> FEATURE:
<223> OTHER INFORMATION: U1-10-CDR-2l

<400> SEQUENCE: 293

Ala Ala Ser Ser Leu Gln Ser
1               5

<210> SEQ ID NO 294
<211> LENGTH: 9
<212> TYPE: PRT
<213> ORGANISM: Artificial
<220> FEATURE:
<223> OTHER INFORMATION: U1-10-CDR-3l

<400> SEQUENCE: 294

Leu Gln His Asn Asn Tyr Pro Trp Thr
1               5

```
<210> SEQ ID NO 295
<211> LENGTH: 12
<212> TYPE: PRT
<213> ORGANISM: Artificial
<220> FEATURE:
<223> OTHER INFORMATION: U 1 -11-CDR-1h

<400> SEQUENCE: 295

Gly Gly Ser Ile Ser Ser Gly Asp Tyr Tyr Trp Ser
1               5                   10

<210> SEQ ID NO 296
<211> LENGTH: 16
<212> TYPE: PRT
<213> ORGANISM: Artificial
<220> FEATURE:
<223> OTHER INFORMATION: U 1 -11-CDR-2h

<400> SEQUENCE: 296

Tyr Ile Tyr Tyr Ser Gly Ser Thr Tyr Tyr Asn Pro Ser Leu Lys Ser
1               5                   10                  15

<210> SEQ ID NO 297
<211> LENGTH: 12
<212> TYPE: PRT
<213> ORGANISM: Artificial
<220> FEATURE:
<223> OTHER INFORMATION: U 1 -11-CDR-3h

<400> SEQUENCE: 297

Ala Asp Tyr Asp Phe Trp Ser Gly Tyr Phe Asp Tyr
1               5                   10

<210> SEQ ID NO 298
<211> LENGTH: 11
<212> TYPE: PRT
<213> ORGANISM: Artificial
<220> FEATURE:
<223> OTHER INFORMATION: U 1 -11-CDR-1l

<400> SEQUENCE: 298

Arg Ala Ser Gln Gly Ile Arg Asn Asp Leu Gly
1               5                   10

<210> SEQ ID NO 299
<211> LENGTH: 7
<212> TYPE: PRT
<213> ORGANISM: Artificial
<220> FEATURE:
<223> OTHER INFORMATION: U 1 -11-CDR-2l

<400> SEQUENCE: 299

Ala Ala Ser Ser Leu Gln Ser
1               5

<210> SEQ ID NO 300
<211> LENGTH: 9
<212> TYPE: PRT
<213> ORGANISM: Artificial
<220> FEATURE:
<223> OTHER INFORMATION: U 1 -11-CDR-3l

<400> SEQUENCE: 300

Leu Gln His Asn Thr Tyr Pro Trp Thr
1               5

<210> SEQ ID NO 301
```

```
<211> LENGTH: 12
<212> TYPE: PRT
<213> ORGANISM: Artificial
<220> FEATURE:
<223> OTHER INFORMATION: U 1 - 12-CDR-1h

<400> SEQUENCE: 301

Gly Gly Ser Ile Ser Ser Gly Asp Tyr Tyr Trp Ser
1               5                   10

<210> SEQ ID NO 302
<211> LENGTH: 16
<212> TYPE: PRT
<213> ORGANISM: Artificial
<220> FEATURE:
<223> OTHER INFORMATION: U 1 - 12-CDR-2h

<400> SEQUENCE: 302

Tyr Ile Tyr Tyr Ser Gly Ser Thr Tyr Tyr Asn Pro Ser Leu Lys Ser
1               5                   10                  15

<210> SEQ ID NO 303
<211> LENGTH: 12
<212> TYPE: PRT
<213> ORGANISM: Artificial
<220> FEATURE:
<223> OTHER INFORMATION: U1-12-CDR-3h

<400> SEQUENCE: 303

Ala Asp Tyr Asp Phe Trp Ser Gly Tyr Phe Asp Tyr
1               5                   10

<210> SEQ ID NO 304
<211> LENGTH: 11
<212> TYPE: PRT
<213> ORGANISM: Artificial
<220> FEATURE:
<223> OTHER INFORMATION: U1-12-CDR-1l

<400> SEQUENCE: 304

Arg Ala Ser Gln Gly Ile Arg Asn Asp Leu Gly
1               5                   10

<210> SEQ ID NO 305
<211> LENGTH: 7
<212> TYPE: PRT
<213> ORGANISM: Artificial
<220> FEATURE:
<223> OTHER INFORMATION: U1-12-CDR-2l

<400> SEQUENCE: 305

Ala Ala Ser Ser Leu Gln Ser
1               5

<210> SEQ ID NO 306
<211> LENGTH: 9
<212> TYPE: PRT
<213> ORGANISM: Artificial
<220> FEATURE:
<223> OTHER INFORMATION: U1-12-CDR-3l

<400> SEQUENCE: 306

Leu Gln His Asn Asn Tyr Pro Trp Thr
1               5

<210> SEQ ID NO 307
<211> LENGTH: 12
```

```
<212> TYPE: PRT
<213> ORGANISM: Artificial
<220> FEATURE:
<223> OTHER INFORMATION: U 1-13-CDR-1h

<400> SEQUENCE: 307

Gly Gly Ser Ile Ser Ser Gly Gly Tyr Tyr Trp Ser
1               5                   10

<210> SEQ ID NO 308
<211> LENGTH: 16
<212> TYPE: PRT
<213> ORGANISM: Artificial
<220> FEATURE:
<223> OTHER INFORMATION: U 1-13-CDR-2h

<400> SEQUENCE: 308

Tyr Ile Tyr Tyr Ser Gly Ser Thr Tyr Tyr Asn Pro Ser Leu Lys Ser
1               5                   10                  15

<210> SEQ ID NO 309
<211> LENGTH: 7
<212> TYPE: PRT
<213> ORGANISM: Artificial
<220> FEATURE:
<223> OTHER INFORMATION: U 1-13-CDR-3h

<400> SEQUENCE: 309

Glu Asp Asp Gly Met Asp Val
1               5

<210> SEQ ID NO 310
<211> LENGTH: 16
<212> TYPE: PRT
<213> ORGANISM: Artificial
<220> FEATURE:
<223> OTHER INFORMATION: U 1-13-CDR-1l

<400> SEQUENCE: 310

Arg Ser Ser Gln Ser Leu Leu His Ser Asn Gly Tyr Asn Tyr Leu Glu
1               5                   10                  15

<210> SEQ ID NO 311
<211> LENGTH: 7
<212> TYPE: PRT
<213> ORGANISM: Artificial
<220> FEATURE:
<223> OTHER INFORMATION: U 1-13-CDR-2l

<400> SEQUENCE: 311

Leu Gly Ser Asn Arg Ala Ser
1               5

<210> SEQ ID NO 312
<211> LENGTH: 9
<212> TYPE: PRT
<213> ORGANISM: Artificial
<220> FEATURE:
<223> OTHER INFORMATION: U 1-13-CDR-3l

<400> SEQUENCE: 312

Met Gln Ala Leu Gln Thr Pro Ile Thr
1               5

<210> SEQ ID NO 313
<211> LENGTH: 12
<212> TYPE: PRT
```

```
<213> ORGANISM: Artificial
<220> FEATURE:
<223> OTHER INFORMATION: U1-14-CDR-1h

<400> SEQUENCE: 313

Gly Gly Ser Ile Ser Ser Gly Asp Tyr Tyr Trp Ser
1               5                   10

<210> SEQ ID NO 314
<211> LENGTH: 16
<212> TYPE: PRT
<213> ORGANISM: Artificial
<220> FEATURE:
<223> OTHER INFORMATION: U1-14-CDR-2h

<400> SEQUENCE: 314

Tyr Ile Tyr Tyr Ser Gly Ser Thr Tyr Tyr Asn Pro Ser Leu Lys Ser
1               5                   10                  15

<210> SEQ ID NO 315
<211> LENGTH: 12
<212> TYPE: PRT
<213> ORGANISM: Artificial
<220> FEATURE:
<223> OTHER INFORMATION: U1-14-CDR-3h

<400> SEQUENCE: 315

Ala Asp Tyr Asp Phe Trp Ser Gly Tyr Phe Asp Tyr
1               5                   10

<210> SEQ ID NO 316
<211> LENGTH: 11
<212> TYPE: PRT
<213> ORGANISM: Artificial
<220> FEATURE:
<223> OTHER INFORMATION: U1-14-CDR-1l

<400> SEQUENCE: 316

Arg Ala Ser Gln Gly Ile Arg Asn Asp Leu Gly
1               5                   10

<210> SEQ ID NO 317
<211> LENGTH: 7
<212> TYPE: PRT
<213> ORGANISM: Artificial
<220> FEATURE:
<223> OTHER INFORMATION: U1-14-CDR-2l

<400> SEQUENCE: 317

Ala Ala Ser Ser Leu Gln Ser
1               5

<210> SEQ ID NO 318
<211> LENGTH: 9
<212> TYPE: PRT
<213> ORGANISM: Artificial
<220> FEATURE:
<223> OTHER INFORMATION: U1-14-CDR-3l

<400> SEQUENCE: 318

Leu Gln His Asn Thr Tyr Pro Trp Thr
1               5

<210> SEQ ID NO 319
<211> LENGTH: 12
<212> TYPE: PRT
<213> ORGANISM: Artificial
```

<220> FEATURE:
<223> OTHER INFORMATION: U1-15-CDR-1h

<400> SEQUENCE: 319

Gly Gly Ser Val Ser Ser Gly Gly Tyr Tyr Trp Ser
1               5                   10

<210> SEQ ID NO 320
<211> LENGTH: 16
<212> TYPE: PRT
<213> ORGANISM: Artificial
<220> FEATURE:
<223> OTHER INFORMATION: U1-15-CDR-2h

<400> SEQUENCE: 320

Tyr Ile Tyr Tyr Ser Gly Ser Thr Asn Tyr Asn Pro Ser Leu Lys Ser
1               5                   10                  15

<210> SEQ ID NO 321
<211> LENGTH: 14
<212> TYPE: PRT
<213> ORGANISM: Artificial
<220> FEATURE:
<223> OTHER INFORMATION: U1-15-CDR-3h

<400> SEQUENCE: 321

Asp Gly Asp Val Asp Thr Ala Met Val Asp Ala Phe Asp Ile
1               5                   10

<210> SEQ ID NO 322
<211> LENGTH: 12
<212> TYPE: PRT
<213> ORGANISM: Artificial
<220> FEATURE:
<223> OTHER INFORMATION: U1-15-CDR-1l

<400> SEQUENCE: 322

Arg Ala Ser Gln Ser Leu Ser Gly Asn Tyr Leu Ala
1               5                   10

<210> SEQ ID NO 323
<211> LENGTH: 7
<212> TYPE: PRT
<213> ORGANISM: Artificial
<220> FEATURE:
<223> OTHER INFORMATION: U1-15-CDR-2l

<400> SEQUENCE: 323

Gly Ala Ser Ser Arg Ala Thr
1               5

<210> SEQ ID NO 324
<211> LENGTH: 9
<212> TYPE: PRT
<213> ORGANISM: Artificial
<220> FEATURE:
<223> OTHER INFORMATION: U1-15-CDR-3l

<400> SEQUENCE: 324

Gln Gln Tyr Asp Arg Ser Pro Leu Thr
1               5

<210> SEQ ID NO 325
<211> LENGTH: 12
<212> TYPE: PRT
<213> ORGANISM: Artificial
<220> FEATURE:

<223> OTHER INFORMATION: U1-16-CDR-1h

<400> SEQUENCE: 325

Gly Gly Ser Ile Ser Ser Gly Asp Tyr Tyr Trp Ser
1               5                   10

<210> SEQ ID NO 326
<211> LENGTH: 16
<212> TYPE: PRT
<213> ORGANISM: Artificial
<220> FEATURE:
<223> OTHER INFORMATION: U1-16-CDR-2h

<400> SEQUENCE: 326

Tyr Ile Tyr Tyr Ser Gly Ser Thr Tyr Tyr Asn Pro Ser Leu Lys Ser
1               5                   10                  15

<210> SEQ ID NO 327
<211> LENGTH: 12
<212> TYPE: PRT
<213> ORGANISM: Artificial
<220> FEATURE:
<223> OTHER INFORMATION: U1-16-CDR-3h

<400> SEQUENCE: 327

Ala Asp Tyr Asp Phe Trp Ser Gly Tyr Phe Asp Tyr
1               5                   10

<210> SEQ ID NO 328
<211> LENGTH: 11
<212> TYPE: PRT
<213> ORGANISM: Artificial
<220> FEATURE:
<223> OTHER INFORMATION: U1-16-CDR-1l

<400> SEQUENCE: 328

Arg Ala Ser Gln Gly Ile Arg Asn Asp Leu Gly
1               5                   10

<210> SEQ ID NO 329
<211> LENGTH: 7
<212> TYPE: PRT
<213> ORGANISM: Artificial
<220> FEATURE:
<223> OTHER INFORMATION: U1-16-CDR-2l

<400> SEQUENCE: 329

Ala Ala Ser Ser Leu Gln Ser
1               5

<210> SEQ ID NO 330
<211> LENGTH: 9
<212> TYPE: PRT
<213> ORGANISM: Artificial
<220> FEATURE:
<223> OTHER INFORMATION: U1-16-CDR-3l

<400> SEQUENCE: 330

Leu Gln His Asn Ser Tyr Pro Trp Thr
1               5

<210> SEQ ID NO 331
<211> LENGTH: 12
<212> TYPE: PRT
<213> ORGANISM: Artificial
<220> FEATURE:
<223> OTHER INFORMATION: U1-17-CDR-1h

```
<400> SEQUENCE: 331

Gly Gly Ser Ile Ser Ser Gly Asp Tyr Tyr Trp Ser
1               5                   10

<210> SEQ ID NO 332
<211> LENGTH: 16
<212> TYPE: PRT
<213> ORGANISM: Artificial
<220> FEATURE:
<223> OTHER INFORMATION: U1-17-CDR-2h

<400> SEQUENCE: 332

Tyr Ile Tyr Tyr Ser Gly Ser Thr Tyr Tyr Asn Ser Ser Leu Lys Ser
1               5                   10                  15

<210> SEQ ID NO 333
<211> LENGTH: 12
<212> TYPE: PRT
<213> ORGANISM: Artificial
<220> FEATURE:
<223> OTHER INFORMATION: U1-17-CDR-3h

<400> SEQUENCE: 333

Ala Asp Tyr Asp Phe Trp Ser Gly Tyr Phe Asp Tyr
1               5                   10

<210> SEQ ID NO 334
<211> LENGTH: 11
<212> TYPE: PRT
<213> ORGANISM: Artificial
<220> FEATURE:
<223> OTHER INFORMATION: U1-17-CDR-1l

<400> SEQUENCE: 334

Arg Ala Ser Gln Gly Ile Arg Asn Asp Leu Gly
1               5                   10

<210> SEQ ID NO 335
<211> LENGTH: 7
<212> TYPE: PRT
<213> ORGANISM: Artificial
<220> FEATURE:
<223> OTHER INFORMATION: U1-17-CDR-2l

<400> SEQUENCE: 335

Ala Ala Ser Ser Leu Gln Ser
1               5

<210> SEQ ID NO 336
<211> LENGTH: 9
<212> TYPE: PRT
<213> ORGANISM: Artificial
<220> FEATURE:
<223> OTHER INFORMATION: U1-17-CDR-3l

<400> SEQUENCE: 336

Leu Gln His Asn Ser Tyr Pro Trp Thr
1               5

<210> SEQ ID NO 337
<211> LENGTH: 12
<212> TYPE: PRT
<213> ORGANISM: Artificial
<220> FEATURE:
<223> OTHER INFORMATION: U1-18-CDR-1h
```

```
<400> SEQUENCE: 337

Gly Gly Ser Ile Ser Ser Gly Asp Tyr Tyr Trp Ser
1               5                   10

<210> SEQ ID NO 338
<211> LENGTH: 16
<212> TYPE: PRT
<213> ORGANISM: Artificial
<220> FEATURE:
<223> OTHER INFORMATION: U1-18-CDR-2h

<400> SEQUENCE: 338

Tyr Ile Tyr Tyr Ser Gly Ser Thr Tyr Tyr Asn Pro Ser Leu Lys Ser
1               5                   10                  15

<210> SEQ ID NO 339
<211> LENGTH: 12
<212> TYPE: PRT
<213> ORGANISM: Artificial
<220> FEATURE:
<223> OTHER INFORMATION: U1-18-CDR-3h

<400> SEQUENCE: 339

Ala Asp Tyr Asp Phe Trp Ser Gly Tyr Phe Asp Tyr
1               5                   10

<210> SEQ ID NO 340
<211> LENGTH: 11
<212> TYPE: PRT
<213> ORGANISM: Artificial
<220> FEATURE:
<223> OTHER INFORMATION: U1-18-CDR-1l

<400> SEQUENCE: 340

Arg Ala Ser Gln Gly Ile Arg Asn Asp Leu Gly
1               5                   10

<210> SEQ ID NO 341
<211> LENGTH: 7
<212> TYPE: PRT
<213> ORGANISM: Artificial
<220> FEATURE:
<223> OTHER INFORMATION: U1-18-CDR-2l

<400> SEQUENCE: 341

Ala Ala Ser Ser Leu Gln Ser
1               5

<210> SEQ ID NO 342
<211> LENGTH: 9
<212> TYPE: PRT
<213> ORGANISM: Artificial
<220> FEATURE:
<223> OTHER INFORMATION: U1-18-CDR-3l

<400> SEQUENCE: 342

Leu Gln His Asn Ser Tyr Pro Trp Thr
1               5

<210> SEQ ID NO 343
<211> LENGTH: 12
<212> TYPE: PRT
<213> ORGANISM: Artificial
<220> FEATURE:
<223> OTHER INFORMATION: U1-19-CDR-1h

<400> SEQUENCE: 343
```

```
Gly Gly Ser Ile Ser Ser Gly Asp Tyr Tyr Trp Ser
1               5                   10

<210> SEQ ID NO 344
<211> LENGTH: 16
<212> TYPE: PRT
<213> ORGANISM: Artificial
<220> FEATURE:
<223> OTHER INFORMATION: U1-19-CDR-2h

<400> SEQUENCE: 344

Tyr Ile Tyr Tyr Ser Gly Ser Thr Tyr Tyr Asn Pro Ser Leu Lys Ser
1               5                   10                  15

<210> SEQ ID NO 345
<211> LENGTH: 12
<212> TYPE: PRT
<213> ORGANISM: Artificial
<220> FEATURE:
<223> OTHER INFORMATION: U1-19-CDR-3h

<400> SEQUENCE: 345

Gly Asp Tyr Asp Phe Trp Ser Gly Glu Phe Asp Tyr
1               5                   10

<210> SEQ ID NO 346
<211> LENGTH: 12
<212> TYPE: PRT
<213> ORGANISM: Artificial
<220> FEATURE:
<223> OTHER INFORMATION: U1-20-CDR-1h

<400> SEQUENCE: 346

Gly Gly Ser Ile Ser Ser Gly Gly Tyr Tyr Trp Ser
1               5                   10

<210> SEQ ID NO 347
<211> LENGTH: 16
<212> TYPE: PRT
<213> ORGANISM: Artificial
<220> FEATURE:
<223> OTHER INFORMATION: U1-20-CDR-2h

<400> SEQUENCE: 347

Tyr Ile Tyr Asp Ser Gly Ser Thr Tyr Tyr Asn Pro Ser Leu Lys Ser
1               5                   10                  15

<210> SEQ ID NO 348
<211> LENGTH: 19
<212> TYPE: PRT
<213> ORGANISM: Artificial
<220> FEATURE:
<223> OTHER INFORMATION: U1-20-CDR-3h

<400> SEQUENCE: 348

Asp Gln Gly Gln Asp Gly Tyr Ser Tyr Gly Tyr Gly Tyr Tyr Gly
1               5                   10                  15

Met Asp Val

<210> SEQ ID NO 349
<211> LENGTH: 11
<212> TYPE: PRT
<213> ORGANISM: Artificial
<220> FEATURE:
<223> OTHER INFORMATION: U1-20-CDR-1l
```

<400> SEQUENCE: 349

Gln Ala Ser Gln Asp Ile Ser Asn Tyr Leu Asn
1               5                   10

<210> SEQ ID NO 350
<211> LENGTH: 7
<212> TYPE: PRT
<213> ORGANISM: Artificial
<220> FEATURE:
<223> OTHER INFORMATION: U1-20-CDR-2l

<400> SEQUENCE: 350

Val Ala Ser Asn Leu Glu Thr
1               5

<210> SEQ ID NO 351
<211> LENGTH: 9
<212> TYPE: PRT
<213> ORGANISM: Artificial
<220> FEATURE:
<223> OTHER INFORMATION: U1-20-CDR-3l

<400> SEQUENCE: 351

Gln Gln Cys Asp Asn Leu Pro Leu Thr
1               5

<210> SEQ ID NO 352
<211> LENGTH: 12
<212> TYPE: PRT
<213> ORGANISM: Artificial
<220> FEATURE:
<223> OTHER INFORMATION: U1-21-CDR-1h

<400> SEQUENCE: 352

Gly Gly Ser Ile Ser Ser Gly Asp Tyr Tyr Trp Ser
1               5                   10

<210> SEQ ID NO 353
<211> LENGTH: 16
<212> TYPE: PRT
<213> ORGANISM: Artificial
<220> FEATURE:
<223> OTHER INFORMATION: U1-21-CDR-2h

<400> SEQUENCE: 353

Tyr Ile Tyr Tyr Ser Gly Ser Thr Tyr Tyr Asn Pro Ser Leu Lys Ser
1               5                   10                  15

<210> SEQ ID NO 354
<211> LENGTH: 12
<212> TYPE: PRT
<213> ORGANISM: Artificial
<220> FEATURE:
<223> OTHER INFORMATION: U1-21-CDR-3h

<400> SEQUENCE: 354

Ala Asp Tyr Asp Phe Trp Ser Gly Tyr Phe Asp Tyr
1               5                   10

<210> SEQ ID NO 355
<211> LENGTH: 11
<212> TYPE: PRT
<213> ORGANISM: Artificial
<220> FEATURE:
<223> OTHER INFORMATION: U1-21-CDR-1l

<400> SEQUENCE: 355

Arg Ala Ser Gln Asp Ile Arg Asn Asp Leu Gly
1               5                   10

<210> SEQ ID NO 356
<211> LENGTH: 7
<212> TYPE: PRT
<213> ORGANISM: Artificial
<220> FEATURE:
<223> OTHER INFORMATION: U1-21-CDR-2l

<400> SEQUENCE: 356

Ala Ala Ser Arg Leu Gln Ser
1               5

<210> SEQ ID NO 357
<211> LENGTH: 9
<212> TYPE: PRT
<213> ORGANISM: Artificial
<220> FEATURE:
<223> OTHER INFORMATION: U1-21-CDR-3l

<400> SEQUENCE: 357

Leu Gln His Asn Ser Tyr Pro Trp Thr
1               5

<210> SEQ ID NO 358
<211> LENGTH: 12
<212> TYPE: PRT
<213> ORGANISM: Artificial
<220> FEATURE:
<223> OTHER INFORMATION: U1-22-CDR-1h

<400> SEQUENCE: 358

Gly Gly Ser Ile Ser Ser Gly Asp Tyr Tyr Trp Ser
1               5                   10

<210> SEQ ID NO 359
<211> LENGTH: 16
<212> TYPE: PRT
<213> ORGANISM: Artificial
<220> FEATURE:
<223> OTHER INFORMATION: U1-22-CDR-2h

<400> SEQUENCE: 359

Tyr Ile Tyr Tyr Ser Gly Ser Thr Tyr Tyr Asn Pro Ser Leu Lys Ser
1               5                   10                  15

<210> SEQ ID NO 360
<211> LENGTH: 12
<212> TYPE: PRT
<213> ORGANISM: Artificial
<220> FEATURE:
<223> OTHER INFORMATION: U1-22-CDR-3h

<400> SEQUENCE: 360

Ala Asp Tyr Asp Phe Trp Ser Gly Tyr Phe Asp Tyr
1               5                   10

<210> SEQ ID NO 361
<211> LENGTH: 11
<212> TYPE: PRT
<213> ORGANISM: Artificial
<220> FEATURE:
<223> OTHER INFORMATION: U1-22-CDR-1l

<400> SEQUENCE: 361

Arg Ala Ser Gln Gly Ile Arg Asn Asp Leu Gly
1               5                   10

<210> SEQ ID NO 362
<211> LENGTH: 7
<212> TYPE: PRT
<213> ORGANISM: Artificial
<220> FEATURE:
<223> OTHER INFORMATION: U1-22-CDR-2l

<400> SEQUENCE: 362

Ala Ala Ser Ser Leu Gln Asn
1               5

<210> SEQ ID NO 363
<211> LENGTH: 9
<212> TYPE: PRT
<213> ORGANISM: Artificial
<220> FEATURE:
<223> OTHER INFORMATION: U1-22-CDR-3l

<400> SEQUENCE: 363

Leu Gln His Asn Ser Tyr Pro Trp Thr
1               5

<210> SEQ ID NO 364
<211> LENGTH: 12
<212> TYPE: PRT
<213> ORGANISM: Artificial
<220> FEATURE:
<223> OTHER INFORMATION: U1-23-CDR-1h

<400> SEQUENCE: 364

Gly Gly Ser Ile Ser Ser Gly Asp Tyr Tyr Trp Ser
1               5                   10

<210> SEQ ID NO 365
<211> LENGTH: 16
<212> TYPE: PRT
<213> ORGANISM: Artificial
<220> FEATURE:
<223> OTHER INFORMATION: U1-23-CDR-2h

<400> SEQUENCE: 365

Tyr Ile Tyr Tyr Ser Gly Ser Thr Tyr Tyr Asn Pro Ser Leu Lys Ser
1               5                   10                  15

<210> SEQ ID NO 366
<211> LENGTH: 12
<212> TYPE: PRT
<213> ORGANISM: Artificial
<220> FEATURE:
<223> OTHER INFORMATION: U1-23-CDR-3h

<400> SEQUENCE: 366

Ala Asp Tyr Asp Phe Trp Ser Gly Tyr Phe Asp Tyr
1               5                   10

<210> SEQ ID NO 367
<211> LENGTH: 11
<212> TYPE: PRT
<213> ORGANISM: Artificial
<220> FEATURE:
<223> OTHER INFORMATION: U1-23-CDR-1l

<400> SEQUENCE: 367

Arg Ala Ser Gln Gly Ile Arg Asn Asp Leu Gly

```
<210> SEQ ID NO 368
<211> LENGTH: 7
<212> TYPE: PRT
<213> ORGANISM: Artificial
<220> FEATURE:
<223> OTHER INFORMATION: U1-23-CDR-2l

<400> SEQUENCE: 368

Ala Ala Ser Ser Leu Gln Ser
1               5

<210> SEQ ID NO 369
<211> LENGTH: 9
<212> TYPE: PRT
<213> ORGANISM: Artificial
<220> FEATURE:
<223> OTHER INFORMATION: U1-23-CDR-3l

<400> SEQUENCE: 369

Leu Gln His Asn Ser Tyr Pro Trp Thr
1               5

<210> SEQ ID NO 370
<211> LENGTH: 12
<212> TYPE: PRT
<213> ORGANISM: Artificial
<220> FEATURE:
<223> OTHER INFORMATION: U1-24-CDR-1h

<400> SEQUENCE: 370

Gly Gly Ser Ile Ser Ser Gly Asp Tyr Tyr Trp Ser
1               5                   10

<210> SEQ ID NO 371
<211> LENGTH: 16
<212> TYPE: PRT
<213> ORGANISM: Artificial
<220> FEATURE:
<223> OTHER INFORMATION: U1-24-CDR-2h

<400> SEQUENCE: 371

Tyr Ile Tyr Tyr Ser Gly Ser Thr Tyr Tyr Asn Pro Ser Leu Lys Ser
1               5                   10                  15

<210> SEQ ID NO 372
<211> LENGTH: 12
<212> TYPE: PRT
<213> ORGANISM: Artificial
<220> FEATURE:
<223> OTHER INFORMATION: U1-24-CDR-3h

<400> SEQUENCE: 372

Ala Asp Tyr Asp Phe Trp Asn Gly Tyr Phe Asp Tyr
1               5                   10

<210> SEQ ID NO 373
<211> LENGTH: 11
<212> TYPE: PRT
<213> ORGANISM: Artificial
<220> FEATURE:
<223> OTHER INFORMATION: U1-24-CDR-1l

<400> SEQUENCE: 373

Arg Ala Ser Gln Gly Ile Arg Asn Asp Leu Gly
1               5                   10
```

<210> SEQ ID NO 374
<211> LENGTH: 7
<212> TYPE: PRT
<213> ORGANISM: Artificial
<220> FEATURE:
<223> OTHER INFORMATION: U1-24-CDR-2l

<400> SEQUENCE: 374

Ala Ala Ser Ser Leu Gln Ser
1               5

<210> SEQ ID NO 375
<211> LENGTH: 9
<212> TYPE: PRT
<213> ORGANISM: Artificial
<220> FEATURE:
<223> OTHER INFORMATION: U1-24-CDR-3l

<400> SEQUENCE: 375

Leu Gln His Asn Asn Tyr Pro Trp Thr
1               5

<210> SEQ ID NO 376
<211> LENGTH: 12
<212> TYPE: PRT
<213> ORGANISM: Artificial
<220> FEATURE:
<223> OTHER INFORMATION: U1-25-CDR-1h

<400> SEQUENCE: 376

Gly Gly Ser Ile Ser Ser Gly Asp Tyr Tyr Trp Ser
1               5                   10

<210> SEQ ID NO 377
<211> LENGTH: 16
<212> TYPE: PRT
<213> ORGANISM: Artificial
<220> FEATURE:
<223> OTHER INFORMATION: U1-25-CDR-2h

<400> SEQUENCE: 377

Tyr Ile Tyr Tyr Ser Gly Ser Thr Tyr Tyr Asn Pro Ser Leu Lys Ser
1               5                   10                  15

<210> SEQ ID NO 378
<211> LENGTH: 12
<212> TYPE: PRT
<213> ORGANISM: Artificial
<220> FEATURE:
<223> OTHER INFORMATION: U1-25-CDR-3h

<400> SEQUENCE: 378

Ala Asp Tyr Asp Phe Trp Ser Gly Tyr Phe Asp Tyr
1               5                   10

<210> SEQ ID NO 379
<211> LENGTH: 11
<212> TYPE: PRT
<213> ORGANISM: Artificial
<220> FEATURE:
<223> OTHER INFORMATION: U1-25-CDR-1l

<400> SEQUENCE: 379

Arg Ala Ser Gln Gly Ile Arg Asn Asp Leu Gly
1               5                   10

```
<210> SEQ ID NO 380
<211> LENGTH: 7
<212> TYPE: PRT
<213> ORGANISM: Artificial
<220> FEATURE:
<223> OTHER INFORMATION: U1-25-CDR-2l

<400> SEQUENCE: 380

Ala Ala Ser Ser Leu Gln Asn
1               5

<210> SEQ ID NO 381
<211> LENGTH: 9
<212> TYPE: PRT
<213> ORGANISM: Artificial
<220> FEATURE:
<223> OTHER INFORMATION: U1-25-CDR-3l

<400> SEQUENCE: 381

Leu Gln His Asn Ser Tyr Pro Trp Thr
1               5

<210> SEQ ID NO 382
<211> LENGTH: 12
<212> TYPE: PRT
<213> ORGANISM: Artificial
<220> FEATURE:
<223> OTHER INFORMATION: U1-26-CDR-1h

<400> SEQUENCE: 382

Gly Gly Ser Ile Ser Ser Gly Asp Tyr Tyr Trp Ser
1               5                   10

<210> SEQ ID NO 383
<211> LENGTH: 16
<212> TYPE: PRT
<213> ORGANISM: Artificial
<220> FEATURE:
<223> OTHER INFORMATION: U1-26-CDR-2h

<400> SEQUENCE: 383

Tyr Ile Tyr Tyr Ser Gly Ser Thr Tyr Tyr Asn Pro Ser Leu Lys Ser
1               5                   10                  15

<210> SEQ ID NO 384
<211> LENGTH: 12
<212> TYPE: PRT
<213> ORGANISM: Artificial
<220> FEATURE:
<223> OTHER INFORMATION: U1-26-CDR-3h

<400> SEQUENCE: 384

Ala Asp Tyr Asp Phe Trp Ser Gly Tyr Phe Asp Phe
1               5                   10

<210> SEQ ID NO 385
<211> LENGTH: 11
<212> TYPE: PRT
<213> ORGANISM: Artificial
<220> FEATURE:
<223> OTHER INFORMATION: U1-26-CDR-1l

<400> SEQUENCE: 385

Arg Ala Ser Gln Gly Ile Arg Asn Asp Leu Gly
1               5                   10
```

```
<210> SEQ ID NO 386
<211> LENGTH: 7
<212> TYPE: PRT
<213> ORGANISM: Artificial
<220> FEATURE:
<223> OTHER INFORMATION: U1-26-CDR-2l

<400> SEQUENCE: 386

Ala Ala Ser Ser Leu Gln Ser
1               5

<210> SEQ ID NO 387
<211> LENGTH: 9
<212> TYPE: PRT
<213> ORGANISM: Artificial
<220> FEATURE:
<223> OTHER INFORMATION: U1-26-CDR-3l

<400> SEQUENCE: 387

Leu Gln His Asn Gly Tyr Pro Trp Thr
1               5

<210> SEQ ID NO 388
<211> LENGTH: 12
<212> TYPE: PRT
<213> ORGANISM: Artificial
<220> FEATURE:
<223> OTHER INFORMATION: U1-27-CDR-1h

<400> SEQUENCE: 388

Gly Gly Ser Ile Ser Ser Gly Asp Tyr Tyr Trp Ser
1               5                   10

<210> SEQ ID NO 389
<211> LENGTH: 16
<212> TYPE: PRT
<213> ORGANISM: Artificial
<220> FEATURE:
<223> OTHER INFORMATION: U1-27-CDR-2h

<400> SEQUENCE: 389

Tyr Ile Tyr Tyr Ser Gly Ser Thr Tyr Tyr Asn Pro Ser Leu Lys Ser
1               5                   10                  15

<210> SEQ ID NO 390
<211> LENGTH: 12
<212> TYPE: PRT
<213> ORGANISM: Artificial
<220> FEATURE:
<223> OTHER INFORMATION: U1-27-CDR-3h

<400> SEQUENCE: 390

Ala Asp Tyr Asp Phe Trp Ser Gly Tyr Phe Asp Phe
1               5                   10

<210> SEQ ID NO 391
<211> LENGTH: 11
<212> TYPE: PRT
<213> ORGANISM: Artificial
<220> FEATURE:
<223> OTHER INFORMATION: U1-27-CDR-1l

<400> SEQUENCE: 391

Arg Ala Ser Gln Gly Ile Arg Asn Asp Leu Gly
1               5                   10

<210> SEQ ID NO 392
```

```
<211> LENGTH: 7
<212> TYPE: PRT
<213> ORGANISM: Artificial
<220> FEATURE:
<223> OTHER INFORMATION: U1-27-CDR-2l

<400> SEQUENCE: 392

Ala Ala Ser Ser Leu Gln Ser
1               5

<210> SEQ ID NO 393
<211> LENGTH: 9
<212> TYPE: PRT
<213> ORGANISM: Artificial
<220> FEATURE:
<223> OTHER INFORMATION: U1-27-CDR-3l

<400> SEQUENCE: 393

Leu Gln His Asn Gly Tyr Pro Trp Thr
1               5

<210> SEQ ID NO 394
<211> LENGTH: 12
<212> TYPE: PRT
<213> ORGANISM: Artificial
<220> FEATURE:
<223> OTHER INFORMATION: U1-28-CDR-1h

<400> SEQUENCE: 394

Gly Gly Ser Ile Ser Ser Gly Asp Tyr Tyr Trp Ser
1               5                   10

<210> SEQ ID NO 395
<211> LENGTH: 16
<212> TYPE: PRT
<213> ORGANISM: Artificial
<220> FEATURE:
<223> OTHER INFORMATION: U1-28-CDR-2h

<400> SEQUENCE: 395

Tyr Ile Tyr Tyr Ser Gly Ser Thr Tyr Tyr Asn Pro Ser Leu Lys Ser
1               5                   10                  15

<210> SEQ ID NO 396
<211> LENGTH: 12
<212> TYPE: PRT
<213> ORGANISM: Artificial
<220> FEATURE:
<223> OTHER INFORMATION: U1-28-CDR-1l

<400> SEQUENCE: 396

Ala Asp Tyr Asp Phe Trp Ser Gly Tyr Phe Asp Ser
1               5                   10

<210> SEQ ID NO 397
<211> LENGTH: 11
<212> TYPE: PRT
<213> ORGANISM: Artificial
<220> FEATURE:
<223> OTHER INFORMATION: U1-28-CDR-1l

<400> SEQUENCE: 397

Arg Ala Ser Gln Gly Ile Arg Asn Asp Leu Gly
1               5                   10

<210> SEQ ID NO 398
<211> LENGTH: 7
```

```
<212> TYPE: PRT
<213> ORGANISM: Artificial
<220> FEATURE:
<223> OTHER INFORMATION: U1-28-CDR-2l

<400> SEQUENCE: 398

Ala Ala Ser Ser Leu Gln Ser
1               5

<210> SEQ ID NO 399
<211> LENGTH: 9
<212> TYPE: PRT
<213> ORGANISM: Artificial
<220> FEATURE:
<223> OTHER INFORMATION: U1-28-CDR-3l

<400> SEQUENCE: 399

Leu Gln His Asn Gly Tyr Pro Trp Thr
1               5

<210> SEQ ID NO 400
<211> LENGTH: 10
<212> TYPE: PRT
<213> ORGANISM: Artificial
<220> FEATURE:
<223> OTHER INFORMATION: U1-29-CDR-1h

<400> SEQUENCE: 400

Gly Phe Thr Phe Asn Ser Tyr Asp Met His
1               5                   10

<210> SEQ ID NO 401
<211> LENGTH: 17
<212> TYPE: PRT
<213> ORGANISM: Artificial
<220> FEATURE:
<223> OTHER INFORMATION: U1-29-CDR-2h

<400> SEQUENCE: 401

Val Ile Trp Tyr Asp Gly Ser Asn Lys Tyr Tyr Ala Asp Ser Val Lys
1               5                   10                  15

Gly

<210> SEQ ID NO 402
<211> LENGTH: 17
<212> TYPE: PRT
<213> ORGANISM: Artificial
<220> FEATURE:
<223> OTHER INFORMATION: U1-29-CDR-3h

<400> SEQUENCE: 402

Asp Arg Leu Cys Thr Asn Gly Val Cys Tyr Glu Asp Tyr Gly Met Asp
1               5                   10                  15

Val

<210> SEQ ID NO 403
<211> LENGTH: 11
<212> TYPE: PRT
<213> ORGANISM: Artificial
<220> FEATURE:
<223> OTHER INFORMATION: U1-29-CDR-1l

<400> SEQUENCE: 403

Gln Ala Ser Gln Asp Ile Ser Asn Tyr Leu Asn
1               5                   10
```

<210> SEQ ID NO 404
<211> LENGTH: 7
<212> TYPE: PRT
<213> ORGANISM: Artificial
<220> FEATURE:
<223> OTHER INFORMATION: U1-29-CDR-2l

<400> SEQUENCE: 404

Asp Ala Ser Asn Leu Glu Thr
1               5

<210> SEQ ID NO 405
<211> LENGTH: 9
<212> TYPE: PRT
<213> ORGANISM: Artificial
<220> FEATURE:
<223> OTHER INFORMATION: U1-29-CDR-3l

<400> SEQUENCE: 405

Gln His Tyr Asp Thr Leu Pro Leu Thr
1               5

<210> SEQ ID NO 406
<211> LENGTH: 12
<212> TYPE: PRT
<213> ORGANISM: Artificial
<220> FEATURE:
<223> OTHER INFORMATION: U1-30-CDR-1h

<400> SEQUENCE: 406

Gly Gly Ser Ile Ser Ser Gly Asp Tyr Tyr Trp Ser
1               5                   10

<210> SEQ ID NO 407
<211> LENGTH: 16
<212> TYPE: PRT
<213> ORGANISM: Artificial
<220> FEATURE:
<223> OTHER INFORMATION: U1-30-CDR-2h

<400> SEQUENCE: 407

Tyr Ile Tyr Tyr Ser Gly Thr Thr Tyr Tyr Asn Pro Ser Leu Lys Ser
1               5                   10                  15

<210> SEQ ID NO 408
<211> LENGTH: 12
<212> TYPE: PRT
<213> ORGANISM: Artificial
<220> FEATURE:
<223> OTHER INFORMATION: U1-30-CDR-3h

<400> SEQUENCE: 408

Ala Asp Tyr Asp Phe Trp Ser Gly Tyr Phe Asp Tyr
1               5                   10

<210> SEQ ID NO 409
<211> LENGTH: 11
<212> TYPE: PRT
<213> ORGANISM: Artificial
<220> FEATURE:
<223> OTHER INFORMATION: U1-30-CDR-1l

<400> SEQUENCE: 409

Arg Ala Gly Gln Gly Ile Arg Asn Asp Leu Gly
1               5                   10

```
<210> SEQ ID NO 410
<211> LENGTH: 7
<212> TYPE: PRT
<213> ORGANISM: Artificial
<220> FEATURE:
<223> OTHER INFORMATION: U1-30-CDR-2l

<400> SEQUENCE: 410

Ala Ala Ser Ser Leu Gln Ser
1               5

<210> SEQ ID NO 411
<211> LENGTH: 9
<212> TYPE: PRT
<213> ORGANISM: Artificial
<220> FEATURE:
<223> OTHER INFORMATION: U1-30-CDR-3l

<400> SEQUENCE: 411

Leu Gln His Asn Ser Tyr Pro Trp Thr
1               5

<210> SEQ ID NO 412
<211> LENGTH: 10
<212> TYPE: PRT
<213> ORGANISM: Artificial
<220> FEATURE:
<223> OTHER INFORMATION: U1-31-CDR-1h

<400> SEQUENCE: 412

Gly Tyr Thr Phe Thr Asn Tyr Gly Ile Ser
1               5                   10

<210> SEQ ID NO 413
<211> LENGTH: 17
<212> TYPE: PRT
<213> ORGANISM: Artificial
<220> FEATURE:
<223> OTHER INFORMATION: U1-31-CDR-2h

<400> SEQUENCE: 413

Trp Ile Ser Ala Tyr Asp Gly Tyr Arg Asn Tyr Ala Gln Lys Leu Gln
1               5                   10                  15

Gly

<210> SEQ ID NO 414
<211> LENGTH: 13
<212> TYPE: PRT
<213> ORGANISM: Artificial
<220> FEATURE:
<223> OTHER INFORMATION: U1-31-CDR-3h

<400> SEQUENCE: 414

Asp Val Gln Asp Tyr Gly Asp Tyr Asp Tyr Phe Asp Tyr
1               5                   10

<210> SEQ ID NO 415
<211> LENGTH: 11
<212> TYPE: PRT
<213> ORGANISM: Artificial
<220> FEATURE:
<223> OTHER INFORMATION: U1-31-CDR-1l

<400> SEQUENCE: 415

Arg Ala Ser Gln Ser Ile Ser Ser Tyr Leu Asn
1               5                   10
```

<210> SEQ ID NO 416
<211> LENGTH: 7
<212> TYPE: PRT
<213> ORGANISM: Artificial
<220> FEATURE:
<223> OTHER INFORMATION: U1-31-CDR-2l

<400> SEQUENCE: 416

Ala Ala Ser Ser Leu Gln Ser
1               5

<210> SEQ ID NO 417
<211> LENGTH: 9
<212> TYPE: PRT
<213> ORGANISM: Artificial
<220> FEATURE:
<223> OTHER INFORMATION: U1-31-CDR-3l

<400> SEQUENCE: 417

Gln Gln Ser Tyr Ser Thr Pro Ile Thr
1               5

<210> SEQ ID NO 418
<211> LENGTH: 12
<212> TYPE: PRT
<213> ORGANISM: Artificial
<220> FEATURE:
<223> OTHER INFORMATION: U1-32-CDR-1h

<400> SEQUENCE: 418

Gly Gly Ser Ile Ser Ser Gly Asp Tyr Tyr Trp Ser
1               5                   10

<210> SEQ ID NO 419
<211> LENGTH: 16
<212> TYPE: PRT
<213> ORGANISM: Artificial
<220> FEATURE:
<223> OTHER INFORMATION: U1-32-CDR-2h

<400> SEQUENCE: 419

Tyr Ile Tyr Tyr Ser Gly Thr Thr Tyr Tyr Asn Pro Ser Leu Lys Ser
1               5                   10                  15

<210> SEQ ID NO 420
<211> LENGTH: 12
<212> TYPE: PRT
<213> ORGANISM: Artificial
<220> FEATURE:
<223> OTHER INFORMATION: U1-32-CDR-3h

<400> SEQUENCE: 420

Ala Asp Tyr Asp Phe Trp Ser Gly Tyr Phe Asp Tyr
1               5                   10

<210> SEQ ID NO 421
<211> LENGTH: 11
<212> TYPE: PRT
<213> ORGANISM: Artificial
<220> FEATURE:
<223> OTHER INFORMATION: U1-32-CDR-1l

<400> SEQUENCE: 421

Arg Ala Gly Gln Gly Ile Arg Asn Asp Leu Gly
1               5                   10

```
<210> SEQ ID NO 422
<211> LENGTH: 7
<212> TYPE: PRT
<213> ORGANISM: Artificial
<220> FEATURE:
<223> OTHER INFORMATION: U1-32-CDR-2l

<400> SEQUENCE: 422

Ala Ala Ser Ser Leu Gln Ser
1               5

<210> SEQ ID NO 423
<211> LENGTH: 9
<212> TYPE: PRT
<213> ORGANISM: Artificial
<220> FEATURE:
<223> OTHER INFORMATION: U1-32-CDR-3l

<400> SEQUENCE: 423

Leu Gln His Asn Ser Tyr Pro Trp Thr
1               5

<210> SEQ ID NO 424
<211> LENGTH: 12
<212> TYPE: PRT
<213> ORGANISM: Artificial
<220> FEATURE:
<223> OTHER INFORMATION: U1-33-CDR-1h

<400> SEQUENCE: 424

Gly Gly Ser Ile Ser Ser Gly Asp Tyr Tyr Trp Ser
1               5                   10

<210> SEQ ID NO 425
<211> LENGTH: 16
<212> TYPE: PRT
<213> ORGANISM: Artificial
<220> FEATURE:
<223> OTHER INFORMATION: U1-33-CDR-2h

<400> SEQUENCE: 425

Tyr Ile Tyr Tyr Ser Gly Ser Thr Tyr Tyr Asn Pro Ser Leu Lys Ser
1               5                   10                  15

<210> SEQ ID NO 426
<211> LENGTH: 12
<212> TYPE: PRT
<213> ORGANISM: Artificial
<220> FEATURE:
<223> OTHER INFORMATION: U1-33-CDR-3h

<400> SEQUENCE: 426

Ala Asp Tyr Asp Phe Trp Ser Gly His Phe Asp Cys
1               5                   10

<210> SEQ ID NO 427
<211> LENGTH: 11
<212> TYPE: PRT
<213> ORGANISM: Artificial
<220> FEATURE:
<223> OTHER INFORMATION: U1-33-CDR-1l

<400> SEQUENCE: 427

Arg Ala Ser Gln Gly Ile Arg Asp Asp Leu Gly
1               5                   10

<210> SEQ ID NO 428
```

```
<211> LENGTH: 7
<212> TYPE: PRT
<213> ORGANISM: Artificial
<220> FEATURE:
<223> OTHER INFORMATION: U1-33-CDR-2l

<400> SEQUENCE: 428

Ala Glu Ser Ser Leu Gln Ser
1               5

<210> SEQ ID NO 429
<211> LENGTH: 9
<212> TYPE: PRT
<213> ORGANISM: Artificial
<220> FEATURE:
<223> OTHER INFORMATION: U1-33-CDR-3l

<400> SEQUENCE: 429

Leu Gln His His Ser Tyr Pro Trp Thr
1               5

<210> SEQ ID NO 430
<211> LENGTH: 10
<212> TYPE: PRT
<213> ORGANISM: Artificial
<220> FEATURE:
<223> OTHER INFORMATION: U1-34-CDR-1h

<400> SEQUENCE: 430

Gly Tyr Thr Phe Thr Asn Tyr Gly Ile Ser
1               5                   10

<210> SEQ ID NO 431
<211> LENGTH: 17
<212> TYPE: PRT
<213> ORGANISM: Artificial
<220> FEATURE:
<223> OTHER INFORMATION: U1-34-CDR-2h

<400> SEQUENCE: 431

Trp Ile Ser Ala Tyr Asp Gly Tyr Arg Asn Tyr Ala Gln Lys Leu Gln
1               5                   10                  15

Gly

<210> SEQ ID NO 432
<211> LENGTH: 13
<212> TYPE: PRT
<213> ORGANISM: Artificial
<220> FEATURE:
<223> OTHER INFORMATION: U1-34-CDR-3h

<400> SEQUENCE: 432

Asp Val Gln Asp Tyr Gly Asp Tyr Asp Tyr Phe Asp Tyr
1               5                   10

<210> SEQ ID NO 433
<211> LENGTH: 11
<212> TYPE: PRT
<213> ORGANISM: Artificial
<220> FEATURE:
<223> OTHER INFORMATION: U1-34-CDR-1l

<400> SEQUENCE: 433

Arg Ala Ser Gln Ser Ile Ser Ser Tyr Leu Asn
1               5                   10
```

```
<210> SEQ ID NO 434
<211> LENGTH: 7
<212> TYPE: PRT
<213> ORGANISM: Artificial
<220> FEATURE:
<223> OTHER INFORMATION: U1-34-CDR-2l

<400> SEQUENCE: 434

Ala Ala Ser Ser Leu Gln Ser
1               5

<210> SEQ ID NO 435
<211> LENGTH: 9
<212> TYPE: PRT
<213> ORGANISM: Artificial
<220> FEATURE:
<223> OTHER INFORMATION: U1-34-CDR-3l

<400> SEQUENCE: 435

Gln Gln Ser Tyr Ser Thr Pro Ile Thr
1               5

<210> SEQ ID NO 436
<211> LENGTH: 10
<212> TYPE: PRT
<213> ORGANISM: Artificial
<220> FEATURE:
<223> OTHER INFORMATION: U1-35-CDR-1h

<400> SEQUENCE: 436

Gly Phe Thr Phe Ser Asp Tyr Tyr Met Ser
1               5                   10

<210> SEQ ID NO 437
<211> LENGTH: 17
<212> TYPE: PRT
<213> ORGANISM: Artificial
<220> FEATURE:
<223> OTHER INFORMATION: U1-35-CDR-2h

<400> SEQUENCE: 437

Tyr Ile Ser Ser Ser Gly Asn Asn Ile Tyr His Ala Asp Ser Val Lys
1               5                   10                  15

Gly

<210> SEQ ID NO 438
<211> LENGTH: 14
<212> TYPE: PRT
<213> ORGANISM: Artificial
<220> FEATURE:
<223> OTHER INFORMATION: U1-35-CDR-3h

<400> SEQUENCE: 438

Glu Arg Tyr Ser Gly Tyr Asp Asp Pro Asp Gly Phe Asp Ile
1               5                   10

<210> SEQ ID NO 439
<211> LENGTH: 11
<212> TYPE: PRT
<213> ORGANISM: Artificial
<220> FEATURE:
<223> OTHER INFORMATION: U1-35-CDR-1l

<400> SEQUENCE: 439

Gln Ala Ser Gln Asp Ile Ser Asn Tyr Leu Ser
1               5                   10
```

<210> SEQ ID NO 440
<211> LENGTH: 7
<212> TYPE: PRT
<213> ORGANISM: Artificial
<220> FEATURE:
<223> OTHER INFORMATION: U1-35-CDR-2l

<400> SEQUENCE: 440

Asp Ala Ser Asn Leu Glu Thr
1               5

<210> SEQ ID NO 441
<211> LENGTH: 9
<212> TYPE: PRT
<213> ORGANISM: Artificial
<220> FEATURE:
<223> OTHER INFORMATION: U1-35-CDR-3l

<400> SEQUENCE: 441

Gln Gln Tyr Asp Asn Pro Pro Cys Ser
1               5

<210> SEQ ID NO 442
<211> LENGTH: 12
<212> TYPE: PRT
<213> ORGANISM: Artificial
<220> FEATURE:
<223> OTHER INFORMATION: U1-36-CDR-1h

<400> SEQUENCE: 442

Gly Gly Ser Ile Ser Ser Gly Tyr Tyr Tyr Trp Ser
1               5                   10

<210> SEQ ID NO 443
<211> LENGTH: 16
<212> TYPE: PRT
<213> ORGANISM: Artificial
<220> FEATURE:
<223> OTHER INFORMATION: U1-36-CDR-2h

<400> SEQUENCE: 443

Tyr Ile Tyr Tyr Ser Gly Thr Thr Tyr Tyr Asn Pro Ser Phe Lys Ser
1               5                   10                  15

<210> SEQ ID NO 444
<211> LENGTH: 12
<212> TYPE: PRT
<213> ORGANISM: Artificial
<220> FEATURE:
<223> OTHER INFORMATION: U1-36-CDR-3h

<400> SEQUENCE: 444

Ala Asp Tyr Asp Phe Trp Ser Gly His Phe Asp Tyr
1               5                   10

<210> SEQ ID NO 445
<211> LENGTH: 11
<212> TYPE: PRT
<213> ORGANISM: Artificial
<220> FEATURE:
<223> OTHER INFORMATION: U1-36-CDR-1l

<400> SEQUENCE: 445

Arg Ala Ser Gln Gly Ile Arg Asn Asp Leu Gly
1               5                   10

```
<210> SEQ ID NO 446
<211> LENGTH: 7
<212> TYPE: PRT
<213> ORGANISM: Artificial
<220> FEATURE:
<223> OTHER INFORMATION: U1-36-CDR-2l

<400> SEQUENCE: 446

Ala Ala Ser Ser Leu Gln Ser
1               5

<210> SEQ ID NO 447
<211> LENGTH: 9
<212> TYPE: PRT
<213> ORGANISM: Artificial
<220> FEATURE:
<223> OTHER INFORMATION: U1-36-CDR-3l

<400> SEQUENCE: 447

Leu Gln His Asn Ser Tyr Pro Trp Thr
1               5

<210> SEQ ID NO 448
<211> LENGTH: 10
<212> TYPE: PRT
<213> ORGANISM: Artificial
<220> FEATURE:
<223> OTHER INFORMATION: U1-37-CDR-1h

<400> SEQUENCE: 448

Gly Tyr Thr Phe Thr Ser Tyr Gly Ile Ser
1               5                   10

<210> SEQ ID NO 449
<211> LENGTH: 17
<212> TYPE: PRT
<213> ORGANISM: Artificial
<220> FEATURE:
<223> OTHER INFORMATION: U1-37-CDR-2h

<400> SEQUENCE: 449

Trp Ile Ser Ala Tyr Asp Gly His Thr Asn Tyr Ala Gln Lys Leu Gln
1               5                   10                  15

Gly

<210> SEQ ID NO 450
<211> LENGTH: 13
<212> TYPE: PRT
<213> ORGANISM: Artificial
<220> FEATURE:
<223> OTHER INFORMATION: U1-37-CDR-3h

<400> SEQUENCE: 450

Asp Pro His Asp Tyr Ser Asn Tyr Glu Ala Phe Asp Phe
1               5                   10

<210> SEQ ID NO 451
<211> LENGTH: 11
<212> TYPE: PRT
<213> ORGANISM: Artificial
<220> FEATURE:
<223> OTHER INFORMATION: U1-37-CDR-1l

<400> SEQUENCE: 451

Arg Ala Ser Gln Ser Ile Ser Ser Tyr Leu Asn
1               5                   10
```

<210> SEQ ID NO 452
<211> LENGTH: 7
<212> TYPE: PRT
<213> ORGANISM: Artificial
<220> FEATURE:
<223> OTHER INFORMATION: U1-37-CDR-2l

<400> SEQUENCE: 452

Ala Ala Ser Ser Leu Gln Ser
1               5

<210> SEQ ID NO 453
<211> LENGTH: 9
<212> TYPE: PRT
<213> ORGANISM: Artificial
<220> FEATURE:
<223> OTHER INFORMATION: U1-37-CDR-3l

<400> SEQUENCE: 453

Gln Gln Ser Tyr Ser Thr Pro Ile Thr
1               5

<210> SEQ ID NO 454
<211> LENGTH: 12
<212> TYPE: PRT
<213> ORGANISM: Artificial
<220> FEATURE:
<223> OTHER INFORMATION: U1-38-CDR-1h

<400> SEQUENCE: 454

Gly Phe Ser Leu Ser Thr Ser Gly Val Gly Val Gly
1               5                   10

<210> SEQ ID NO 455
<211> LENGTH: 16
<212> TYPE: PRT
<213> ORGANISM: Artificial
<220> FEATURE:
<223> OTHER INFORMATION: U1-38-CDR-2h

<400> SEQUENCE: 455

Leu Ile Tyr Trp Asn Asp Asp Lys Arg Tyr Ser Pro Ser Leu Lys Ser
1               5                   10                  15

<210> SEQ ID NO 456
<211> LENGTH: 9
<212> TYPE: PRT
<213> ORGANISM: Artificial
<220> FEATURE:
<223> OTHER INFORMATION: U1-38-CDR-3h

<400> SEQUENCE: 456

Arg Asp Glu Val Arg Gly Phe Asp Tyr
1               5

<210> SEQ ID NO 457
<211> LENGTH: 16
<212> TYPE: PRT
<213> ORGANISM: Artificial
<220> FEATURE:
<223> OTHER INFORMATION: U1-38-CDR-1l

<400> SEQUENCE: 457

Arg Ser Ser Gln Ser Leu Val Tyr Ser Asp Gly Tyr Thr Tyr Leu His
1               5                   10                  15

```
<210> SEQ ID NO 458
<211> LENGTH: 7
<212> TYPE: PRT
<213> ORGANISM: Artificial
<220> FEATURE:
<223> OTHER INFORMATION: U1-38-CDR-2l

<400> SEQUENCE: 458

Lys Val Ser Asn Trp Asp Ser
1               5

<210> SEQ ID NO 459
<211> LENGTH: 9
<212> TYPE: PRT
<213> ORGANISM: Artificial
<220> FEATURE:
<223> OTHER INFORMATION: U1-38-CDR-3l

<400> SEQUENCE: 459

Met Gln Gly Ala His Trp Pro Ile Thr
1               5

<210> SEQ ID NO 460
<211> LENGTH: 10
<212> TYPE: PRT
<213> ORGANISM: Artificial
<220> FEATURE:
<223> OTHER INFORMATION: U1-39-CDR-1h

<400> SEQUENCE: 460

Gly Phe Thr Val Ser Ser Asn Tyr Met Ser
1               5                   10

<210> SEQ ID NO 461
<211> LENGTH: 16
<212> TYPE: PRT
<213> ORGANISM: Artificial
<220> FEATURE:
<223> OTHER INFORMATION: U1-39-CDR-2h

<400> SEQUENCE: 461

Val Ile Tyr Ser Gly Gly Ser Thr Tyr Tyr Ala Asp Ser Val Lys Gly
1               5                   10                  15

<210> SEQ ID NO 462
<211> LENGTH: 6
<212> TYPE: PRT
<213> ORGANISM: Artificial
<220> FEATURE:
<223> OTHER INFORMATION: U1-39-CDR-3h

<400> SEQUENCE: 462

Gly Gln Trp Leu Asp Val
1               5

<210> SEQ ID NO 463
<211> LENGTH: 16
<212> TYPE: PRT
<213> ORGANISM: Artificial
<220> FEATURE:
<223> OTHER INFORMATION: U1-39-CDR-1l

<400> SEQUENCE: 463

Arg Ser Ser Gln Ser Leu Leu His Ser Asn Gly Tyr Asn Tyr Leu Asp
1               5                   10                  15

<210> SEQ ID NO 464
```

```
<211> LENGTH: 7
<212> TYPE: PRT
<213> ORGANISM: Artificial
<220> FEATURE:
<223> OTHER INFORMATION: U1-39-CDR-2l

<400> SEQUENCE: 464

Leu Gly Phe His Arg Ala Ser
1               5

<210> SEQ ID NO 465
<211> LENGTH: 9
<212> TYPE: PRT
<213> ORGANISM: Artificial
<220> FEATURE:
<223> OTHER INFORMATION: U1-39-CDR-3l

<400> SEQUENCE: 465

Arg Gln Ala Leu Gln Thr Pro Leu Thr
1               5

<210> SEQ ID NO 466
<211> LENGTH: 12
<212> TYPE: PRT
<213> ORGANISM: Artificial
<220> FEATURE:
<223> OTHER INFORMATION: U1-40-CDR-1h

<400> SEQUENCE: 466

Gly Gly Ser Ile Ser Ser Gly Gly Tyr Tyr Trp Ser
1               5                   10

<210> SEQ ID NO 467
<211> LENGTH: 16
<212> TYPE: PRT
<213> ORGANISM: Artificial
<220> FEATURE:
<223> OTHER INFORMATION: U1-40-CDR-2h

<400> SEQUENCE: 467

Tyr Ile Tyr Ser Ser Gly Ser Thr Tyr Tyr Asn Pro Ser Leu Lys Ser
1               5                   10                  15

<210> SEQ ID NO 468
<211> LENGTH: 15
<212> TYPE: PRT
<213> ORGANISM: Artificial
<220> FEATURE:
<223> OTHER INFORMATION: U1-40-CDR-3h

<400> SEQUENCE: 468

Asp Arg Glu Leu Glu Leu Tyr Tyr Tyr Tyr Gly Met Asp Val
1               5                   10                  15

<210> SEQ ID NO 469
<211> LENGTH: 16
<212> TYPE: PRT
<213> ORGANISM: Artificial
<220> FEATURE:
<223> OTHER INFORMATION: U1-40-CDR-1l

<400> SEQUENCE: 469

Arg Ser Ser Gln Ser Leu Leu Tyr Ser Asn Gly Tyr Asn Tyr Leu Asp
1               5                   10                  15

<210> SEQ ID NO 470
<211> LENGTH: 7
```

```
<212> TYPE: PRT
<213> ORGANISM: Artificial
<220> FEATURE:
<223> OTHER INFORMATION: U1-40-CDR-2l

<400> SEQUENCE: 470

Leu Gly Ser Asn Arg Ala Ser
1               5

<210> SEQ ID NO 471
<211> LENGTH: 9
<212> TYPE: PRT
<213> ORGANISM: Artificial
<220> FEATURE:
<223> OTHER INFORMATION: U1-40-CDR-3l

<400> SEQUENCE: 471

Met Gln Ala Leu Gln Thr Pro Leu Thr
1               5

<210> SEQ ID NO 472
<211> LENGTH: 12
<212> TYPE: PRT
<213> ORGANISM: Artificial
<220> FEATURE:
<223> OTHER INFORMATION: U1-41-CDR-1h

<400> SEQUENCE: 472

Gly Gly Ser Ile Ser Ser Gly Gly Tyr Tyr Trp Ser
1               5                   10

<210> SEQ ID NO 473
<211> LENGTH: 16
<212> TYPE: PRT
<213> ORGANISM: Artificial
<220> FEATURE:
<223> OTHER INFORMATION: U1-41-CDR-2h

<400> SEQUENCE: 473

Tyr Ile Tyr Tyr Ser Gly Ser Thr Tyr Tyr Asn Pro Ser Leu Lys Ser
1               5                   10                  15

<210> SEQ ID NO 474
<211> LENGTH: 15
<212> TYPE: PRT
<213> ORGANISM: Artificial
<220> FEATURE:
<223> OTHER INFORMATION: U1-41-CDR-3h

<400> SEQUENCE: 474

Asp Arg Glu Leu Glu Gly Tyr Ser Asn Tyr Tyr Gly Val Asp Val
1               5                   10                  15

<210> SEQ ID NO 475
<211> LENGTH: 11
<212> TYPE: PRT
<213> ORGANISM: Artificial
<220> FEATURE:
<223> OTHER INFORMATION: U1-41-CDR-1l

<400> SEQUENCE: 475

Arg Ala Ser Gln Ala Ile Ser Asn Tyr Leu Asn
1               5                   10

<210> SEQ ID NO 476
<211> LENGTH: 7
<212> TYPE: PRT
```

```
<213> ORGANISM: Artificial
<220> FEATURE:
<223> OTHER INFORMATION: U1-41-CDR-2l

<400> SEQUENCE: 476

Ala Ala Ser Ser Leu Gln Ser
1               5

<210> SEQ ID NO 477
<211> LENGTH: 9
<212> TYPE: PRT
<213> ORGANISM: Artificial
<220> FEATURE:
<223> OTHER INFORMATION: U1-41-CDR-3l

<400> SEQUENCE: 477

Gln Gln Asn Asn Ser Leu Pro Ile Thr
1               5

<210> SEQ ID NO 478
<211> LENGTH: 10
<212> TYPE: PRT
<213> ORGANISM: Artificial
<220> FEATURE:
<223> OTHER INFORMATION: U1-42-CDR-1h

<400> SEQUENCE: 478

Gly Tyr Ser Phe Thr Ser Tyr Trp Ile Gly
1               5                   10

<210> SEQ ID NO 479
<211> LENGTH: 17
<212> TYPE: PRT
<213> ORGANISM: Artificial
<220> FEATURE:
<223> OTHER INFORMATION: U1-42-CDR-2h

<400> SEQUENCE: 479

Ile Ile Tyr Pro Gly Asp Ser Asp Thr Arg Tyr Ser Pro Ser Phe Gln
1               5                   10                  15

Gly

<210> SEQ ID NO 480
<211> LENGTH: 9
<212> TYPE: PRT
<213> ORGANISM: Artificial
<220> FEATURE:
<223> OTHER INFORMATION: U1-42-CDR-3h

<400> SEQUENCE: 480

His Glu Asn Tyr Gly Asp Tyr Asn Tyr
1               5

<210> SEQ ID NO 481
<211> LENGTH: 11
<212> TYPE: PRT
<213> ORGANISM: Artificial
<220> FEATURE:
<223> OTHER INFORMATION: U1-42-CDR-1l

<400> SEQUENCE: 481

Arg Ala Ser Gln Ser Ile Arg Ser Tyr Leu Asn
1               5                   10

<210> SEQ ID NO 482
<211> LENGTH: 7
```

```
<212> TYPE: PRT
<213> ORGANISM: Artificial
<220> FEATURE:
<223> OTHER INFORMATION: U1-42-CDR-2l

<400> SEQUENCE: 482

Ala Ala Ser Ser Leu Gln Ser
1               5

<210> SEQ ID NO 483
<211> LENGTH: 9
<212> TYPE: PRT
<213> ORGANISM: Artificial
<220> FEATURE:
<223> OTHER INFORMATION: U1-42-CDR-3l

<400> SEQUENCE: 483

Gln Gln Ser Asn Gly Ser Pro Leu Thr
1               5

<210> SEQ ID NO 484
<211> LENGTH: 12
<212> TYPE: PRT
<213> ORGANISM: Artificial
<220> FEATURE:
<223> OTHER INFORMATION: U1-43-CDR-1h

<400> SEQUENCE: 484

Gly Gly Ser Ile Ser Ser Gly Gly Tyr Tyr Trp Ser
1               5                   10

<210> SEQ ID NO 485
<211> LENGTH: 16
<212> TYPE: PRT
<213> ORGANISM: Artificial
<220> FEATURE:
<223> OTHER INFORMATION: U1-43-CDR-2h

<400> SEQUENCE: 485

Tyr Ile Tyr Tyr Ser Gly Ser Thr Tyr Tyr Asn Pro Ser Leu Arg Ser
1               5                   10                  15

<210> SEQ ID NO 486
<211> LENGTH: 17
<212> TYPE: PRT
<213> ORGANISM: Artificial
<220> FEATURE:
<223> OTHER INFORMATION: U1-43-CDR-3h

<400> SEQUENCE: 486

Asp Arg Glu Arg Glu Trp Asp Asp Tyr Gly Asp Pro Gln Gly Met Asp
1               5                   10                  15

Val

<210> SEQ ID NO 487
<211> LENGTH: 11
<212> TYPE: PRT
<213> ORGANISM: Artificial
<220> FEATURE:
<223> OTHER INFORMATION: U1-43-CDR-1l

<400> SEQUENCE: 487

Arg Ala Ser Gln Ser Ile Ser Ser Tyr Leu His
1               5                   10

<210> SEQ ID NO 488
```

```
<211> LENGTH: 7
<212> TYPE: PRT
<213> ORGANISM: Artificial
<220> FEATURE:
<223> OTHER INFORMATION: U1-43-CDR-2l

<400> SEQUENCE: 488

Ala Ala Ser Ser Leu Gln Ser
1               5

<210> SEQ ID NO 489
<211> LENGTH: 9
<212> TYPE: PRT
<213> ORGANISM: Artificial
<220> FEATURE:
<223> OTHER INFORMATION: U1-43-CDR-3l

<400> SEQUENCE: 489

Gln Gln Ser Tyr Ser Asn Pro Leu Thr
1               5

<210> SEQ ID NO 490
<211> LENGTH: 10
<212> TYPE: PRT
<213> ORGANISM: Artificial
<220> FEATURE:
<223> OTHER INFORMATION: U1-44-CDR-1h

<400> SEQUENCE: 490

Gly Tyr Ser Phe Thr Ser Tyr Trp Ile Gly
1               5                   10

<210> SEQ ID NO 491
<211> LENGTH: 17
<212> TYPE: PRT
<213> ORGANISM: Artificial
<220> FEATURE:
<223> OTHER INFORMATION: U1-44-CDR-2h

<400> SEQUENCE: 491

Ile Ile Trp Pro Gly Asp Ser Asp Thr Ile Tyr Ser Pro Ser Phe Gln
1               5                   10                  15

Gly

<210> SEQ ID NO 492
<211> LENGTH: 9
<212> TYPE: PRT
<213> ORGANISM: Artificial
<220> FEATURE:
<223> OTHER INFORMATION: U1-44-CDR-3h

<400> SEQUENCE: 492

His Glu Asn Tyr Gly Asp Tyr Asn Tyr
1               5

<210> SEQ ID NO 493
<211> LENGTH: 11
<212> TYPE: PRT
<213> ORGANISM: Artificial
<220> FEATURE:
<223> OTHER INFORMATION: U1-44-CDR-1l

<400> SEQUENCE: 493

Arg Ala Ser Gln Ser Ile Arg Ser Tyr Leu Asn
1               5                   10
```

```
<210> SEQ ID NO 494
<211> LENGTH: 7
<212> TYPE: PRT
<213> ORGANISM: Artificial
<220> FEATURE:
<223> OTHER INFORMATION: U1-44-CDR-2l

<400> SEQUENCE: 494

Ala Ala Ser Ser Leu Gln Ser
1               5

<210> SEQ ID NO 495
<211> LENGTH: 9
<212> TYPE: PRT
<213> ORGANISM: Artificial
<220> FEATURE:
<223> OTHER INFORMATION: U1-44-CDR-3l

<400> SEQUENCE: 495

Gln Gln Ser Ile Ser Ser Pro Leu Thr
1               5

<210> SEQ ID NO 496
<211> LENGTH: 10
<212> TYPE: PRT
<213> ORGANISM: Artificial
<220> FEATURE:
<223> OTHER INFORMATION: U1-45-CDR-1h

<400> SEQUENCE: 496

Gly Tyr Thr Phe Thr Ser Tyr Asp Ile Asn
1               5                   10

<210> SEQ ID NO 497
<211> LENGTH: 17
<212> TYPE: PRT
<213> ORGANISM: Artificial
<220> FEATURE:
<223> OTHER INFORMATION: U1-45-CDR-2h

<400> SEQUENCE: 497

Trp Met Asn Pro Asn Ser Gly Asp Thr Gly Tyr Ala Gln Val Phe Gln
1               5                   10                  15

Gly

<210> SEQ ID NO 498
<211> LENGTH: 16
<212> TYPE: PRT
<213> ORGANISM: Artificial
<220> FEATURE:
<223> OTHER INFORMATION: U1-45-CDR-3h

<400> SEQUENCE: 498

Phe Gly Asp Leu Pro Tyr Asp Tyr Ser Tyr Tyr Glu Trp Phe Asp Pro
1               5                   10                  15

<210> SEQ ID NO 499
<211> LENGTH: 11
<212> TYPE: PRT
<213> ORGANISM: Artificial
<220> FEATURE:
<223> OTHER INFORMATION: U1-45-CDR-1l

<400> SEQUENCE: 499

Arg Ala Ser Gln Ser Ile Ser Ser Tyr Leu Asn
1               5                   10
```

<210> SEQ ID NO 500
<211> LENGTH: 7
<212> TYPE: PRT
<213> ORGANISM: Artificial
<220> FEATURE:
<223> OTHER INFORMATION: U1-45-CDR-2l

<400> SEQUENCE: 500

Ala Ala Ser Ser Leu Gln Ser
1               5

<210> SEQ ID NO 501
<211> LENGTH: 9
<212> TYPE: PRT
<213> ORGANISM: Artificial
<220> FEATURE:
<223> OTHER INFORMATION: U1-45-CDR-3l

<400> SEQUENCE: 501

Gln Gln Ser Tyr Ser Thr Pro Leu Thr
1               5

<210> SEQ ID NO 502
<211> LENGTH: 12
<212> TYPE: PRT
<213> ORGANISM: Artificial
<220> FEATURE:
<223> OTHER INFORMATION: U1-46-CDR-1h

<400> SEQUENCE: 502

Gly Asp Ser Val Ser Ser Asn Ser Ala Ala Trp Asn
1               5                   10

<210> SEQ ID NO 503
<211> LENGTH: 18
<212> TYPE: PRT
<213> ORGANISM: Artificial
<220> FEATURE:
<223> OTHER INFORMATION: U1-46-CDR-2h

<400> SEQUENCE: 503

Arg Thr Tyr Tyr Arg Ser Lys Trp Tyr Asn Asp Tyr Ala Val Ser Val
1               5                   10                  15

Lys Ser

<210> SEQ ID NO 504
<211> LENGTH: 17
<212> TYPE: PRT
<213> ORGANISM: Artificial
<220> FEATURE:
<223> OTHER INFORMATION: U1-46-CDR-3h

<400> SEQUENCE: 504

Asp Leu Tyr Asp Phe Trp Ser Gly Tyr Pro Tyr Tyr Tyr Gly Met Asp
1               5                   10                  15

Val

<210> SEQ ID NO 505
<211> LENGTH: 12
<212> TYPE: PRT
<213> ORGANISM: Artificial
<220> FEATURE:
<223> OTHER INFORMATION: U1-47-CDR-1h

<400> SEQUENCE: 505

```
Gly Asp Ser Val Ser Ser Asn Ser Ala Ala Trp Asn
1               5                   10
```

<210> SEQ ID NO 506
<211> LENGTH: 18
<212> TYPE: PRT
<213> ORGANISM: Artificial
<220> FEATURE:
<223> OTHER INFORMATION: U1-47-CDR-2h

<400> SEQUENCE: 506

```
Arg Thr Tyr Tyr Arg Ser Lys Trp Tyr Asn Asp Tyr Ala Val Ser Val
1               5                   10                  15

Lys Ser
```

<210> SEQ ID NO 507
<211> LENGTH: 16
<212> TYPE: PRT
<213> ORGANISM: Artificial
<220> FEATURE:
<223> OTHER INFORMATION: U1-47-CDR-3h

<400> SEQUENCE: 507

```
Asp Tyr Tyr Gly Ser Gly Ser Phe Tyr Tyr Tyr Gly Met Asp Val
1               5                   10                  15
```

<210> SEQ ID NO 508
<211> LENGTH: 11
<212> TYPE: PRT
<213> ORGANISM: Artificial
<220> FEATURE:
<223> OTHER INFORMATION: U1-47-CDR-1l

<400> SEQUENCE: 508

```
Arg Ala Ser Gln Ser Ile Ser Ser Tyr Leu Asn
1               5                   10
```

<210> SEQ ID NO 509
<211> LENGTH: 7
<212> TYPE: PRT
<213> ORGANISM: Artificial
<220> FEATURE:
<223> OTHER INFORMATION: U1-47-CDR-2l

<400> SEQUENCE: 509

```
Ala Ala Ser Asn Leu Gln Ser
1               5
```

<210> SEQ ID NO 510
<211> LENGTH: 9
<212> TYPE: PRT
<213> ORGANISM: Artificial
<220> FEATURE:
<223> OTHER INFORMATION: U1-47-CDR-3l

<400> SEQUENCE: 510

```
Gln Gln Ser Tyr Ser Thr Pro Arg Thr
1               5
```

<210> SEQ ID NO 511
<211> LENGTH: 10
<212> TYPE: PRT
<213> ORGANISM: Artificial
<220> FEATURE:
<223> OTHER INFORMATION: U1-48-CDR-1h

<400> SEQUENCE: 511

```
Gly Gly Ser Ile Ser Ser Tyr Tyr Trp Ser
1               5                   10

<210> SEQ ID NO 512
<211> LENGTH: 16
<212> TYPE: PRT
<213> ORGANISM: Artificial
<220> FEATURE:
<223> OTHER INFORMATION: U1-48-CDR-2h

<400> SEQUENCE: 512

His Ile Tyr Thr Ser Gly Ser Thr Asn Tyr Asn Pro Ser Leu Lys Ser
1               5                   10                  15

<210> SEQ ID NO 513
<211> LENGTH: 16
<212> TYPE: PRT
<213> ORGANISM: Artificial
<220> FEATURE:
<223> OTHER INFORMATION: U1-48-CDR-3h

<400> SEQUENCE: 513

Glu Ala Ile Phe Gly Val Gly Pro Tyr Tyr Tyr Tyr Gly Met Asp Val
1               5                   10                  15

<210> SEQ ID NO 514
<211> LENGTH: 10
<212> TYPE: PRT
<213> ORGANISM: Artificial
<220> FEATURE:
<223> OTHER INFORMATION: U1-49-CDR-1h

<400> SEQUENCE: 514

Gly Tyr Thr Phe Thr Gly Tyr Tyr Met His
1               5                   10

<210> SEQ ID NO 515
<211> LENGTH: 17
<212> TYPE: PRT
<213> ORGANISM: Artificial
<220> FEATURE:
<223> OTHER INFORMATION: U1-49-CDR-2h

<400> SEQUENCE: 515

Trp Ile Asn Pro Asn Ile Gly Gly Thr Asn Cys Ala Gln Lys Phe Gln
1               5                   10                  15
Gly

<210> SEQ ID NO 516
<211> LENGTH: 17
<212> TYPE: PRT
<213> ORGANISM: Artificial
<220> FEATURE:
<223> OTHER INFORMATION: U1-49-CDR-3h

<400> SEQUENCE: 516

Gly Gly Arg Tyr Ser Ser Ser Trp Ser Tyr Tyr Tyr Tyr Gly Met Asp
1               5                   10                  15
Val

<210> SEQ ID NO 517
<211> LENGTH: 16
<212> TYPE: PRT
<213> ORGANISM: Artificial
<220> FEATURE:
```

<223> OTHER INFORMATION: U1-49-CDR-1l

<400> SEQUENCE: 517

Lys Ser Ser Gln Ser Leu Leu Leu Ser Asp Gly Gly Thr Tyr Leu Tyr
1               5                   10                  15

<210> SEQ ID NO 518
<211> LENGTH: 7
<212> TYPE: PRT
<213> ORGANISM: Artificial
<220> FEATURE:
<223> OTHER INFORMATION: U1-49-CDR-2l

<400> SEQUENCE: 518

Glu Val Ser Asn Arg Phe Ser
1               5

<210> SEQ ID NO 519
<211> LENGTH: 9
<212> TYPE: PRT
<213> ORGANISM: Artificial
<220> FEATURE:
<223> OTHER INFORMATION: U1-49-CDR-3l

<400> SEQUENCE: 519

Met Gln Ser Met Gln Leu Pro Ile Thr
1               5

<210> SEQ ID NO 520
<211> LENGTH: 12
<212> TYPE: PRT
<213> ORGANISM: Artificial
<220> FEATURE:
<223> OTHER INFORMATION: U1-50-CDR-1h

<400> SEQUENCE: 520

Gly Gly Ser Val Ser Ser Gly Gly Tyr Tyr Trp Ser
1               5                   10

<210> SEQ ID NO 521
<211> LENGTH: 16
<212> TYPE: PRT
<213> ORGANISM: Artificial
<220> FEATURE:
<223> OTHER INFORMATION: U1-50-CDR-2h

<400> SEQUENCE: 521

Tyr Ile Tyr Tyr Ser Gly Ser Thr Asn Tyr Asn Pro Ser Leu Lys Ser
1               5                   10                  15

<210> SEQ ID NO 522
<211> LENGTH: 17
<212> TYPE: PRT
<213> ORGANISM: Artificial
<220> FEATURE:
<223> OTHER INFORMATION: U1-50-CDR-3h

<400> SEQUENCE: 522

Gly Gly Asp Ser Asn Tyr Glu Asp Tyr Tyr Tyr Tyr Gly Met Asp
1               5                   10                  15

Val

<210> SEQ ID NO 523
<211> LENGTH: 11
<212> TYPE: PRT
<213> ORGANISM: Artificial

<220> FEATURE:
<223> OTHER INFORMATION: U1-50-CDR-1l

<400> SEQUENCE: 523

Arg Ala Ser Gln Ser Ile Ser Ile Tyr Leu His
1               5                   10

<210> SEQ ID NO 524
<211> LENGTH: 7
<212> TYPE: PRT
<213> ORGANISM: Artificial
<220> FEATURE:
<223> OTHER INFORMATION: U1-50-CDR-2l

<400> SEQUENCE: 524

Ala Ala Ser Ser Leu Gln Ser
1               5

<210> SEQ ID NO 525
<211> LENGTH: 9
<212> TYPE: PRT
<213> ORGANISM: Artificial
<220> FEATURE:
<223> OTHER INFORMATION: U1-50-CDR-3l

<400> SEQUENCE: 525

Gln Gln Ser Tyr Thr Ser Pro Ile Thr
1               5

<210> SEQ ID NO 526
<211> LENGTH: 10
<212> TYPE: PRT
<213> ORGANISM: Artificial
<220> FEATURE:
<223> OTHER INFORMATION: U1-51-CDR-1h

<400> SEQUENCE: 526

Gly Gly Ser Ile Ser Ser Tyr Tyr Trp Ser
1               5                   10

<210> SEQ ID NO 527
<211> LENGTH: 16
<212> TYPE: PRT
<213> ORGANISM: Artificial
<220> FEATURE:
<223> OTHER INFORMATION: U1-51-CDR-2h

<400> SEQUENCE: 527

Tyr Ile Tyr Tyr Ser Gly Ser Thr Asn Tyr Asn Pro Ser Leu Lys Ser
1               5                   10                  15

<210> SEQ ID NO 528
<211> LENGTH: 19
<212> TYPE: PRT
<213> ORGANISM: Artificial
<220> FEATURE:
<223> OTHER INFORMATION: U1-51-CDR-3h

<400> SEQUENCE: 528

Asp Ser Ser Tyr Tyr Asp Ser Ser Gly Tyr Tyr Leu Tyr Tyr Tyr Ala
1               5                   10                  15

Met Asp Val

<210> SEQ ID NO 529
<211> LENGTH: 17
<212> TYPE: PRT

-continued

```
<213> ORGANISM: Artificial
<220> FEATURE:
<223> OTHER INFORMATION: U1-51-CDR-1l

<400> SEQUENCE: 529

Lys Ser Ser Gln Ser Val Leu Tyr Ser Ser Asn Asn Lys Asn Tyr Leu
1               5                   10                  15

Ala

<210> SEQ ID NO 530
<211> LENGTH: 7
<212> TYPE: PRT
<213> ORGANISM: Artificial
<220> FEATURE:
<223> OTHER INFORMATION: U1-51-CDR-2l

<400> SEQUENCE: 530

Trp Ala Ser Thr Arg Glu Ser
1               5

<210> SEQ ID NO 531
<211> LENGTH: 9
<212> TYPE: PRT
<213> ORGANISM: Artificial
<220> FEATURE:
<223> OTHER INFORMATION: U1-51-CDR-3l

<400> SEQUENCE: 531

Gln Gln Tyr Tyr Thr Thr Pro Leu Thr
1               5

<210> SEQ ID NO 532
<211> LENGTH: 12
<212> TYPE: PRT
<213> ORGANISM: Artificial
<220> FEATURE:
<223> OTHER INFORMATION: U1-52-CDR-1h

<400> SEQUENCE: 532

Gly Gly Ser Ile Ser Ser Gly Gly Tyr Tyr Trp Ser
1               5                   10

<210> SEQ ID NO 533
<211> LENGTH: 16
<212> TYPE: PRT
<213> ORGANISM: Artificial
<220> FEATURE:
<223> OTHER INFORMATION: U1-52-CDR-2h

<400> SEQUENCE: 533

Asn Ile Tyr Tyr Ser Gly Ser Thr Tyr Tyr Asn Pro Ser Leu Lys Ser
1               5                   10                  15

<210> SEQ ID NO 534
<211> LENGTH: 15
<212> TYPE: PRT
<213> ORGANISM: Artificial
<220> FEATURE:
<223> OTHER INFORMATION: U1-52-CDR-3h

<400> SEQUENCE: 534

Gly Gly Thr Gly Thr Asn Tyr Tyr Tyr Tyr Gly Met Asp Val
1               5                   10                  15

<210> SEQ ID NO 535
<211> LENGTH: 12
```

<212> TYPE: PRT
<213> ORGANISM: Artificial
<220> FEATURE:
<223> OTHER INFORMATION: U1-52-CDR-1l

<400> SEQUENCE: 535

Arg Ala Ser Gln Ser Val Ser Ser Ser Tyr Leu Ala
1               5                   10

<210> SEQ ID NO 536
<211> LENGTH: 7
<212> TYPE: PRT
<213> ORGANISM: Artificial
<220> FEATURE:
<223> OTHER INFORMATION: U1-52-CDR-2l

<400> SEQUENCE: 536

Gly Ala Ser Ser Trp Ala Thr
1               5

<210> SEQ ID NO 537
<211> LENGTH: 9
<212> TYPE: PRT
<213> ORGANISM: Artificial
<220> FEATURE:
<223> OTHER INFORMATION: U1-52-CDR-3l

<400> SEQUENCE: 537

Gln Gln Tyr Gly Ser Ser Pro Leu Thr
1               5

<210> SEQ ID NO 538
<211> LENGTH: 10
<212> TYPE: PRT
<213> ORGANISM: Artificial
<220> FEATURE:
<223> OTHER INFORMATION: U1-53-CDR-1h

<400> SEQUENCE: 538

Gly Phe Thr Phe Ser Ile Tyr Ser Met Asn
1               5                   10

<210> SEQ ID NO 539
<211> LENGTH: 17
<212> TYPE: PRT
<213> ORGANISM: Artificial
<220> FEATURE:
<223> OTHER INFORMATION: U1-53-CDR-2h

<400> SEQUENCE: 539

Tyr Ile Ser Ser Ser Ser Ser Thr Ile Tyr Tyr Ala Asp Ser Val Lys
1               5                   10                  15

Gly

<210> SEQ ID NO 540
<211> LENGTH: 10
<212> TYPE: PRT
<213> ORGANISM: Artificial
<220> FEATURE:
<223> OTHER INFORMATION: U1-53-CDR-3h

<400> SEQUENCE: 540

Asp Arg Gly Asp Phe Asp Ala Phe Asp Ile
1               5                   10

<210> SEQ ID NO 541

```
<211> LENGTH: 11
<212> TYPE: PRT
<213> ORGANISM: Artificial
<220> FEATURE:
<223> OTHER INFORMATION: U1-53-CDR-1l

<400> SEQUENCE: 541

Gln Ala Ser Gln Asp Ile Thr Asn Tyr Leu Asn
1               5                   10

<210> SEQ ID NO 542
<211> LENGTH: 7
<212> TYPE: PRT
<213> ORGANISM: Artificial
<220> FEATURE:
<223> OTHER INFORMATION: U1-53-CDR-2l

<400> SEQUENCE: 542

Asp Ala Ser Asn Leu Glu Thr
1               5

<210> SEQ ID NO 543
<211> LENGTH: 9
<212> TYPE: PRT
<213> ORGANISM: Artificial
<220> FEATURE:
<223> OTHER INFORMATION: U1-53-CDR-3l

<400> SEQUENCE: 543

Gln Gln Cys Glu Asn Phe Pro Ile Thr
1               5

<210> SEQ ID NO 544
<211> LENGTH: 12
<212> TYPE: PRT
<213> ORGANISM: Artificial
<220> FEATURE:
<223> OTHER INFORMATION: U1-55.1-CDR-1h

<400> SEQUENCE: 544

Gly Gly Ser Val Ser Ser Gly Gly Tyr Tyr Trp Asn
1               5                   10

<210> SEQ ID NO 545
<211> LENGTH: 16
<212> TYPE: PRT
<213> ORGANISM: Artificial
<220> FEATURE:
<223> OTHER INFORMATION: U1-55.1-CDR-2h

<400> SEQUENCE: 545

Tyr Ile Asn Tyr Ser Gly Ser Thr Asn Tyr Asn Pro Ser Leu Lys Ser
1               5                   10                  15

<210> SEQ ID NO 546
<211> LENGTH: 15
<212> TYPE: PRT
<213> ORGANISM: Artificial
<220> FEATURE:
<223> OTHER INFORMATION: U1-55.1-CDR-3h

<400> SEQUENCE: 546

Asp Arg Glu Leu Glu Leu Tyr Tyr Tyr Tyr Tyr Gly Met Asp Val
1               5                   10                  15

<210> SEQ ID NO 547
<211> LENGTH: 16
```

```
<212> TYPE: PRT
<213> ORGANISM: Artificial
<220> FEATURE:
<223> OTHER INFORMATION: U1-55-CDR-1l

<400> SEQUENCE: 547

Arg Ser Ser Gln Ser Leu Leu Tyr Ser Asn Gly Tyr Lys Tyr Leu Asp
1               5                   10                  15

<210> SEQ ID NO 548
<211> LENGTH: 7
<212> TYPE: PRT
<213> ORGANISM: Artificial
<220> FEATURE:
<223> OTHER INFORMATION: U1-55-CDR-2l

<400> SEQUENCE: 548

Leu Gly Ser Asn Arg Ala Ser
1               5

<210> SEQ ID NO 549
<211> LENGTH: 9
<212> TYPE: PRT
<213> ORGANISM: Artificial
<220> FEATURE:
<223> OTHER INFORMATION: U1-55-CDR-3l

<400> SEQUENCE: 549

Met Gln Ala Leu Gln Thr Pro Ile Thr
1               5

<210> SEQ ID NO 550
<211> LENGTH: 16
<212> TYPE: PRT
<213> ORGANISM: Artificial
<220> FEATURE:
<223> OTHER INFORMATION: U1-57.1-CDR-1l

<400> SEQUENCE: 550

Arg Ser Ser Gln Ser Leu Leu Tyr Ser Asn Gly Tyr Lys Tyr Leu Asp
1               5                   10                  15

<210> SEQ ID NO 551
<211> LENGTH: 7
<212> TYPE: PRT
<213> ORGANISM: Artificial
<220> FEATURE:
<223> OTHER INFORMATION: U1-57.1-CDR-2l

<400> SEQUENCE: 551

Leu Gly Ser Asn Arg Ala Ser
1               5

<210> SEQ ID NO 552
<211> LENGTH: 9
<212> TYPE: PRT
<213> ORGANISM: Artificial
<220> FEATURE:
<223> OTHER INFORMATION: U1-57.1-CDR-3l

<400> SEQUENCE: 552

Met Gln Ala Leu Gln Thr Pro Ile Thr
1               5

<210> SEQ ID NO 553
<211> LENGTH: 12
<212> TYPE: PRT
```

<213> ORGANISM: Artificial
<220> FEATURE:
<223> OTHER INFORMATION: U1-57_CDR-1h

<400> SEQUENCE: 553

Gly Gly Ser Val Ser Ser Gly Gly Tyr Tyr Trp Asn
1               5                   10

<210> SEQ ID NO 554
<211> LENGTH: 16
<212> TYPE: PRT
<213> ORGANISM: Artificial
<220> FEATURE:
<223> OTHER INFORMATION: U1-57_CDR-2h

<400> SEQUENCE: 554

Tyr Ile Asn Tyr Ser Gly Ser Thr Asn Tyr Asn Pro Ser Leu Lys Ser
1               5                   10                  15

<210> SEQ ID NO 555
<211> LENGTH: 15
<212> TYPE: PRT
<213> ORGANISM: Artificial
<220> FEATURE:
<223> OTHER INFORMATION: U1-57_CDR-3h

<400> SEQUENCE: 555

Asp Arg Glu Leu Glu Leu Tyr Tyr Tyr Tyr Tyr Gly Met Asp Val
1               5                   10                  15

<210> SEQ ID NO 556
<211> LENGTH: 10
<212> TYPE: PRT
<213> ORGANISM: Artificial
<220> FEATURE:
<223> OTHER INFORMATION: U1-58-CDR-1h

<400> SEQUENCE: 556

Gly Phe Thr Phe Ser Ser Tyr Gly Met His
1               5                   10

<210> SEQ ID NO 557
<211> LENGTH: 17
<212> TYPE: PRT
<213> ORGANISM: Artificial
<220> FEATURE:
<223> OTHER INFORMATION: U1-58-CDR-2h

<400> SEQUENCE: 557

Val Ile Trp Tyr Asp Gly Ser Asn Lys Tyr Tyr Ala Asp Ser Val Lys
1               5                   10                  15
Gly

<210> SEQ ID NO 558
<211> LENGTH: 12
<212> TYPE: PRT
<213> ORGANISM: Artificial
<220> FEATURE:
<223> OTHER INFORMATION: U1-58-CDR-3h

<400> SEQUENCE: 558

Ala Ala Arg Leu Asp Tyr Tyr Tyr Gly Met Asp Val
1               5                   10

<210> SEQ ID NO 559
<211> LENGTH: 11

<212> TYPE: PRT
<213> ORGANISM: Artificial
<220> FEATURE:
<223> OTHER INFORMATION: U1-58-CDR-1l

<400> SEQUENCE: 559

Arg Ala Ser Gln Ser Ile Asn Ser Tyr Leu Asn
1               5                   10

<210> SEQ ID NO 560
<211> LENGTH: 7
<212> TYPE: PRT
<213> ORGANISM: Artificial
<220> FEATURE:
<223> OTHER INFORMATION: U1-58-CDR-2l

<400> SEQUENCE: 560

Gly Ala Ser Gly Leu Gln Ser
1               5

<210> SEQ ID NO 561
<211> LENGTH: 9
<212> TYPE: PRT
<213> ORGANISM: Artificial
<220> FEATURE:
<223> OTHER INFORMATION: U1-58-CDR-3l

<400> SEQUENCE: 561

Gln Gln Ser Tyr Ser Ser Pro Leu Thr
1               5

<210> SEQ ID NO 562
<211> LENGTH: 10
<212> TYPE: PRT
<213> ORGANISM: Artificial
<220> FEATURE:
<223> OTHER INFORMATION: U1-59-CDR-1h

<400> SEQUENCE: 562

Gly Gly Ser Phe Ser Gly Tyr Tyr Trp Ser
1               5                   10

<210> SEQ ID NO 563
<211> LENGTH: 16
<212> TYPE: PRT
<213> ORGANISM: Artificial
<220> FEATURE:
<223> OTHER INFORMATION: U1-59-CDR-2h

<400> SEQUENCE: 563

Glu Ile Asn His Ser Gly Ser Thr Asn Tyr Asn Pro Ser Leu Lys Ser
1               5                   10                  15

<210> SEQ ID NO 564
<211> LENGTH: 9
<212> TYPE: PRT
<213> ORGANISM: Artificial
<220> FEATURE:
<223> OTHER INFORMATION: U1-59-CDR-3h

<400> SEQUENCE: 564

Asp Lys Trp Thr Trp Tyr Phe Asp Leu
1               5

<210> SEQ ID NO 565
<211> LENGTH: 17
<212> TYPE: PRT

```
<213> ORGANISM: Artificial
<220> FEATURE:
<223> OTHER INFORMATION: U1-59-CDR-1l

<400> SEQUENCE: 565

Arg Ser Ser Gln Ser Val Leu Tyr Ser Ser Asn Arg Asn Tyr Leu
1               5                   10                  15

Ala

<210> SEQ ID NO 566
<211> LENGTH: 7
<212> TYPE: PRT
<213> ORGANISM: Artificial
<220> FEATURE:
<223> OTHER INFORMATION: U1-59-CDR-2l

<400> SEQUENCE: 566

Trp Ala Ser Thr Arg Glu Ser
1               5

<210> SEQ ID NO 567
<211> LENGTH: 9
<212> TYPE: PRT
<213> ORGANISM: Artificial
<220> FEATURE:
<223> OTHER INFORMATION: U1-59-CDR-3l

<400> SEQUENCE: 567

Gln Gln Tyr Tyr Ser Thr Pro Arg Thr
1               5

<210> SEQ ID NO 568
<211> LENGTH: 12
<212> TYPE: PRT
<213> ORGANISM: Artificial
<220> FEATURE:
<223> OTHER INFORMATION: U1-61.1-CDR-1h

<400> SEQUENCE: 568

Gly Val Ser Ile Ser Ser Gly Gly Tyr Tyr Trp Ser
1               5                   10

<210> SEQ ID NO 569
<211> LENGTH: 16
<212> TYPE: PRT
<213> ORGANISM: Artificial
<220> FEATURE:
<223> OTHER INFORMATION: U1-61.1-CDR-2h

<400> SEQUENCE: 569

Tyr Ile Tyr Tyr Ser Gly Ser Thr Tyr Tyr Asn Pro Ser Leu Lys Ser
1               5                   10                  15

<210> SEQ ID NO 570
<211> LENGTH: 16
<212> TYPE: PRT
<213> ORGANISM: Artificial
<220> FEATURE:
<223> OTHER INFORMATION: U1-61.1-CDR-3h

<400> SEQUENCE: 570

Asp Ser Glu Ser Glu Tyr Ser Ser Ser Asn Tyr Gly Met Asp Val
1               5                   10                  15

<210> SEQ ID NO 571
<211> LENGTH: 11
```

```
<212> TYPE: PRT
<213> ORGANISM: Artificial
<220> FEATURE:
<223> OTHER INFORMATION: U1-61.1-CDR-1l

<400> SEQUENCE: 571

Arg Ala Ser Gln Thr Ile Ser Ser Tyr Leu Asn
1               5                   10

<210> SEQ ID NO 572
<211> LENGTH: 7
<212> TYPE: PRT
<213> ORGANISM: Artificial
<220> FEATURE:
<223> OTHER INFORMATION: U1-61.1-CDR-2l

<400> SEQUENCE: 572

Ala Ala Ser Ser Leu Gln Gly
1               5

<210> SEQ ID NO 573
<211> LENGTH: 9
<212> TYPE: PRT
<213> ORGANISM: Artificial
<220> FEATURE:
<223> OTHER INFORMATION: U1-61.1-CDR-3l

<400> SEQUENCE: 573

Gln Gln Ser Tyr Ser Asn Pro Leu Thr
1               5

<210> SEQ ID NO 574
<211> LENGTH: 12
<212> TYPE: PRT
<213> ORGANISM: Artificial
<220> FEATURE:
<223> OTHER INFORMATION: U1-61-CDR-1h

<400> SEQUENCE: 574

Gly Val Ser Ile Ser Ser Gly Gly Tyr Tyr Trp Ser
1               5                   10

<210> SEQ ID NO 575
<211> LENGTH: 16
<212> TYPE: PRT
<213> ORGANISM: Artificial
<220> FEATURE:
<223> OTHER INFORMATION: U1-61-CDR-2h

<400> SEQUENCE: 575

Tyr Ile Tyr Tyr Ser Gly Ser Thr Tyr Tyr Asn Pro Ser Leu Lys Ser
1               5                   10                  15

<210> SEQ ID NO 576
<211> LENGTH: 16
<212> TYPE: PRT
<213> ORGANISM: Artificial
<220> FEATURE:
<223> OTHER INFORMATION: U1-61-CDR-3h

<400> SEQUENCE: 576

Asp Ser Glu Ser Glu Tyr Ser Ser Ser Asn Tyr Gly Met Asp Val
1               5                   10                  15

<210> SEQ ID NO 577
<211> LENGTH: 10
<212> TYPE: PRT
```

```
<213> ORGANISM: Artificial
<220> FEATURE:
<223> OTHER INFORMATION: U1-62-CDR-1h

<400> SEQUENCE: 577

Gly Tyr Ser Phe Thr Ser Tyr Trp Ile Gly
1               5                   10

<210> SEQ ID NO 578
<211> LENGTH: 17
<212> TYPE: PRT
<213> ORGANISM: Artificial
<220> FEATURE:
<223> OTHER INFORMATION: U1-62-CDR-2h

<400> SEQUENCE: 578

Ile Ile Tyr Pro Gly Asp Ser Asp Thr Arg Tyr Ser Pro Ser Phe Gln
1               5                   10                  15

Gly

<210> SEQ ID NO 579
<211> LENGTH: 12
<212> TYPE: PRT
<213> ORGANISM: Artificial
<220> FEATURE:
<223> OTHER INFORMATION: U1-62-CDR-3h

<400> SEQUENCE: 579

Gln Met Ala Gly Asn Tyr Tyr Tyr Gly Met Asp Val
1               5                   10

<210> SEQ ID NO 580
<211> LENGTH: 12
<212> TYPE: PRT
<213> ORGANISM: Artificial
<220> FEATURE:
<223> OTHER INFORMATION: U1-62-CDR-1l

<400> SEQUENCE: 580

Arg Ala Ser Gln Ser Val Ile Ser Ile Tyr Leu Ala
1               5                   10

<210> SEQ ID NO 581
<211> LENGTH: 7
<212> TYPE: PRT
<213> ORGANISM: Artificial
<220> FEATURE:
<223> OTHER INFORMATION: U1-62-CDR-2l

<400> SEQUENCE: 581

Gly Ala Ser Ser Arg Ala Thr
1               5

<210> SEQ ID NO 582
<211> LENGTH: 9
<212> TYPE: PRT
<213> ORGANISM: Artificial
<220> FEATURE:
<223> OTHER INFORMATION: U1-62-CDR-3l

<400> SEQUENCE: 582

Gln Gln Tyr Gly Ser Ser Pro Cys Ser
1               5
```